United States Patent [19]

Steinert et al.

[11] Patent Number: 5,616,500
[45] Date of Patent: Apr. 1, 1997

[54] TRICHOHYALIN AND TRANSGLUTAMINASE-3 AND METHODS OF USING SAME

[75] Inventors: Peter M. Steinert; In-Gyu Kim; Soo-Il Chung, all of Rockville, Md.; Sang-chul Park, Seoul, Rep. of Korea

[73] Assignee: The United States of America as represented by the Department of Health & Human Services, Washington, D.C.

[21] Appl. No.: 56,200

[22] Filed: Apr. 30, 1993

[51] Int. Cl.$^6$ .......................... C12N 15/00; C12P 21/06; C12H 9/10; C07H 19/00
[52] U.S. Cl. ............. 435/320.1; 435/69.1; 435/193; 435/325; 435/348; 536/22.1; 536/23.1; 536/23.2; 536/235; 536/24.3; 536/24.31; 536/24.33
[58] Field of Search ...................... 435/69.1, 193, 435/240.2, 320.1; 536/22.1, 23.1, 23.2, 23.5, 24.3, 24.31, 24.33

[56] References Cited

FOREIGN PATENT DOCUMENTS 0379606 8/1990 European Pat. Off. .

OTHER PUBLICATIONS

Kim et al. "The Deduced Sequence of the Novel Protransglutaminase . . . " J.B.C. 268:17 pp. 12682–12690 1993.
Kim et al. "The Complete Amino Acid Sequence . . . " J.B.C. 266:1 pp. 536–539 1991.
Kim et al. "Protransglutaminase E . . . " J.B.C. 265:35 pp. 21971–21978 1990.
Lee et al. "Generation of cDNA Probes . . . " Science 239:1288–1291 1988.
Park, et al., "Expression of Transglutaminase E in Cultured Human Keratinocytes and Skin Tissues", *Progress in Clinical Biochemistry*, pp. 275–278, 1992.
Kim, et al., "The Deduced Sequence of the Novel Protransglutaminase E (TGase3) of Human and Mouse", *Journal of Biological Chemistry*, vol. 268, No. 17, pp. 12682–12690, Jun. 15, 1993.
Lee, et al., "The Structure of Human Trichohyalin", *Journal of Biological Chemistry*, vol. 268, No. 16, pp. 12164–12178, Jun. 5, 1993.

*Primary Examiner*—Dian C. Jacobson
*Assistant Examiner*—Hyosuk Kim
*Attorney, Agent, or Firm*—Knobbe Martens Olson & Bear

[57] ABSTRACT

The sequences of a pair of human proteins, trichohyalin and transglutaminase-3, in addition to the sequence of the mouse transglutaminase-3 protein, have been discovered. The enzyme transglutaminase-3 is used to cross-link the structural protein trichohyalin in order to form a gel.

12 Claims, 48 Drawing Sheets

FIG. 3A

```
                                                                    potential CAAT boxes
AACAAGCCAT TTGTGGAGAC AGAGGTGGAG CTGGGCTTGG TTAGGAATGA ATCAGGCCAT    60
                                                         potential TATA boxes
TCCACAGAGT GGGTGTCTCC TTCCCAAGTT GCTTTCCAGG GCACAATTAA AACCCTATA   120
         likely capsite
AAAGGCCCAG CTCCCAGTTA CCCAGTACAC TTGCCTGTGG TGTCAGCAAG CACTGTCGAC   180
            Exon I    Intron 1
TTCTTCCTCT GGTGAAGTGG GTAAGTCCCA TTCTGTGGGA TCGTGGTCTT CTTTATGATT   240

CTCCATTTTT ATAGCTATTT CAGATGTTGG GATATGGGGG GAGGTTCCAT GTGCCAGAAG   300

GTATCAGTAT TGCAGGGATA AATAAAACTAT CACTAACTCT ATCCCATCTT CTTATGGTTG  360

GAGCCATCAC TTGAACTGAA GCATGACCCT TCTCCTTGGG CTCTGAACTC TATACTTCTG   420

CACATCAAGG ATGATCATGT GTGGCTCTGA TAGGGTTCAT CTTCCTAAAA ACTGCTATCT   480

CAAAAGTTTG CCAGCCTTCT GTTCTCTTTT ACATTGGTTC TACCTAATAT GGGCCATATT   540

CATACAGTCA CAGCATTTAA GGTACTGGAG TTGAGAAGTA CATAAAGAAG TCAGCTAGAT   600

GAACGACTAC CTTATCCCAC CAGCAAAGCC ATTCCATGTA TTCTTATAAC ATTGATCTAC   660

TGCTGGCTAA TGTTTTATAA AAAGCCAAGA TTCCAATGAT GCATTTGGGT TTAACAAAAC   720

CAATATCATT CACAGTTTTC TGGATTCCGT TTGGTTTAGA AAGGACCTCT CAGAAGCTTT   780

CAATACTTCA ATATCCGAAT ATCTTACTAT ATCTGAGTTG AGGCAGGTAA TATACAGTCT   840

CTGTTTTCTG CATTTGTGTA TCTGAATGTT ACATGCCATC TTTTGACTAG GAAGAAGTAC   900

TATTTAATCT TAGAATTGCT GACTTACAAA TTATATTCTA TAAGAGTTCC TAAATCCCTT   960

TATGGACTGT AATGTTGAGG AATCATTCAT ATTCCCTTTT CATTGTTCTA TTTTCTACCA  1020
```

FIG. 3B

```
ATCGTTTTGC TGACATGGCC TCTATCCACT TTAAGATACT CTCAAGTCTT CCTTCACCTT      1080
TTGGCTTTAC CTGTCCCTCT CGCTCAACTT TAAAGGAAGG TGTGTAGCCA TATATAAAAT      1140
TTTAATTTCT GCACTCTTCT CTTAATTTTC TACTCTGAAA TACGGTGGAG AGCTGGAAGA      1200
AAGACAGAAG AAAAGGGCAT AGATAATCCA CATTGGGTGG ACAATCAAAA GCTGACAACA      1260
GGATAGTCTG AAGATGATTC CCTGGCTTGG AATTTCTCAG GATCGCTCTT TCTCTTTCTG      1320
ATACAATATT CAAATATTAA AGTGCTCTGA AAGTCCAGGT TGAAATTACC GCTATAAATT      1380
CAAATTATTT AGGGATCTGC CTGAAATAGT GTGAATGAAG CCTTCCCAAA AGCAGAAACG      1440
                                        Intron 1 ⌐⌐ ⌐Exon II
GGATTTTGAT TCTGGATCTT ATTTTATTGT TCTAGGTTTA CTTGAACTTG AAGGAAAGAA      1500

AAAAAAA ATG TCT CCA CTT CTG AGA AGC ATC TGT GAC ATC ACT GAA ATT        1548
```

FIG. 3C

```
                Met Ser Pro Leu Arg Ser Ile Cys Asp Ile Thr Glu Ile
                 1               5                   10
TTC AAT CAG TAT GTC TCT CAT GAT TGT GAT GGA GCA GCA TTA ACT AAG                    1596
Phe Asn Gln Tyr Val Ser His Asp Cys Asp Gly Ala Ala Leu Thr Lys
 15                  20                  25                  30
                                                          Exon II
AAA GAC CTG AAG AAC CTC CTT GAA AGG GAA TTT GGA GCT GTG CTT CGG                    1644
Lys Asp Leu Lys Asn Leu Leu Glu Arg Glu Phe Gly Ala Val Leu Arg
                 35                  40                  45
 Intron 2
GTAAGAACTA ACAAGAAAAT GAGATCTATT GACTTGAGGC TATGAGATTT ATTCTCAGAG                  1704
GAGACCAGAG CAAGGAATGG TGGTTTTATA TTCATTTTAC ACCACAACAG GTCTACACTA                  1764
CATCCCCCAT TCATTTCTGA GTCAAAAGGT ACTTACTTGA CATTGTAGTC TGAATAATAA                  1824
AGTATTTCAT GTACTTGATG GCATGGCATG TGAATGAGCT CTTCATGGGA CATTACTACA                  1884
AAAGATGTCA AATCACACTA GACTTGGAGG AACTTGGAGG AACTTAAATT TGTTTCCAAA                  1944
TTTCAAAACT GAGATCAGCC TGACTCTATT AATGGTGCT ACCCGTAAAT GTTTTGTTCT                   2004
GTTTTCTAAT ATGGAATAGA AACCAAATCA AGAATACTGG CTGCTTCAGA CAGAAATGGC                  2064
TACTGCAAAT CCTCATAAAT TTCTATTGTA TCTCTCTCAA GGATGAGTTC ATTCTTTCTC                  2124
AATTAAAGCG AACTTGTGTT ATTCTTTCTT GATGTTGAGT AGCTTTGTTA ATTACACAC                   2184
AAGTTCACGA TGCTGTTTTG AATCTTCACC TCAGGCTCTG CTCTAAGGTG CGTAGGCTTA                  2244
CCTGCTATCT ACTTGTGTCT CTCTTCCTGC TTCCTTAGGT TTGATCAGCA CTAAATTACG                  2304
```

FIG. 3D

```
AGATGTAAAA ATTTCAAACG AATATATGCT TTAAAGTGAG GGTTCACATT TTACATGGGG              2364

ACAAAACTTG ATACACACTG GACATTTTC TAATTGCTCT GAATGTCTCT TGAATGTCAG               2424

CATAGCATAA AATATATCAT GTGTGAATAT AATTTTACCA CCTGTAAATA GTGCATTGTA              2484
                                           ┌─Exon III
AAATTTTTGT TTTTCACCAT TTTATAG AGA CCA CAT GAC CCT AAG ACG GTA                  2535
      Intron 2 ┘      Arg Pro His Asp Pro Lys Thr Val
                       1                       5

GAT CTG ATC CTG GAA CTT CTG GAT CGT GAC AGT AAT GGG CGT GTC GAT                2583
Asp Leu Ile Leu Glu Leu Leu Asp Arg Asp Ser Asn Gly Arg Val Asp
            10                      15                      20

TTC AAC GAA TTC CTC CTA TTT ATT TTC AAA GTG GCT CAA GCT TGT TAC                2631
Phe Asn Glu Phe Leu Leu Phe Ile Phe Lys Val Ala Gln Ala Cys Tyr
            25                      30                      35          40

TAT GCT CTC GGC CAG GCC ACG GGA CTG GAT GAG AAG CGA GCC CGG                    2679
Tyr Ala Leu Gly Gln Ala Thr Gly Leu Asp Glu Lys Arg Ala Arg
            45                      50                      55
```

FIG. 3E

```
TGT GAC GGA AAG GAG AGC CTG TTA CAA GAT CGA CGG ACA GAA GAA GAC        2727
Cys Asp Gly Lys Glu Ser Leu Leu Gln Asp Arg Arg Thr Glu Glu Asp
             60                      65                      70

CAA AGG AGA TTC GAG CCC CGG GAC AGA CAA CTG GAA GAA CCT GGG            2775
Gln Arg Arg Phe Glu Pro Arg Asp Arg Gln Leu Glu Glu Pro Gly
         75                      80                      85

CAA CGA CGC AGG CAG AAG AGG CAG GAA CAG GAG AGG GAG CTA GCT GAG        2823
Gln Arg Arg Arg Gln Lys Arg Gln Glu Gln Glu Arg Glu Leu Ala Glu
             90                      95                     100

GGA GAG CAA AGT GAG AAA CAA GAG CGA CTT GAA CAG CGC GAC AGG            2871
Gly Glu Gln Ser Glu Lys Gln Glu Arg Leu Glu Gln Arg Asp Arg
        105                     110                     115                     120

CAG CGC CGC GAC GAG GAG CTG TGG CGG CAA AGG CAA GAA CAG GAA TGG CAA GAA    2919
Gln Arg Arg Asp Glu Glu Leu Trp Arg Gln Arg Gln Glu Trp Gln Glu
             125                     130                     135

CGG GAA GAG CGC GCA GAG GAA CAG CAG CTG CAG AGT TGC AAA GGT            2967
Arg Glu Glu Arg Ala Glu Glu Gln Gln Leu Gln Ser Cys Lys Gly
        140                     145                     150

CAC GAA ACT GAG GAG TTT CCA GAC TTT GAA GAG CAA CTG CGA AGG CGG GAG    3015
His Glu Thr Glu Glu Phe Pro Asp Phe Glu Glu Gln Leu Arg Arg Glu
             155                     160                     165

CTG CTG GAG CTG AGG AGG AAG AGG CGC GAG GAG AAA CAG CAG CAA AGG        3063
Leu Leu Glu Leu Arg Arg Lys Gly Arg Glu Glu Lys Gln Gln Gln Arg
        170                     175                     180
```

FIG. 3F

```
CGA GAG CGC CAA GAC AGA GTG TTC CAG GAG GAA GAA GAG AAA GAG TGG        3111
Arg Glu Arg Gln Asp Arg Val Phe Gln Glu Glu Glu Glu Lys Glu Trp
185                     190                     195                 200

AGG AAG CGC GAG ACA GTG CTC CGG AAG GAA GAG AAG TTG CAG GAA           3159
Arg Lys Arg Glu Thr Val Leu Arg Lys Glu Glu Lys Leu Gln Glu
        205                     210                     215

GAG GAG CCG CAG CGG CAA AGA GAG CTC CAG GAG GAA GAG CAG CTA           3207
Glu Glu Pro Gln Arg Gln Arg Glu Leu Gln Glu Glu Glu Gln Leu
220                     225                     230

CGG AAG CTG GAG CGG CAA GAG CTG AGG GAG CGC CAG GAG GAA GAG           3255
Arg Lys Leu Glu Arg Gln Glu Leu Arg Glu Arg Gln Glu Glu Glu
235                     240                     245

CAG CAG CAA AGG CTG AGG CGC GAG CAG CAA CTA CGC AGG CGC AAG CAG       3303
Gln Gln Gln Arg Leu Arg Arg Glu Gln Gln Leu Arg Arg Lys Gln
250                     255                     260

GAG GAG AGG CGC GAG GAG CAG CAG GAG AGG CGC GAG CAG CAG GAG           3351
Glu Glu Arg Arg Glu Glu Gln Gln Glu Arg Arg Glu Gln Gln Glu
```

FIG. 3G

```
         265                 270                 275                 280
AGG CGC GAG GAG AGG CGC GAG CAG CAG CAG CTG AGG CGC GAG                     3399
Arg Arg Glu Glu Arg Arg Glu Gln Gln Gln Leu Arg Arg Glu
            285                 290                 295

CAG GAG AGG CGC GAG CAG CAG CTG AGG CGC GAG GAG GAG GAG                     3447
Gln Glu Arg Arg Glu Gln Gln Leu Arg Arg Glu Glu Glu Glu
            300                 305                 310

AGG CGC GAG CAG CAG CTG AGG CGC GAG CAG CAG GAG GAG AGG CGC GAG             3495
Arg Arg Glu Gln Gln Leu Arg Arg Glu Gln Gln Glu Glu Arg Arg Glu
            315                 320                 325

CAG CTG AGG CGC GAG CAG CAG CAG CAG CAG CGC GAG CAG CAG CTG                 3543
Gln Leu Arg Arg Glu Gln Gln Gln Gln Gln Arg Glu Gln Gln Leu
            330                 335                 340

AGG CGC GAG CAG CAG CAG CAG CTG AGG CGC GAG CAG CAG                         3591
Arg Arg Glu Gln Gln Gln Gln Leu Arg Arg Glu Gln Gln
            345                 350                 355         360

CAG CTG AGG CGC GAG CAG CAG CAG CAG CTG AGG CGC                             3639
Gln Leu Arg Arg Glu Gln Gln Gln Gln Leu Arg Arg
            365                 370                 375

GAG CAG CAG CTG AGG CGC GAG CAG CAG CGC GAG CAG CTG                         3687
Glu Gln Gln Leu Arg Arg Glu Gln Gln Arg Glu Gln Leu
            380                 385                 390
```

FIG. 3H

```
AGG CGC GAG CAG CAG CTG AGG CGC GAG CAG GAG GAG AGG CAC GAG      3735
Arg Arg Glu Gln Gln Leu Arg Arg Glu Gln Glu Glu Arg His Glu
            395                 400                 405

CAG AAG CAC GAG CAG CGG CTG AAG CGC GAG CAG                      3783
Gln Lys His Glu Gln Arg Leu Lys Arg Glu Gln
    410                 415                 420

GAG GAG AGG CGC GAT TGG CTG AAG CGC GAG CAG GAG ACG GAG AGG CAC GAG      3831
Glu Glu Arg Arg Asp Trp Leu Lys Arg Glu Gln Glu Thr Glu Arg His
425                 430                 435                 440

GAG CAG GAG AGG CGC AAG CAG CTG AAG CTC GAG CAG GAG GAG             3879
Glu Gln Glu Arg Arg Lys Gln Leu Lys Leu Glu Gln Glu Glu
    445                 450                 455

AGG CGC GAA CGT TGG CTG AAG CTC GAG CAG GAG AGG CGC GAG CAG             3927
Arg Arg Glu Arg Trp Leu Lys Leu Glu Gln Glu Arg Arg Glu Gln
        460                 465                 470

CAG GAG AGG CGC GAG CAG CAA CTA AGG CGG GAG CAA GAG CAG GAG AGG CGC GAG AGG      3975
Gln Glu Arg Arg Glu Gln Gln Leu Arg Arg Glu Gln Glu Gln Glu Arg Arg
475                 480                 485
```

FIG. 31

```
GAG CAG CGG CTG AAG CGC CAG GAG GAA GAG AGG CTC CAG CAG CGG      4023
Glu Gln Arg Leu Lys Arg Gln Glu Glu Glu Arg Leu Gln Gln Arg
            490                 495                 500

TTG AGC GAG CAA CAA CTA AGA CGC GAG CAG GAG AGG CTC GAG          4071
Leu Ser Glu Gln Gln Leu Arg Arg Glu Gln Glu Arg Leu Glu
        505                 510                 515      520

CAG CTG CTG AAG CGC GAG GAG AAG AGG CTC GAG CAG GAG CGA          4119
Gln Leu Leu Lys Arg Glu Glu Lys Arg Leu Glu Gln Glu Arg
    525                 530                 535

GAG CAG CGG CTG AAG CGC GAG GAG AGG CGC GAT CAG CTG CTG          4167
Glu Gln Arg Leu Lys Arg Glu Glu Arg Arg Asp Gln Leu Leu
540                 545                 550

AAG CGC GAG GAG AGG CGC CAG CAG CGG CTG AAG CGC GAG CAG GAA      4215
Lys Arg Glu Glu Arg Arg Gln Gln Arg Leu Lys Arg Glu Gln Glu
            555                 560                 565

GAG CAG CTC GAG CAG CGA CTG AAG CGC GAG GAG GTG GAG AGA CTC GAG  4263
Glu Gln Leu Glu Gln Arg Leu Lys Arg Glu Glu Val Glu Arg Leu Glu
        570                 575                 580

CAG GAG AGG CGC AGG GAC GAG CGG CTG AAG CGC GAG CCG GAG GAA      4311
Gln Glu Arg Arg Arg Asp Glu Arg Leu Lys Arg Glu Pro Glu Glu
    585                 590                 595             600

GAG AGG CGC CAC GAG CTG CTG AAG AGC GAG CAG GAG AGG CGC          4359
Glu Arg Arg His Glu Leu Leu Lys Ser Glu Gln Glu Arg Arg
605                 610                 615
```

FIG. 3J

```
CAC GAG CAA CTG AGG CGC GAG CAG CAG GAA AGG CGC GAG CGG CTG    4407
His Glu Gln Leu Arg Arg Glu Gln Gln Glu Arg Arg Glu Arg Leu
        620                 625                 630

AAG CGC GAG GAG GAA GAG AGG CTC GAG CAG CGG CTG AAG CGC GAG    4455
Lys Arg Glu Glu Glu Glu Arg Leu Glu Gln Arg Leu Lys Arg Glu
        635                 640                 645

CAT GAG GAA GAG AGG CGC GAG CAG GAG CTA GCT GAG GAG CAG GAA    4503
His Glu Glu Glu Arg Arg Glu Gln Glu Leu Ala Glu Glu Gln Glu
        650                 655                 660

CAG GCC CGG GAG CGG ATT AAG AGC CGC ATC CCG AAG TGG CAG TGG CAG    4551
Gln Ala Arg Glu Arg Ile Lys Ser Arg Ile Pro Lys Trp Gln Trp Gln
        665                 670                 675                 680

CTA GAA AGC GAG GCC GAC GCA CGG CAA AGC AAA GTC TTA CTC GAG GCC    4599
Leu Glu Ser Glu Ala Asp Ala Arg Gln Ser Lys Val Leu Leu Glu Ala
        685                 690                 695

CCG CAA GCA GGA AGG GCA GAG GCG CCG CAA GAG CAG GAG GAA AAG AGG    4647
Pro Gln Ala Gly Arg Ala Glu Ala Pro Gln Glu Gln Glu Glu Lys Arg
```

FIG. 3K

```
CGG CGC GAG AGT GAG CTG CAA TGG CAG GAG GAA CGG GCT CAC CGG    4695
Arg Arg Glu Ser Glu Leu Gln Trp Gln Glu Glu Arg Ala His Arg
                715                 720                 725

CAG CAG GAA GAG GAG CAG CGC CGG GAC TTC ACA TGG CAG TGG CAG    4743
Gln Gln Glu Glu Glu Gln Arg Arg Asp Phe Thr Trp Gln Trp Gln
        730                 735                 740

GCG GAG GAA AAG AGC GAG AGG GGC CGT CAG AGG CTG TCG GCC AGG CCC 4791
Ala Glu Lys Ser Glu Arg Gly Arg Gln Arg Leu Ser Ala Arg Pro
745                 750                 755                 760

CCA TTG CGG GAG CAG CAG CGG GAG AGG CAG CTG AGG GCC GAG CGC CAG 4839
Pro Leu Arg Glu Gln Gln Arg Glu Arg Gln Leu Arg Ala Glu Arg Gln
        765                 770                 775

CAG CGG GAA CAA CGG TTT CTC CCG GAG GAG GAG AAG GAG CGC CAG     4887
Gln Arg Glu Gln Arg Phe Leu Pro Glu Glu Glu Lys Glu Arg Gln
        780                 785                 790

GGC CGC CAG CGA CGC GAG AGG GAG AAA GAG CTG CAG TTC CTG GAG GAA 4935
Gly Arg Gln Arg Arg Glu Arg Glu Lys Glu Leu Gln Phe Leu Glu Glu
795                 800                 805

GAG GAG CAG CTC CAG CGG CGG GAG CGT GCC CAA CAG CTC CAG GAG GAG 4983
Glu Glu Gln Leu Gln Arg Arg Glu Arg Ala Gln Gln Leu Gln Glu Glu
810                 815                 820
```

FIG. 3L

```
GAG GAC GGC CTC CAG GAG GAT CAG GAG AGG AGG CGA CAG GAG CAG CGC         5031
Glu Asp Gly Leu Gln Glu Asp Gln Glu Arg Arg Arg Gln Glu Gln Arg
825                     830                     835                 840

CGC GAC CAA AAA TGG AGG TGG CAA CTA GAA GAA AGG AAG AGA CGC             5079
Arg Asp Gln Lys Trp Arg Trp Gln Leu Glu Glu Arg Lys Arg Arg
                845                     850                     855

CGC CAC ACG CTG TAC GCC AAG CCA CTA CAA GAG CAG CTG AGG AAG             5127
Arg His Thr Leu Tyr Ala Lys Pro Ala Leu Gln Glu Gln Leu Arg Lys
860                     865                     870

GAA CAG CTG CTG CAG GAG GAG GAG GAG CTA CAG GAG AGA GAG GAG             5175
Glu Gln Leu Leu Gln Glu Glu Glu Glu Leu Gln Glu Arg Glu Glu
        875                     880                     885

CGC GAG AAG AGA AGG CGC CAA GAA CAG GAG AGA CAA TAC CGC GAG GAA         5223
Arg Glu Lys Arg Arg Arg Gln Glu Gln Glu Arg Gln Tyr Arg Glu Glu
        890                     895                     900

GAG CAG CTG CAG CAG GAG GAA CGG GAG GAA CGG GAG                         5271
Glu Gln Leu Gln Gln Glu Glu Glu Glu Leu Leu Arg Leu Arg Glu Glu
905                     910                     915                 920
```

FIG. 3M

```
AAA AGA AGA CGC CAG GAG CGG GAA AGG CAA TAT CGG AAG GAT AAG AAG      5319
Lys Arg Arg Arg Gln Glu Arg Glu Arg Gln Tyr Arg Lys Asp Lys Lys
                925                         930                 935

CTG CAG CAG AAG GAG CAG CTG GGA GAG GAA CCG GAG AAG AGA              5367
Leu Gln Gln Lys Glu Gln Leu Gly Glu Glu Pro Glu Lys Arg
        940                         945                 950

AGG CGC CAG GAG CGG GAG AAA TAC CGC GAG GAA GAG TTG CAG              5415
Arg Arg Gln Glu Arg Glu Lys Tyr Arg Glu Glu Glu Leu Gln
955                         960                         965

CAG GAG GAA GAG CAG CTG CTG AGA GAG GAA CGG GAG AAG AGA AGG CGC      5463
Gln Glu Glu Glu Gln Leu Leu Arg Glu Glu Arg Glu Lys Arg Arg Arg
        970                         975                         980

CAG GAG AGG TGG GAG AGG CAG TAC CGC AAA AAA GAC GAG CTG CAG CAG GAA  5511
Gln Glu Arg Trp Glu Arg Gln Tyr Arg Lys Lys Asp Glu Leu Gln Gln Glu
        985                         990                 995                         1000

GAA GAG CAG CTG CTG AGA GAG GAA CGG GAG AAA AGA CTC CAG GAG          5559
Glu Glu Gln Leu Leu Arg Glu Glu Arg Glu Lys Arg Leu Gln Glu
        1005                        1010                        1015

CGG GAG AGG CAA TAT CGG GAG GAG GAG CTG CAG CAG GAG GAA GAG          5607
Arg Glu Arg Gln Tyr Arg Glu Glu Glu Leu Gln Gln Glu Glu Glu
        1020                        1025                        1030

CAG CTG CTG GGA GAG GAA CGG GAG ACG AGA AGG CGC CAG GAG CTG GAG      5655
Gln Leu Leu Gly Glu Glu Arg Glu Thr Arg Arg Arg Gln Glu Leu Glu
        1035                        1040                        1045
```

FIG. 3N

```
AGG CAA TAT CGG AAG GAA GAG GAG CTG CAG CAG GAG GAA GAG CAG CTG        5703
Arg Gln Tyr Arg Lys Glu Glu Glu Leu Gln Gln Glu Glu Glu Gln Leu
             1050                    1055                    1060

CTG AGA GAG GAA CCG GAG AAG AGA AGG CGC CAG GAG AGG CGG GAG AGG CAA    5751
Leu Arg Glu Glu Pro Glu Lys Arg Arg Arg Gln Glu Arg Arg Glu Arg Gln
         1065                    1070                    1075     1080

TGT CGG GAG GAG GAG CTG CAG CAG GAG GAA GAG CAG CTG CTG AGA            5799
Cys Arg Glu Glu Glu Leu Gln Gln Glu Glu Glu Gln Leu Leu Arg
         1085                    1090                    1095

GAG GAA CGG GAG AAG AGA AGG CGC CAG GAG AGG CTG GAG AGG CAA TAT CGG    5847
Glu Glu Arg Glu Lys Arg Arg Arg Gln Glu Arg Leu Glu Arg Gln Tyr Arg
         1100                    1105                    1110

GAG GAA GAG CTT CAG CGC CAG AAA AGG AAA CAG CGA TAC CGG GAT            5895
Glu Glu Glu Leu Gln Arg Gln Lys Arg Lys Gln Arg Tyr Arg Asp
         1115                    1120                    1125

GAG GAT CAG CGC AGT GAT CTG AAA TGG CAG TGG GAA CCA GAA AAA GAA        5943
Glu Asp Gln Arg Ser Asp Leu Lys Trp Gln Trp Glu Pro Glu Lys Glu
```

FIG. 30

```
AAT GCA GTT CGT GAT AAC AAG GTT TAC TGC AAA GGC AGA GAG AAT GAA      5991
Asn Ala Val Arg Asp Asn Lys Val Tyr Cys Lys Gly Arg Glu Asn Glu
         1145                    1150                    1155                    1160

CAG TTC CGG CAG TTG GAA GAT TCC CAG GTG CGC GAC AGA CAA TCC CAG      6039
Gln Phe Arg Gln Leu Glu Asp Ser Gln Val Arg Asp Arg Gln Ser Gln
         1165                    1170                    1175

CAA GAT CTG CAG CAC CTG GGT GAA CAG CAA GAG AGA GAT CGT GAG          6087
Gln Asp Leu Gln His Leu Gly Glu Gln Gln Glu Arg Asp Arg Glu
         1180                    1185                    1190

CAA GAG AGG CGC TGG CAG CAG GCC AAC AGG CAT TTC CCA GAG GAA          6135
Gln Glu Arg Arg Trp Gln Gln Ala Asn Arg His Phe Pro Glu Glu
         1195                    1200                    1205

GAA CAG CTG GAG CGA GAA GAG CAA AAG GAA GCC AAA AGG CGC GAC AGG      6183
Glu Gln Leu Glu Arg Glu Glu Gln Lys Glu Ala Lys Arg Arg Asp Arg
         1210                    1215                    1220

AAG TCC CAA GAG GAA AAG CAG TTG CTG AGA GAG GAG AAG GAA GAG AAG      6231
Lys Ser Gln Glu Glu Lys Gln Leu Leu Arg Glu Glu Lys Glu Glu Lys
         1225                    1230                    1235                    1240

AGA CGC CGT CAA GAG ACA GAC AGA AAA TTC CGC GAG GAG GAA CAG CTG      6279
Arg Arg Arg Gln Glu Thr Asp Arg Lys Phe Arg Glu Glu Glu Gln Leu
         1245                    1250                    1255

CTC CAG GAA AGG GAG GAA CAG CCG CTG CTC CGC CAA GAG CGT GAC AGA      6327
Leu Gln Glu Arg Glu Glu Gln Pro Leu Leu Arg Gln Glu Arg Asp Arg
         1260                    1265                    1270
```

FIG. 3P

```
AAA TTC CGC GAA GAG GAA CTG CTC CAT CAG GAA CAA GGG AGA AAA TTC        6375
Lys Phe Arg Glu Glu Glu Leu Leu His Gln Glu Gln Gly Arg Lys Phe
                1275                    1280                    1285

CTC GAG GAA CAG CGG CTG CGC GAG GAA CGG GAG GAA AGA TTC CTT            6423
Leu Glu Glu Gln Arg Leu Arg Glu Glu Arg Glu Arg Lys Phe Leu
        1290                    1295                    1300

AAG GAG GAA CAG CAG CTG CGC CTC GAG GAG CGC CAA CTG CGT CAG            6471
Lys Glu Glu Gln Gln Leu Arg Leu Glu Glu Arg Gln Leu Arg Gln
1305                    1310                    1315            1320

GAC CGC GAC AGA AAA TTC CGC GAG GAA CAG CAG CTG AGC CGC CAA            6519
Asp Arg Asp Arg Lys Phe Arg Glu Glu Gln Gln Leu Ser Arg Gln
        1325                    1330                    1335

GAG CGT GAC AGA AAA TTC CGT GAA GAG CAG CAG GTG CGC CGC CAG            6567
Glu Arg Asp Arg Lys Phe Arg Glu Glu Gln Gln Val Arg Arg Gln
        1340                    1345                    1350
```

FIG. 3Q

```
GAA CGA GAG AGA AAA TTC CTG GAG GAG GAA CAG CAG CTG CGC CAG GAG      6615
Glu Arg Glu Arg Lys Phe Leu Glu Glu Glu Gln Gln Leu Arg Gln Glu
            1355                    1360                    1365

CGT CAC AGA AAA TTC CGC GAA GAG GAA CAG CTG CTC CAG GAA AGG GAA      6663
Arg His Arg Lys Phe Arg Glu Glu Glu Gln Leu Leu Gln Glu Arg Glu
            1370                    1375                    1380

GAA CAG CAG CTG CAC CGC CAA GAG CGT GAC AGA AAA TTC CTG GAG GAG      6711
Glu Gln Gln Leu His Arg Gln Glu Arg Asp Arg Lys Phe Leu Glu Glu
            1385                    1390                    1395            1400

GAA CAA CAG CTG CGC CGC CAA GAG CGT GAC AGA AAA TTC CGC GAA CAG      6759
Glu Gln Gln Leu Arg Arg Gln Glu Arg Asp Arg Lys Phe Arg Glu Gln
            1405                    1410                    1415

GAA CTG CGC AGT CAG GAA CCA GAG AGA AAA TTC CTC GAG GAG GAA CAG      6807
Glu Leu Arg Ser Gln Glu Pro Glu Arg Lys Phe Leu Glu Glu Glu Gln
            1420                    1425                    1430

CAG CTG CAC CGC CAG CAA CGG CAG GAG AAA TTC CTC CAG GAG GAA CAG      6855
Gln Leu His Arg Gln Gln Arg Gln Glu Lys Phe Leu Gln Glu Glu Gln
            1435                    1440                    1445

CAG CTG CGC CGC CAG GAG CGC GGG CAA CAG CGG CGT CAG GAC CGT GAC      6903
Gln Leu Arg Arg Gln Glu Arg Gly Gln Gln Arg Arg Gln Asp Arg Asp
            1450                    1455                    1460

AGA AAA TTC CGC GAG GAG GAA CAG CTG CGC CAG GAG AGG GAG GAA CAG      6951
Arg Lys Phe Arg Glu Glu Glu Gln Leu Arg Gln Glu Arg Glu Glu Gln
            1465                    1470                    1475            1480
```

FIG. 3R

```
CAG CTG AGC CGC CAA GAG CGT GAC AGA AAA TTC CGT TTA GAG GAA CAG      6999
Gln Leu Ser Arg Gln Glu Arg Asp Arg Lys Phe Arg Leu Glu Glu Gln
            1485                    1490                    1495

AAA GTG CGC CGC CAG GAA CAA GAG AGA AAA TTC ATG GAG GAC GAA CAG      7047
Lys Val Arg Arg Gln Glu Gln Glu Arg Lys Phe Met Glu Asp Glu Gln
            1500                    1505                    1510

CAG CTG CGC CAG GAG GGC CAA CAG CTG CGC CAG GAG GAC AGA              7095
Gln Leu Arg Gln Glu Gly Gln Gln Leu Arg Gln Glu Asp Arg
            1515                    1520                    1525

AAA TTC CGC GAA GAC GAA CAG CTG CTC CAG GAA AGG GAA CAG CAG          7143
Lys Phe Arg Glu Asp Glu Gln Leu Leu Gln Glu Arg Glu Gln Gln
            1530                    1535                    1540

CTG CAC CGC CAA GAG CGT GAC AGA AAA TTC CTC GAG GAA CCG CAG          7191
Leu His Arg Gln Glu Arg Asp Arg Lys Phe Leu Glu Glu Pro Gln
            1545                    1550                    1555                    1560

CTG CGC CAG GAG CGC GAA CAA CAG CTG CGT CAC GAC CGC GAC AGA          7239
Leu Arg Arg Gln Glu Arg Glu Gln Gln Leu Arg His Asp Arg Asp Arg
```

FIG. 3S

```
                    1565                    1570                    1575
AAA TTC CGT GAA GAG GAA CAG CTG CTC CAG GAA GGG GAG GAA CAG CAG       7287
Lys Phe Arg Glu Glu Glu Gln Leu Leu Gln Glu Gly Glu Glu Gln Gln
                    1580                              1585            1590

CTG CGC CGC CAA GAG CGT GAC AGA AAA TTC CGC GAA GAG GAA CAG CAG       7335
Leu Arg Arg Gln Glu Arg Asp Arg Lys Phe Arg Glu Glu Glu Gln Gln
               1595                              1600                          1605

CTC CGC CGT CAG GAA CGA GAG AAA TTC CTC CAG GAG GAG CAG CAG           7383
Leu Arg Arg Gln Glu Arg Glu Lys Phe Leu Gln Glu Glu Gln Gln
          1610                              1615                          1620

CTG CGC CGC CAG GAA CTG GAG AGA AAA TTC CGT GAG GAG GAA CAG CTG       7431
Leu Arg Arg Gln Glu Leu Glu Arg Lys Phe Arg Glu Glu Glu Gln Leu
          1625                              1630                               1635                    1640

CGC CAA GAA ACG GAG CAA GAG CAG CTG CGC CGC CAA GAA CGC TAC AGA       7479
Arg Gln Glu Thr Glu Gln Glu Gln Leu Arg Arg Gln Glu Arg Tyr Arg
          1645                              1650                               1655

AAA ATC CTA GAG GAG CAG CTC CGT CCG GAA AGG GAA GAA CAG CAG           7527
Lys Ile Leu Glu Glu Gln Leu Arg Pro Glu Arg Glu Glu Gln Gln
          1660                              1665                               1670

CTG CGC CGC CAG GAG CGC GAC AGA AAA TTC CGC GAG GAG GAA CAG CTC       7575
Leu Arg Arg Gln Glu Arg Asp Arg Lys Phe Arg Glu Glu Glu Gln Leu
          1675                              1680                               1685
```

FIG. 3T

```
CGC CAG GGA AGG GAG GAA CAG CAG CTG CGC CGC AGC CAA GAG TCT GAC AGA    7623
Arg Gln Gly Arg Glu Glu Gln Gln Leu Arg Arg Ser Gln Glu Ser Asp Arg
         1690                    1695                    1700

AAA TTC CGC GAG GAG GAA CAG CTA CGC CAG GAG AGG GAA CAG CAG            7671
Lys Phe Arg Glu Glu Glu Gln Leu Arg Gln Glu Arg Glu Gln Gln
         1705                    1710                    1715      1720

CTG CGC CCC CAA CAG CGT GAC GGA AAG TAT CGC TGG GAA GAG CAG            7719
Leu Arg Pro Gln Gln Arg Asp Gly Lys Tyr Arg Trp Glu Glu Gln
         1725                    1730                    1735

CTC CAA CTT GAG GAA CAA GAG CAG AGG CTG CGG CAG GAG CGA GAC CGG        7767
Leu Gln Leu Glu Glu Gln Glu Gln Arg Leu Arg Gln Glu Arg Asp Arg
         1740                    1745                    1750

CAG TAC CGG GAG GAG CAG TTT GCC ACG CAG GAG AAG AGT CGT CGT            7815
Gln Tyr Arg Glu Glu Gln Phe Ala Thr Gln Glu Lys Ser Arg Arg
         1755                    1760                    1765

GAG GAA CAA GAA CTA TGG CAA GAG GAG CAG AAA CGT CGC CAG GAA            7863
Glu Glu Gln Glu Leu Trp Gln Glu Glu Gln Lys Arg Arg Gln Glu
         1770                    1775                    1780
```

FIG. 3U

```
CGG GAA AGG AAA TTA CGG GAA GAA CAC ATC CGC CGC CAG CAG AAG GAG     7911
Arg Glu Arg Lys Leu Arg Glu Glu His Ile Arg Arg Gln Gln Lys Glu
1785                    1790                    1795            1800

GAA CAG AGG CAC CGC CAA GTC GGG GAG ATA CAA TCC CAA GAA GGG AAG     7959
Glu Gln Arg His Arg Gln Val Gly Glu Ile Gln Ser Gln Glu Gly Lys
            1805                    1810                    1815

GGC CAT GGG CGG CTT CTG GAG CCC GGC ACT CAT CAG TTT GCC AGT GTC     8007
Gly His Gly Arg Leu Leu Glu Pro Gly Thr His Gln Phe Ala Ser Val
        1820                    1825                    1830

CCA GTG CGC TCC AGC CCT CTC TAT GAG TAC ATC CAA GAG CAG AGA TCT     8055
Pro Val Arg Ser Ser Pro Leu Tyr Glu Tyr Ile Gln Glu Gln Arg Ser
    1835                    1840                    1845

CAA TAC CGC CCT TAAGTGATGT TGCCAATATC TTGACACCTG CCAAAGCTTC         8107
Gln Tyr Arg Pro
1850

CAGCACGGGA AAATGAGAAA CACTGGGTAC CAAGTGATAA CTCAGATGTT TCTGGTTGTG   8167

GGAAAACTCT CTGATATTAG AATGTCTTTT CTTCCAAAAT CTTAAACTAC GCTCATTTTA   8227

CGCACTTTGT ACTTCTGCTT TTTATTCTTC CTCAAGTAGT TCTTTACTGC AAGATGTCTT   8287

TCTTTTGCTC TTTGATGCAG ATGTGGTGTG CATTTAAAAA AAATATAAAT CATTTAATTT   8347

GTTTAAGAAA TTTTGTTTGA GGAACATGTT CATTTATTGC TTTCAGAAGT AACAAGAGTA   8407

ATAGGATGAT TTGAGATTCT AAACAATGGG TCGGTTTGTT TAATGACTGA CCCATCTTGT   8467
```

FIG.3V

```
GGAAAGTGCA GATACTTTTA ATGTTCAAGT TGCTATTTCT TCTTGAACCT AAATTGATCA    8527

TTGCCTCCAA ACAGCATTTC ATCCTTTTGT GGCATAGTTA GCACAAATTC CAGGTAACTA    8587

AATTTTTATA ACCCTTGAAT AGTGCAGGGG GAGTGACCTC TGCATAAAAA CTTCCTGTAA    8647

AATCAGCCCA TTACTGGAAG AAATATCTGT TAAGAATAGG TTTAGCTTTG AAGATTTAGA    8707

ATTTAAATTA GATTTTTTTT AAACTCAACT CCACTTAAAC ACATAATCTC ATGAAGAAAT    8767

AATGAGGTAT TTAGAATTTA AATGAGTTCA AATTTTAAAA CTGTGTCTGT TGTAGTCTAT    8827

AGTGTTCATT CTACTTCCCC AAGTTTTGAT GAGTTTCAGA ATATTATGAA CCTTTGTTAA    8887

TTTTAGCTTG TTAGAAGGAA GCTGCTCAGA ATCCCATAAA CATCTGTCTT ACTCTAGGGC    8947

CAATAAGAGA TCACATAGAG CATGTTGGGG GTGTAAAAGG GAAAAATGTG TGAACATAGG    9007

GGCAAATTTC TAGAGGCCCT TTGACAAGAC CCATTTGCCC ACAATCATTT GAGGCCTATT    9067

GATAATACCT TAGATATATT CTTGTTGAAA TAATTGGACT GTGAAAAATT AAT<u>AATAAAT</u>    9127
```

FIG. 3W

```
GTTTGGCAAG TAACTACTTT TGTCTGTTTT AACTCTGCGT CAATCATAAC AAGATCTCAT    9187
TGTCTGGAAA CTAACACAAG TTCCCAATCA CATAAGGGCA TTTTGTTACT TATCTATGTC    9247
CAAATACGAA AAAAGAGGGG AGAGAATTCT TTGTTTTTCC CCAACCTTTT TTTTTTTTT     9307
TTTTTTTTTT TTTTGCAGTT AGGCTGAACT CTATTCCAT CCCCACACTG AGATTGCCTT     9367
CCAGAGTGTT TTTGTTCTTG ACCCACAGCT TTCTATGCCA TTCTTGCAGC GACTCACTGG    9427
TCATGACAAA TACTGGTGCT CCCAATATTT GTTAATATTT CCTTTAGAGA ATGCAGCAGC    9487
TTCTTCGTCT CTGATGTCTG ATGAGCCCAAT GATAGAAAAT GGCCTGAAAC TTCAGATCCT   9547
CGAG                                                                  9551
```

FIG. 8

GEL ELECTROPHORESIS 220-
200-

1  2  3

DOT BLOTS WITH ⁴⁵CaCl₂

| Sample | Relative incorporation | Molar ratio |
|---|---|---|
| total mouse epidermal extract | 432 | * |
| mouse filaggrin | 0 | 0 |
| mouse profilaggrin | 276 | 1.35 |
| mouse keratin 10 | 0 | 0 |
| human calmodulin | 1022 | 1.00 |
| human troponin | 402 | 0.73 |
| pig trichohyalin | 241 | 0.98 |
| bovine serum albumin | 32 | 0.06 |
| hen egg lysozyme | 67 | 0.04 |

FIG. 11A

```
CCTTTAGAGG AGCCTGAGAA GAGGCAGAGG AAGGGCGAAA C ATG GCT GCT CTA            53
                                              Met Ala Ala Leu            4

GGA GTC CAG AGT ATC AAC TGG CAG AAG GCC TTC AAC CGA CAA GCG CAT         101
Gly Val Gln Ser Ile Asn Trp Gln Lys Ala Phe Asn Arg Gln Ala His          20

CAC ACA GAC AAG TTC TCC AGC CAG GAG CTC ATC TTG CGG AGA GGC CAA         149
His Thr Asp Lys Phe Ser Ser Gln Glu Leu Ile Leu Arg Arg Gly Gln          36

AAC TTC CAG GTC TTA ATG ATC ATG AAC AAA GGC CTT GGC TCT AAC GAA         197
Asn Phe Gln Val Leu Met Ile Met Asn Lys Gly Leu Gly Ser Asn Glu          52

AGA CTG GAG TTC ATT GAC ACC ACA GGG CCT TAC CCC TCA GAG TCG GCC         245
Arg Leu Glu Phe Ile Asp Thr Thr Gly Pro Tyr Pro Ser Glu Ser Ala          68

ATG ACG AAG GCT GTG TTT CCA CTC TCC AAT GGC AGT AGT GGT GGC TGG         293
Met Thr Lys Ala Val Phe Pro Leu Ser Asn Gly Ser Ser Gly Gly Trp          84

AGT GCG GTG CTT CAG GCC AGC GCC AAT ACT CTG ACT ATC AGC ATC             341
Ser Ala Val Leu Gln Ala Ser Ala Asn Thr Leu Thr Ile Ser Ile            100

TCC AGT CCT GCC AGC GCA CCC ATA GGA CGG TAC ACA ATG GCC CTC CAG         389
Ser Ser Pro Ala Ser Ala Pro Ile Gly Arg Tyr Thr Met Ala Leu Gln        116

ATC TTC TCC CAG GGC GGC ATC TCC TCT GTG AAA CTT GGG ACG TTC ATA         437
Ile Phe Ser Gln Gly Gly Ile Ser Ser Val Lys Leu Gly Thr Phe Ile        132
```

FIG. 11B

```
CTG CTT TTT AAC CCC TGG CTG AAT GTG GAT AGC GTC TTT ATG GGT AAC    485
Leu Leu Phe Asn Pro Trp Leu Asn Val Asp Ser Val Phe Met Gly Asn    148

CAT GCT GAG AGA GAA GAG TAT GTT CAG GAA GAT GCC GGC ATC ATC TTT    533
His Ala Glu Arg Glu Glu Tyr Val Gln Glu Asp Ala Gly Ile Ile Phe    164

GTG GGA AGC ACA AAC CGA ATT GGC ATG ATT GGC ATG TGG AAC TTT GGA CAG    581
Val Gly Ser Thr Asn Arg Ile Gly Met Ile Gly Trp Asn Phe Gly Gln    180

TTT GAA GAC ATT CTC AGC ATC TGC CTC TCA ATC TTG GAT AGG AGT    629
Phe Glu Asp Ile Leu Ser Ile Cys Leu Ser Ile Leu Asp Arg Ser    196

CTG AAT TTC CGC CGT GAC GCT GCT ACT GAT GTG GCC AGC AGA AAT GAC    677
Leu Asn Phe Arg Arg Asp Ala Ala Thr Asp Val Ala Ser Arg Asn Asp    212

CCC AAA TAC GTT GGC CGG GTG CTG AGT GCC ATG ATC AAT AGC AAT GAT    725
Pro Lys Tyr Val Gly Arg Val Leu Ser Ala Met Ile Asn Ser Asn Asp    228

GAC AAT GGT GTG CTT GCT GGG AAT TGG AGC GGC ACT TAC ACC GGT GGC    773
Asp Asn Gly Val Leu Ala Gly Asn Trp Ser Gly Thr Tyr Thr Gly Gly    244

CGG GAC CCA AGG AGC TGG GAC GGC AGC GTG GAG ATC CTC AAA AAT TGG    821
Arg Asp Pro Arg Ser Trp Asp Gly Ser Val Glu Ile Leu Lys Asn Trp    260

AAA AAA TCT GGC TTC AGC CCA GTC CGA TAT GGC CAG TGC TGG GTC TTT    869
```

FIG. 11C

```
Lys Lys Ser Gly Phe Ser Pro Val Arg Tyr Gly Gln Cys Trp Val Phe              276

GCT GGG ACC AAC CTC ACA GCG CTG CGG TCT TTG GGG ATT CCT TCC CGG              917
Ala Gly Thr Asn Leu Thr Ala Leu Arg Ser Leu Gly Ile Pro Ser Arg              292

GTG ATC ACC AAC TTC AAC TCA GCT CAT GAC ACA GAC CGA AAT CTC AGT              965
Val Ile Thr Asn Phe Asn Ser Ala His Asp Thr Asp Arg Asn Leu Ser              308

GTG GAT GTG TAC TAC GAC CCC ATG GGA AAC CCC CTG GAC AAG GGT AGT             1013
Val Asp Val Tyr Tyr Asp Pro Met Gly Asn Pro Leu Asp Lys Gly Ser              324

GAT AGC GTA TGG AAT TTC CAT GTC AAT GAA GGC TGG TTT GTG AGG                 1061
Asp Ser Val Trp Asn Phe His Val Asn Glu Gly Trp Phe Val Arg                  340

TCT GAC CTG GGC CCC CCG TAC GGT GGA CAG GTG TTG GAT GCT ACC                 1109
Ser Asp Leu Gly Pro Pro Tyr Gly Gly Gln Val Leu Asp Ala Thr                  356

CCG CAG GAA AGA AGC CAA GTG TTC CAG TGC GGC CCC GCT TCG GTC                 1157
Pro Gln Glu Arg Ser Gln Val Phe Gln Cys Gly Pro Ala Ser Val                  372

ATT GGT GTT CGA GAG GGT GAT GTG CAG CTG AAC TTC GAC ATG CCC TTT             1205
Ile Gly Val Arg Glu Gly Asp Val Gln Leu Asn Phe Asp Met Pro Phe              388

ATC TTC GCG GAG GTT AAT GCC GAC CGC ATC ACC TGG CTG TAC GAC AAC             1253
Ile Phe Ala Glu Val Asn Ala Asp Arg Ile Thr Trp Leu Tyr Asp Asn              444

ACC ACT GGC AAA CAG TGG AAG AAT TCC GTG AAC AGT CAC ACC ATT GGC             1301
Thr Thr Gly Lys Gln Trp Lys Asn Ser Val Asn Ser His Thr Ile Gly              420
```

FIG. 11D

```
AGG TAC ATC AGC ACC AAG GCG GTG GGC AAT GCT CGC ATG GAC GTC       1349
Arg Tyr Ile Ser Thr Lys Ala Val Gly Ser Asn Ala Arg Met Asp Val    436

ACG GAC AAG TAC AAG TAC CCA GAA GGC TCT GAC CAG GAA AGA CAA GTG   1397
Thr Asp Lys Tyr Lys Tyr Pro Glu Gly Ser Asp Gln Glu Arg Gln Val    452

TTC CAA AAG GCT TTG GGG AAA CTT AAA CCC AAC ACG CCA TTT GCC GCG   1445
Phe Gln Lys Ala Leu Gly Lys Leu Lys Pro Asn Thr Pro Phe Ala Ala    468

ACG TCT TCG ATG GGT TTG GAA ACA GAG CAG CCC AGC ATC ATC          1493
Thr Ser Ser Met Gly Leu Glu Thr Glu Gln Glu Pro Ser Ile Ile        484

GGG AAG CTG AAG GTC GCT GGC ATG CTG GCA GTA GGC AAA GAA GTC AAC   1541
Gly Lys Leu Lys Val Ala Gly Met Leu Ala Val Gly Lys Glu Val Asn    500

CTG GTC CTA CTG CTC AAA AAC CTG AGC AGG GAT ACG AAG ACA GTG ACA   1589
Leu Val Leu Leu Leu Lys Asn Leu Ser Arg Asp Thr Lys Thr Val Thr    516

GTG AAC ATG ACA GCC TGG ACC ATC ATC TAC AAC GGC ACG CTT GTA CAT   1637
Val Asn Met Thr Ala Trp Thr Ile Ile Tyr Asn Gly Thr Leu Val His    532

GAA GTG TGG AAG GAC TCT GCC ACA ATG TCC CTG GAC CCT GAG GAA GAG   1685
Glu Val Trp Lys Asp Ser Ala Thr Met Ser Leu Asp Pro Glu Glu Glu    548

GCA GAA CAT CCC ATA AAG ATC TCG TAC GCT CAG TAT GAG AGG TAC CTG   1733
```

FIG. 11E

```
                                                                          564
Ala Glu His Pro Ile Lys Ile Ser Tyr Ala Gln Tyr Glu Arg Tyr Leu

AAG TCA GAC AAC ATG ATC CGG ATC ACA GCG GTG TGC AAG GTC CCA GAT          1781
Lys Ser Asp Asn Met Ile Arg Ile Thr Ala Val Cys Lys Val Pro Asp           580

GAG TCT GAG GTG GTG GTG GAG CGG GAC ATC ATC CTG GAC AAC CCC ACC          1829
Glu Ser Glu Val Val Val Glu Arg Asp Ile Ile Leu Asp Asn Pro Thr           596

TTG ACC CTG GAG GTG CTG AAC GAG GCT CGT GTG CGG AAG CCT GTG AAC          1877
Leu Thr Leu Glu Val Leu Asn Glu Ala Arg Val Arg Lys Pro Val Asn           612

GTG CAG ATG CTC TTC TCC AAT CCA CTG GAT GAG CCG GTG AGG GAC TGC          1925
Val Gln Met Leu Phe Ser Asn Pro Leu Asp Glu Pro Val Arg Asp Cys           628

GTG CTG ATG GAG GGA AGC GGC CTG CTG CTG GGT AAC CTG AAG CTG ATC          1973
Val Leu Met Glu Gly Ser Gly Leu Leu Leu Gly Asn Leu Lys Leu Ile           644

GAC GTG CCG ACC CTA GGG CCC AAG GAG CGG TCC CGG GTC CGT TTT GAT          2021
Asp Val Pro Thr Leu Gly Pro Lys Glu Arg Ser Arg Val Arg Phe Asp           660

ATC CTG CCC TCC CGG AGT GGC ACC CAA CTG CTC GCC GAC TTC TCC              2069
Ile Leu Pro Ser Arg Ser Gly Thr Lys Gln Leu Leu Ala Asp Phe Ser           676

TGC AAC AAG TTC CCT GCA ATC AAG GCC ATG TTG TCC ATC GAC GTA GCC          2117
Cys Asn Lys Phe Pro Ala Ile Lys Ala Met Leu Ser Ile Asp Val Ala           692

GAA TGAAGGGCGC TGGTGGCCTC CCGTACAAAC TTGGACAACA CGGAGCAGGG               2170
Glu                                                                       693
```

FIG. 11F

```
AGAGCTCACC ATGGAATGAA CCCCCCGCCC ATGCTGTCCG GCCTGGGAAA CCCTCTCCAT    2230
CTCCCAAGGC TGCCAGACAT GGACTCCGGG CTCCAGCACA TCCCCCTCTC CTCTCCCCCA    2290
GGTTGGGGCT GGGTCCACCC TGTCCTATGA CTTGATCACT TTTGCACATT CCCTGGCCGT    2350
TTCTCCCCAG AGCTGCCTGC TCTGTGAGCC CCACAGCCCT GCTCATTCCT CACGCCCTTC    2410
AATGCTGCAG GATGGACTGG CCCCTGACCC AGGGACTCTC CAAACGGGAT ACAGGAGAGA    2470
AGCTGGTCTA GACTGTTTGC TGATCCCCAA CCTGCACGGG GCATTCCTGC TTCTCTCTCA    2530
GGCCACCACA GAGGGCAGGG GATGGTTAGT CACCTGCCCC AGCACTCACA CCCTAACTCA    2590
AAATAAATGT TAAATAAGTG CGATCACACA                                     2620
```

FIG. 11G

```
                ACACCATCTC TGTCATTCCC AGAGGAGCCC CAGGAAAGGC AGAAGAAGCT GACC ATG    57
                                                                         Met   1

AGT GCT TTA CAG ATC CAA AAC GTC AAC TGG CAG GTG CCT ATG AAT CGA              105
Ser Ala Leu Gln Ile Gln Asn Val Asn Trp Gln Val Pro Met Asn Arg               17

AGG GCG CAT CAC ACA GAC AAG TTC TCC AGC CAG GAT TCT ATT GTG CGG              153
Arg Ala His His Thr Asp Lys Phe Ser Ser Gln Asp Ser Ile Val Arg               33

AGA GGA CAG CCC TGG GAG ATA TTA GTC TGC AAC CGA AGT CTT GAG                  201
Arg Gly Gln Pro Trp Glu Ile Leu Val Cys Asn Arg Ser Leu Glu                   49

TCT GGA GAA GAT CTG AAT TTC ATT GTT TCC ACA GGT CCC CAA CCC TCT              249
Ser Gly Glu Asp Leu Asn Phe Ile Val Ser Thr Gly Pro Gln Pro Ser               65

GAG TCA GCC AGG ACA AAG GCT GTG TTT TCC ATC TCT GGG AGA AGC ACG              297
Glu Ser Ala Arg Thr Lys Ala Val Phe Ser Ile Ser Gly Arg Ser Thr               81

GGT GGC TGG AAT GCA GCG CTC AAA AGC AGT GGC AAT AAT CTG GCC                  345
Gly Gly Trp Asn Ala Ala Leu Lys Ser Ser Gly Asn Asn Leu Ala                   97

ATT GCT ATT GCC AGT CCT GTC AGT GCT CCC ATC GGA TTG TAC ACA CTG              393
Ile Ala Ile Ala Ser Pro Val Ser Ala Pro Ile Gly Leu Tyr Thr Leu              113

AGT GTT GAG ATC ATG CTC TCC AGG GCC AGG TCC TCT CTG AAA CTT GGC              441
Ser Val Glu Ile Met Leu Ser Arg Ala Arg Ser Ser Leu Lys Leu Gly              129

ACG TTT ATA ATG CTC TTC AAC CCG TGG TTG CAA GCG GAT GAT GTC TTT              489
Thr Phe Ile Met Leu Phe Asn Pro Trp Leu Gln Ala Asp Asp Val Phe              145
```

FIG. 11H

```
ATG AGT AAC CAC GCC GAA AGA CAA GAG TAT GTT GAA GAA GAT TCT GGC
Met Ser Asn His Ala Glu Arg Gln Glu Tyr Val Glu Glu Asp Ser Gly     537
                                                                    161

ATC ATC TAT GTG GGC AGC ACA AAT CGA ATT GGC ATG GTT GGC TGG AAC
Ile Ile Tyr Val Gly Ser Thr Asn Arg Ile Gly Met Val Gly Trp Asn     585
                                                                    177

TTT GGA CAG TTT GAA GAA GAC ATT CTG AAC ATC TCC CTC ATT TTG
Phe Gly Gln Phe Glu Glu Asp Ile Leu Asn Ile Ser Leu Ser Ile Leu     633
                                                                    193

GAT AGG AGT CTG AAT TTC CGT CGT GAC CCT GTG ACT GAT GTG GCT CGC
Asp Arg Ser Leu Asn Phe Arg Arg Asp Pro Val Thr Asp Val Ala Arg     681
                                                                    209

AGA AAT GAC CCC AAA TAT GTG TGC CGG GTG CTG AGT GCC ATG ATT AAT
Arg Asn Asp Pro Lys Tyr Val Cys Arg Val Leu Ser Ala Met Ile Asn     729
                                                                    225

GGC AAT GAT GAT AAC GGT GTG ATT TCT GGG AAC TGG AGT GGT AAT TAC
Gly Asn Asp Asp Asn Gly Val Ile Ser Gly Asn Trp Ser Gly Asn Tyr     777
                                                                    241

ACC GGT GGT GTG GAC CCA AGG ACC TGG AAT GGT AGT GTG GAG ATC CTC
Thr Gly Gly Val Asp Pro Arg Thr Trp Asn Gly Ser Val Glu Ile Leu    825
                                                                    257

AAG AAC TGG AAA AAA TCT GGC TTC AGG CCA GTC CAA TTT GGC CAG TGC
Lys Asn Trp Lys Lys Ser Gly Phe Arg Pro Val Gln Phe Gly Gln Cys    873
                                                                    273
```

FIG. 11I

```
TGG GTC TTT GCT GGA ACC CTC AAC ACA GTG CTG CGG TGC TTG GGG GTT      921
Trp Val Phe Ala Gly Thr Leu Asn Thr Val Leu Arg Cys Leu Gly Val      289

CGC TCT CGG GTG ATC ACC AAC TTC AAC TCG GCT CAC GAC ACA GAT CGA      969
Arg Ser Arg Val Ile Thr Asn Phe Asn Ser Ala His Asp Thr Asp Arg      305

AAC CTC AGT GTG GAT GTG TAC TAC GAT GTT TAT GAT GCC ATG GGA AAT CCC CTG GAG     1017
Asn Leu Ser Val Asp Val Tyr Tyr Asp Val Tyr Asp Ala Met Gly Asn Pro Leu Glu      321

AAA GGA AGT GAT AGC AGT GTG TGG AAT TTT CAC GTC TGG AAT GAA GGC TGG     1065
Lys Gly Ser Asp Ser Val Trp Asn Phe His Val Trp Asn Glu Gly Trp      337

TTC GTG CGG ACT GAC CTA GGC CCC ACA TAC AAT GGA TGG CAG GTG CTG     1113
Phe Val Arg Thr Asp Leu Gly Pro Thr Tyr Asn Gly Trp Gln Val Leu      353

GAT GCC ACC CCC CAG GAG AGA AGC CAA GGC GTA TTC CAG TGC GGT CCA     1161
Asp Ala Thr Pro Gln Glu Arg Ser Gln Gly Val Phe Gln Cys Gly Pro      369

GCT TCC GTT AAT GCA ATC AAA GCC GGT GAT GTG GAC CGG AAT TTT GAC     1209
Ala Ser Val Asn Ala Ile Lys Ala Gly Asp Val Asp Arg Asn Phe Asp      385

ATG ATC TTC ATC GCG GAG GTT AAT GCA GAT CGC ATC ACT TGG ATC     1257
Met Ile Phe Ile Ala Glu Val Asn Ala Asp Arg Ile Thr Trp Ile      401

TAT AAT AGA AAT AAC ACC CAG AAG CAG AAT TCT GTG GAC ACT CAC     1305
Tyr Asn Arg Asn Asn Thr Gln Lys Gln Asn Ser Val Asp Thr His      417

TCC ATT GGC AAA TAC ATC AGC ACC AAG GCA GTA GGC AGC AAC TCT CGC     1353
Ser Ile Gly Lys Tyr Ile Ser Thr Lys Ala Val Gly Ser Asn Ser Arg      433

ATG GAT GTC ACA GAC TAC AAG TAT CCA GAA GGT TCC AGT GAG GAA     1401
Met Asp Val Thr Asp Tyr Lys Tyr Pro Glu Gly Ser Ser Glu Glu      449
```

FIG. 11J

```
AGA CAA GTG CAC CAA AAG GCT TTG GAC AAA CTC AAA CCT AAC GCA TCT    1449
Arg Gln Val His Gln Lys Ala Leu Asp Lys Leu Lys Pro Asn Ala Ser     465

TTT GGC GCA ACA TCT TCG AGG AAT CCA GAA GGG GAA GAC AAG GAG CCC    1497
Phe Gly Ala Thr Ser Ser Arg Asn Pro Glu Gly Glu Asp Lys Glu Pro     481

AGC ATT TCT GGG AAG TTC AAG GTC ACG GGC ATA CTG GCA GTA GGC AAA    1545
Ser Ile Ser Gly Lys Phe Lys Val Thr Gly Ile Leu Ala Val Gly Lys     497

GAA GTC AGT CTG TCC ATG CTG CTC AAA AAC ACT AAT GAC AGG AAG         1593
Glu Val Ser Leu Ser Met Leu Leu Lys Asn Thr Asn Asp Arg Lys         513

ACA GTG ACG ATG AAC ACA GCC TGG ACC ATC GTC TAC AAT GGT ACC        1641
Thr Val Thr Met Asn Thr Ala Trp Thr Ile Val Tyr Asn Gly Thr         529

CTT GTC CAC GAA GTG TGG AAG GAC TCA GCC ACA ATA TCC TTG GAT CCT    1689
Leu Val His Glu Val Trp Lys Asp Ser Ala Thr Ile Ser Leu Asp Pro     545

GAA GAA ATA CAG TAT CCT GTG AAG ATC GCA TAC TCT CAG TAT GAG        1737
Glu Glu Ile Gln Tyr Pro Val Lys Ile Ala Tyr Ser Gln Tyr Glu         561
```

FIG. IIK

```
AGA TAC CTG AAG GCA GAC AAC ATG ATC CGG ATC TCA GCC GTT TGC AAG    1785
Arg Tyr Leu Lys Ala Asp Asn Met Ile Arg Ile Ser Ala Val Cys Lys     577

GTG CCC GAT GAG GCT GAG GTG GTG GAA TGG GAT GTC ATC CTG GAT        1833
Val Pro Asp Glu Ala Glu Val Val Glu Trp Asp Val Ile Leu Asp        593

AAT CCT GCT TTG ACC CTG GAG GTG CTG GAA CAG GCT CAT GTG CGG AAG    1881
Asn Pro Ala Leu Thr Leu Glu Val Leu Glu Gln Ala His Val Arg Lys    609

CCC GTG AAC GTG CAG ATG ATT TTC TCC AAC CCC CTG GAC CAG CCG GTG    1929
Pro Val Asn Val Gln Met Ile Phe Ser Asn Pro Leu Asp Gln Pro Val    625

AGG AAC TGC GTG CTG GTG CTG GAG GGC AGC GGC TGC TCG GTG GCA GCC    1977
Arg Asn Cys Val Leu Val Leu Glu Gly Ser Gly Cys Ser Val Ala Ala    641

TCA AGA TTG ATG TGC CAT CCC TGC GTC CCC AAG GAG AAG TCC CGC ATC    2025
Ser Arg Leu Met Cys His Pro Cys Val Pro Lys Glu Lys Ser Arg Ile    657

CGA TTT GAG ATT TTC CCC ACT CGG AGT GGC ACC AAG CAA CTG CTC GCT    2073
Arg Phe Glu Ile Phe Pro Thr Arg Ser Gly Thr Lys Gln Leu Leu Ala    673

GAC TTT TCC TGC AAT AAA TTC CCT ACT ATC AAG GCC ATG CTG CCC ATT    2121
Asp Phe Ser Cys Asn Lys Phe Pro Thr Ile Lys Ala Met Leu Pro Ile    689

GAT GTC TCT GAG TGACCGACCC AGCAGCACTC CCACAGAGCT CGGTGACACA        2173
Asp Val Ser Glu                                                     693

GACCAGACAG CGCTCTCCTG TGGAGTGAAA CTGTTGCCTA TGTTGTCCAG CCTGAGAAGC  2233

CCTCCATGTC CCCAAGGCTG CCAGACATGG ACTTCTAGCA AGTCCCCCAA CCCCCCATTC  2293

AACC                                                                2297
```

FIG. 13A

TGase1:

Thr Ala Ala Ala His Gly Ser Lys Pro Asn Val Tyr Ala Asn Arg Gly
1           5               10              15

Ser Ala Glu Asp Val Ala Met Gln Val Glu Ala Gln Asp Ala Val Met
        20              25              30

Gly Gln Asp Leu Met Val Ser Val Met Leu Ile Asn His Ser Ser Ser
        35              40              45

Arg Arg Thr
50

TGase2:

Arg Ala Asn His Leu Asn Lys Leu Ala Glu Lys Glu Glu Thr Gln Glu
1           5               10              15

Met Ala Thr Gly Val Ala Met Arg Ile Arg Val Gly Gln Ser Met Asn
        20              25              30

Met Gly Ser Asp Phe Asp Val Phe Ala His Ile Thr Asn Asn Thr Ala
        35              40              45

Glu Glu Tyr Val
50

TGase3:

Lys Ala Leu Gly Lys Leu Lys Pro Asn Thr Pro Phe Ala Ala Thr Ser
1           5               10              15

Ser Met Gly Leu Glu Thr Glu Glu Gln Glu Pro Ser Ile Ser Gly Lys
        20              25              30

Leu Lys Val Ala Gly Met Leu Ala Val Gly Lys Glu Val Asn Leu Val
        35              40              45

Leu Leu Leu Lys Asn Leu Ser Arg Asp Thr Lys Thr Val Thr Val Asn
        50              55              60

Met Thr Ala Trp Thr
65

FIG. 13B

XIIIa:

Thr Ala Leu Met Tyr Gly Ala Lys Lys Pro Leu Asn Thr Glu Gly Val
1              5                    10                  15

Met Lys Ser Arg Ser Asn Val Asp Met Asp Phe Glu Val Glu Asn Ala
              20                  25                  30

Val Leu Gly Lys Asp Phe Lys Leu Ser Ile Thr Glu Arg Asn Asn Ser
              35                  40                  45

His Asn Arg Tyr Thr
50

4.2:

Arg Val Glu Lys Glu Lys Met Glu Arg Glu Lys Asp Asn Gly Ile Arg
1              5                    10                  15

Pro Pro Ser Leu Glu Thr Ala Ser Pro Leu Tyr Leu Leu Leu Lys Ala
              20                  25                  30

Pro Ser Ser Leu Pro Leu Arg Gly Asp Ala Gln Ile Ser Val Thr Leu
              35                  40                  45

Val Asn His Ser Glu Gln Glu Lys Ala
      50                  55

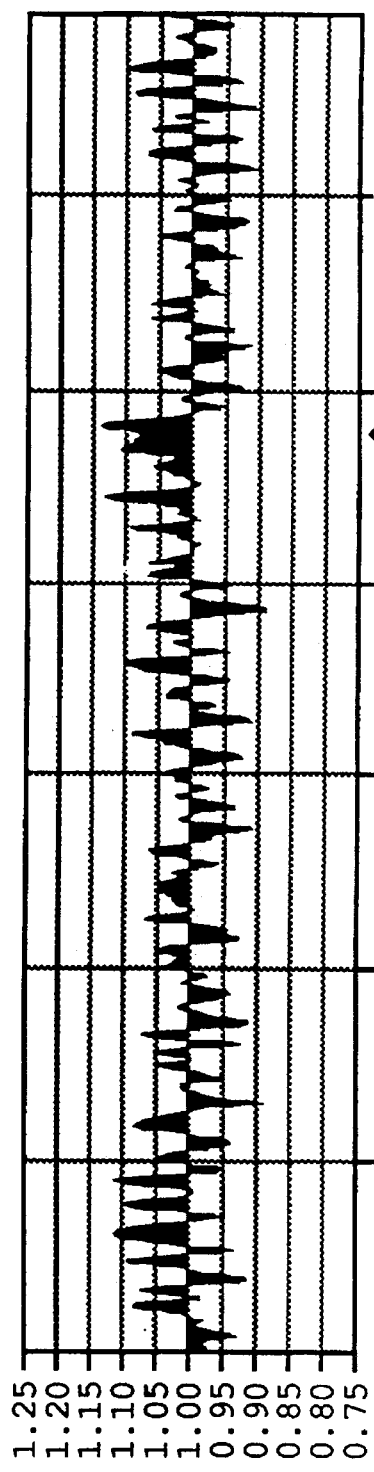
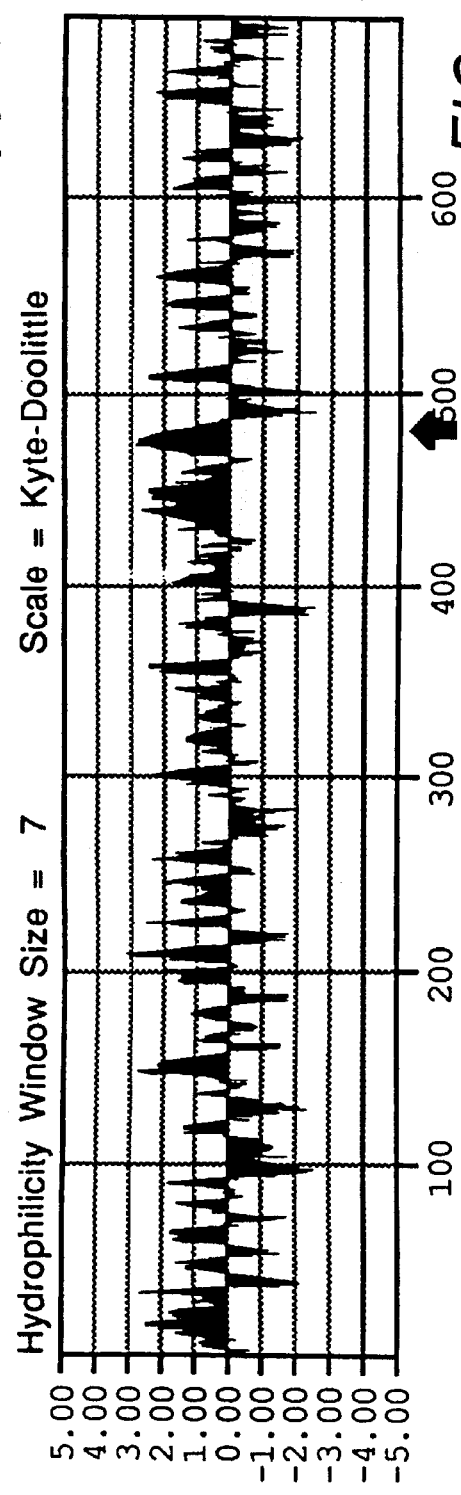
FIG. 14B
FIG. 14C

TRICHOHYALIN AND TRANSGLUTAMINASE-3 AND METHODS OF USING SAME

FIELD OF THE INVENTION

The present invention relates to the discovery of the sequences of several proteins which are involved in forming structural components in epidermal tissue: human trichohyalin, human transglutaminase-3, and mouse transglutaminase-3. Human trichohyalin is cross-linked to other proteins (including other trichohyalin proteins) by transglutaminase-3. Human and mouse transglutaminase-3 can be used to form gels and perform other useful functions.

BACKGROUND OF THE INVENTION

I. Trichohyalin

One of the major differentiation products of the inner root sheath and medullary cells of the developing hair follicle. Upon terminal differentiation in these tissues, the granules disperse, but the final fate and structure of TRHY appears to be site dependent: in the inner root sheath, the TRHY protein becomes enmeshed with the keratin intermediate filaments ("KIF") of the cells with an apparent periodicity of about 200 nm (range 100–400 nm) or 400 nm (range 200–500 nm); in the medulla, the protein forms amorphous deposits that are not organized in any specific way.

TRHY undergoes a series of calcium-dependent postsynthetic enzymic modifications. For example, it becomes highly cross-linked to the KIF by way of $N^\epsilon$-($\gamma$-glutamyl)lysine isodipeptide crosslinks which may be formed by the action of transglutaminases of the hair follicle cells. In addition, many of the arginine residues are desimidated to citrullines by the action of the enzyme peptidylarginine deiminase.

More recently, it has become clear that the expression of TRHY is not confined to the hair follicle. There is evidence showing that TRHY is expressed in the filiform papillae of dorsal tongue epithelium (Lynch, M. H., et al., *J. Cell Biol.* 103:2593–2606(1986)), a region that undergoes a course of "hard" keratin differentiation related to that in the hair follicle. In addition, indirect immunofluorescence data indicate that TRHY is also expressed in modest amounts in the granular layer of newborn human foreskin epidermis, although whether it is expressed in interfollicular trunk epidermis is not yet clear.

Current physico-chemical data suggests that human, sheep and pig TRHYs are large proteins of apparent molecular weight of about 200 kDa (Fietz, M. J., et al., *J. Cell Biol.* 110:427–436 (1990); O'Guin, W. M., et *J. Invest. Dermatol.* 98:24–32 (1992); Hamilton, E. H., et al., *J. Invest. Dermatol.* 98:881–889 (1992)). For pig TRHY there is evidence that two components of about 220 and 200 kDa exist. Shadowed electron micrographs of native pig tongue TRHY reveal an elongated particle of about 85 nm with a small bead on one end.

II. Transglutaminase-3

Transglutaminases (TGases) are calcium- and thiol-dependent enzymes that modify proteins by catalyzing the formation of an isodipeptide crosslink between an $\epsilon$-$NH_2$ of a lysine and the $\gamma$-amide of a glutamine residue (1–4). In mammals, five distinct TGases are known to exist: a membrane-associated activity first discovered in keratinocytes of about 92 kDa, TGase1, which is now known to be widely expressed; an ubiquitous "soluble" or "tissue" activity of about 80 kDa termed TGase2; a soluble pro-enzyme activity of about 77 kDa, known as the "epidermal" or "hair follicle" TGase3 (see, e.g, Kim, H.-C., et al., *J. Biol. Chem.* 265:29171–21978 (1990)); an inactive TGase-like protein of about 75 kDa, band 4.2, which is an ubiquitous constituent of the subplasma membrane of most eukaryotic cells (see Sung, I. A., et al., *Proc. Natl. Acad. Sci. U.S.A.* 87:955–959 (1990)); and the catalytic subunit of the blood clotting factor XIII of about 77 kDa (see, e.g, Takahashi, N., et al., *Proc. Natl. Acad. Sci. U.S.A.* 83:8019–8023 (1986)). Curiously, all but the latter member of this family are expressed in terminally differentiating epidermis.

Several early studies reported a soluble protein of about 50 kDa from both epidermal and hair follicle tissues of the guinea pig (see, e.g., Chung, S.-I. and Folk, J. E., *Proc. Natl. Acad. Sci. U.S.A.* 69:303–308 (1972)), but more rigorous biochemical and cell biological-analyses revealed that it is in fact a proenzyme, of molecular weight about 77 kDa, which becomes active upon proteolytic cleavage into a 50 kDa (amino terminal) and 27 kDa species (Negi, M., Colbert, M. C. and Goldsmith, L. A., *J. Invest. Dermatol.* 85:75–78 (1985)). While newer work has shown that these fragments are not normally separated upon activation (Kim, H.-C., et al., *J. Biol. Chem.* 265:29171–21978 (1990)), the fact that the isolated 50 kDa fragment can retain catalytic activity was the source of confusion in earlier studies. Furthermore, despite earlier work, it is now generally agreed that the epidermal and hair follicle pro-enzyme species are the same (Lichti, U., *Ann. N.Y. Acad. Sci.* 642:82–99 (1991)).

SUMMARY OF THE INVENTION

In one aspect, the present invention comprises a purified molecule of DNA which having 20 or more consecutive nucleotides from SEQ ID NO:93, including a sequence that is homologous to SEQ ID NO:93 or complementary to SEQ ID NO:93, wherein SEQ ID NO:93 codes for the human trichohyalin gene. This DNA molecule can, in one embodiment, comprise the complete coding sequence of SEQ ID NO:93. Such a DNA molecule can also comprise a probe or primer selected from the group consisting of molecules having the sequences of SEQ ID NO:1 to SEQ ID NO:10. In yet another embodiment, the DNA molecule according to this aspect of the invention is present in a recombinant DNA vector, such as a plasmid. Such a vector can in turn be placed into a cell line which does not naturally contain the molecule of DNA. In another embodiment, the present invention comprises a molecule of RNA which can be translated in vitro or in vivo into the human trichohyalin protein. Such an RNA molecule comprises the coding sequence of SEQ ID NO:93, except that the thymine molecules of SEQ ID NO:93 are replaced by uracil molecules, including an RNA molecule having a sequence that is homologous or complementary to this sequence. Molecules of RNA which comprises 20 or more consecutive nucleic acids from such an RNA molecule are also included in the invention. In yet another embodiment, the invention comprises a purified protein molecule comprising 20 or more consecutive amino acids of the amino acid sequence of SEQ ID NO:94, including a protein molecule that is homologous to SEQ ID NO:94. In one embodiment, the protein molecule comprises the sequence of the human trichohyalin protein and contains the sequence of SEQ ID NO:94. Antibodies, such as monoclonal antibodies, having binding affinity for human trichohyalin and not for trichohyalin derived from other species are also included in this aspect of the invention.

In another aspect, the present invention comprises another purified molecule of DNA which contains sequences coding for human transglutaminase-3. Such a molecule can comprise 20 or more consecutive nucleotides from SEQ ID NO:109, including a sequence that is homologous to SEQ ID NO:109 or complementary to SEQ ID NO:109. Alternatively, such a molecule can comprises the sequence of SEQ ID NO:109. A purified molecule of DNA according to this aspect of the invention can be placed in a recombinant DNA vector, such as a plasmid. Such a vector can then be placed in a cell line which does not naturally contain the molecule of DNA. Also included in this aspect of the invention is a purified molecule of DNA for use as a probe or primer, wherein the molecule is selected from the group consisting of molecules having the sequences of SEQ ID NO:47 to SEQ ID NO:54.

Another embodiment of this aspect of the invention includes a purified molecule of RNA which can be translated in vitro or in vivo into the human transglutaminase-3 protein and which comprises the coding sequence of SEQ ID NO:109, wherein the thymine molecules of SEQ ID NO:109 are replaced by uracil molecules. An RNA molecule having a sequence that is homologous or complementary to this sequence is also included. A purified molecule of RNA which comprises 20 or more consecutive nucleic acids from these RNA molecules is included as well. In another embodiment, the invention includes a purified protein molecule comprising 20 or more consecutive amino acids of the amino acid sequence of SEQ ID NO:112, including a protein molecule that is homologous to SEQ ID NO:112. Such a protein molecule can comprise the sequence of the human transglutaminase-3 protein, wherein the molecule comprises the sequence of SEQ ID NO:112. In a further embodiment, the invention also includes an antibody, such as a monoclonal antibody, having binding affinity for human transglutaminase-3 and not for transglutaminase-3 derived from other species.

In a further aspect of the present invention, the invention includes a purified molecule of DNA which comprises 20 or more consecutive nucleotides from SEQ ID NO:110, including a sequence that is homologous to SEQ ID NO:110 or complementary to SEQ ID NO:110, wherein SEQ ID NO:110 codes for the mouse transglutaminase-3 gene. Such a purified molecule of DNA can, in one embodiment, comprise the sequence of SEQ ID NO:110. Such a molecule of DNA can also be selected from the group consisting of molecules having the sequences of SEQ ID NO:33 to SEQ ID NO:46. In another embodiment, the DNA molecules according to this aspect of the invention are present in a recombinant DNA vector, such as in a plasmid. Such a vector can futher be present in a cell line which does not naturally contain the molecule of DNA.

In a further embodiment, this aspect of the present invention includes a purified molecule of RNA which can be translated in vitro or in vivo into the mouse transglutaminase-3 protein and which comprises the coding sequence of SEQ ID NO:110, wherein the thymine molecules of SEQ ID NO:110 are replaced by uracil molecules, including an RNA molecule having a sequence that is homologous or complementary to this sequence. Also included is a purified molecule of RNA which comprises 20 or more consecutive nucleic acids from such an RNA molecule. In another embodiment, the present invention comprises a purified protein molecule comprising 20 or more consecutive amino acids of the amino acid sequence of SEQ ID NO:111, including a protein molecule that is homologous to SEQ ID NO:111. Such a protein molecule can comprise the sequence of the mouse transglutaminase-3 protein, wherein the molecule comprises the sequence of SEQ ID NO:111. Also included in this aspect of the invention is an antibody, such as a monoclonal antibody, having binding affinity for mouse transglutaminase-3 and not for transglutaminase-3 derived from other species.

In yet another aspect, the present invention comprises a method of forming a proteinaceous gel, comprising the steps of: providing a gel forming substrate, the substrate comprising the human trichohyalin protein; adding to the substrate a gel-forming amount of an enzyme capable of cross-linking the human trichohyalin protein; and thereby forming a gel. This method can include the step of adding to the substrate a gel forming amount of human or mouse transglutaminase-3. In another embodiment, a food or cosmetic substance is mixed with the substrate.

Another aspect of the present invention comprises an aqueous gel composition, wherein the gel comprises cross-linked human trichohyalin molecules. This gel is preferably formed in a mold into a desired shape.

Yet another aspect of the present invention comprises a method of facilitating the healing of a wound, whereby tissue which has been torn to form the wound can be bound together, comprising the steps of: providing a solution containing human trichohyalin protein, wherein the concentration of the trichohyalin protein is between 0.01% and 5.0%; providing a solution containing an enzyme capable of cross-linking the trichohyalin protein; mixing the solution containing human trichohyalin with the solution containing the enzyme; and applying the mixture of solutions to a wound, whereby the enzyme in the mixture cross-links the human trichohyalin protein in the mixture and causes the mixture to solidify, thereby covering and protecting the wound. In this method, the enzyme used can be human transglutaminase-3, which is preferably present in an amount of between approximately 2% to 5% of the weight of the trichohyalin protein.

BRIEF DESCRIPTION OF THE FIGURES

FIG. 3 shows the DNA nucleotide sequence (SEQ ID NO:93) and predicted amino acid sequence (SEQ ID NO:94) of human TRHY. These data were accumulated from both the RNA-mediated anchored PCR cDNA clones and the genomic clone λH-TRHY-18. The nucleotide sequence is numbered from the extent of our available sequence data above the likely CAAT box. Intron sequences are shown in lower case letters. The likely CAAT, TATA, capsite, initiation, termination and polyadenylation signal sequences are underlined. The single letter code for amino acids is used, and residues are numbered from the codon following the initiation codon. Comparisons of the cDNA sequences and the available genomic sequences revealed a number of polymorphisms: the genomic clone contained an additional glutamic acid at position 459; and a number of silent nucleotide substitutions in the following codons: 15 (AAT or AAC), 113 (CGC or CGG), 460 (AGA or AGG), 842 (CGG or CGC), 1024 (CGC or CGG), 1199 (TGC or TGT), 1361 (GAA or GAG), 1362 (CAA or CAG), 1516 (GAG or GAA), 1559 (CTC or CTG) and 1766 (CTC or CTG).

FIG. 8 is a chart which aligns the amino acid sequences of human TRHY with a selection of human S100-like calcium binding proteins which contain two homologous EF-hand motifs. The arrow after residue 45 delineates the point at which intron 2 splices coding sequences between the two EF-hand motifs. The helix-turn-helix sequences which define each motif are shown. Relative amino acid deletions are denoted by –. The amino acid sequences of the non-TRHY proteins are derived from: Markova, N., et al., *Mol. Cell Biol.* 13:167–182 (1993) (profilaggrin); Kligman, D. and Hilt, R. H., *Novel Calcium-Binding Proteins,* Heizman, C. W., ed., Springer-Verlag, Berlin, 65–103 (1991) (S100α, p11, calcylin and cystic fibrosis antigen); Becker, T., et al., *FEBS Lett.* 207:541–547 (1992) (S100P).

FIGS. 11A–11F show the nucleotide (SEQ ID NO:109) and deduced amino acid (SEQ ID NO:112) sequences, respectively, of human TGase-3. FIGS. 11G–11K show the nucleotide (SEQ ID NO:110) and deduced amino acid (SEQ ID NO:111) sequences, respectively, of mouse TGase-3. For ease of description, these figures shall be referred to collectively as "FIG. 11". The initiation, termination and polyadenylation signal sequences are underlined. Nucleotide sequences are numbered following the initiation codon. The amino acid sequences are shown using the single letter code.

FIG. 13 is a chart aligning portions of the amino acid sequences of human TGase-like proteins. Alignments of the amino-terminal sequences are arbitrary. The arrowhead marks the presumed site of proteolytic cleavage required for activation of TGase3. Homology and identity scores (see Table 8) were calculated for sequences bounded by the closed dots (which correspond to the positions of known intron boundaries conserved in the genes of TGase1, factor XIIIa and band 4.2).

DETAILED DESCRIPTION OF THE INVENTION

Figures 1A, 1B:
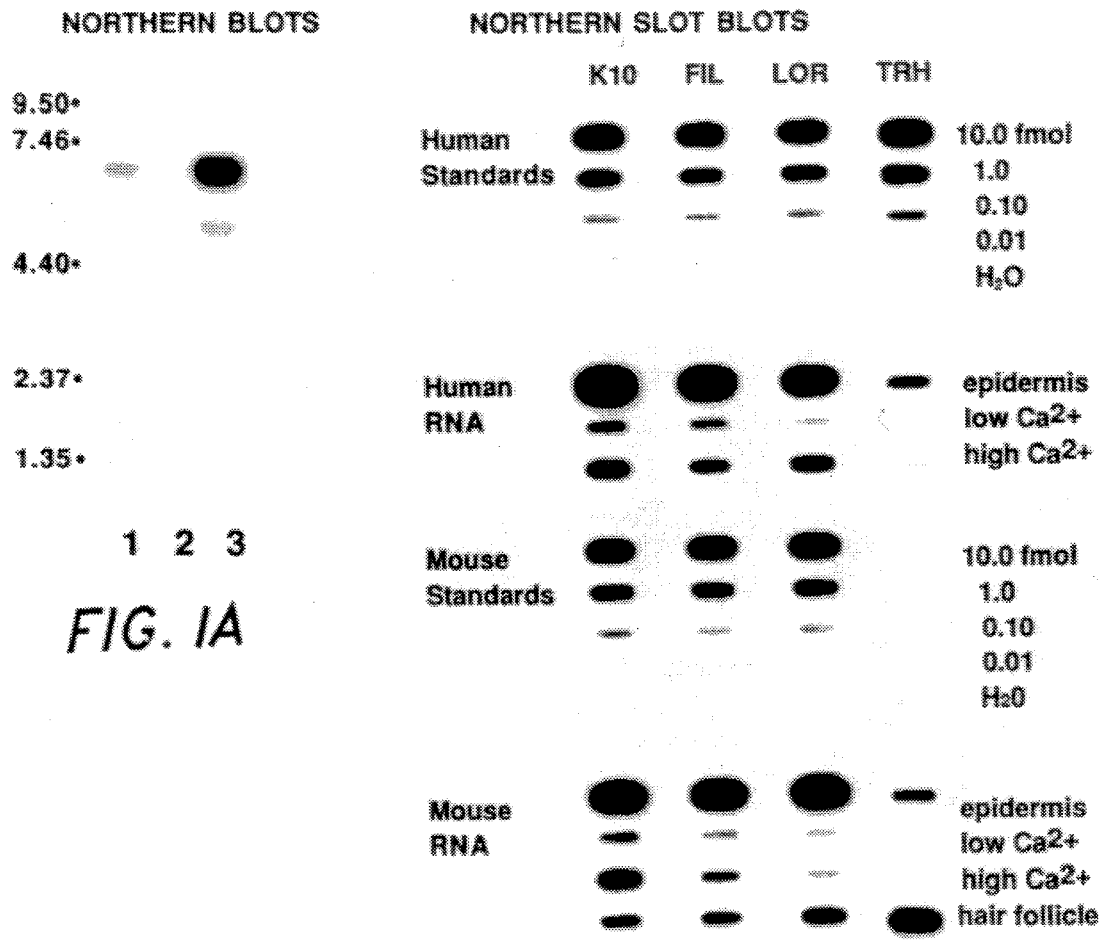
FIG. 1A is a picture of an x-ray film exposure of a northern gel (25 μg of sample per well) probed with a 504 bp cDNA clone encoding the carboxyl-terminal end of human trichohyalin. The samples probed represent one batch of total cellular RNA from each of: a sample of human foreskin epidermis (lane 1); a sample of mouse epidermis (lane 2); and a sample of mouse hair follicles (lane 3). Positions of size markers (Gibco-BRL) are shown.
FIG. 1B is a picture of an x-ray film exposure of a slot blot experiment which was performed to estimate the relative amounts of specific epidermal mRNAs in 10 μg of total cellular RNA from the sources shown. This figure shows an exposure of 6 days. The abbreviations use in this figure are: K10=keratin 10; FIL=profilaggrin; LOR=loricrin; TRH=trichohyalin.

Among the discoveries of the present invention is the determination of the sequences of three mammalian epidermal proteins, human trichohyalin, human transglutaminase-3, and mouse transglutaminase-3. These proteins are all found in terminally differentiating epidermal tissue and are involved in forming the structural architecture of such tissue. The structure-forming properties of these proteins are exploited in one aspect of the present invention by using the proteins to form gels, which can be used to form food and other useful products. Also included in the present invention is a novel method of facilitating the healing of wounds with the proteins described herein.

To facilitate the understanding of the present disclosure, the following terms are hereby defined. The term "coding for" as used herein, when applied to DNA molecules, refers to DNA molecules which contain the coding portions of a particular DNA sequence, that is, the portions making up the exons of such sequences. The exon sequences of these DNA molecules can be transcribed into RNA molecules which can in turn be translated into molecules of protein. RNA molecules which can be translated into such molecules of protein are also said to "code for" their corresponding proteins.

As further used herein, the terms "homologous" and "homology", when applied to proteins or amino acid sequences, describe amino acid sequences in which one amino acid has been substituted for by an amino acid with similar properties. An example of such a substitution is the exchange of an aspartic acid molecule for a molecule of glutamic acid. Other such similar pairs of amino acids are well known to those of skill in the art.

With regard to nucleic acid sequences, however, the terms "homology" and "homologous" carry the meaning of being able to hybridize to nucleic acids with complementary sequences under standard hybridization conditions for Northern hybridizations (when RNA is being hybridized to a target nucleic acid) or Southern hybridizations (when DNA is being hybridized to a target nucleic acid). Such standard hybridization conditions are discussed in Sambrook, J., Fritsch, E. F. and Maniatis, T., *Molecular Cloning: A Laboratory Manual.*, Cold Spring Harbor Press, Cold Spring Harbor, N.Y. (1989). This reference discloses, for example, hybridization wash conditions of 0.1×SSC and 0.5% SDS at 68° C. for 30 minutes to 1 hour. A nucleic acid with a "complementary" sequence is one which can hybridize to a target nucleic acid sequence under such standard hybridization conditions.

As used herein, the term TGase3, by itself, shall refer to both mouse and human TGase3, unless the context indicates to the contrary. In addition, for the sake of clarity the following list of some of the abbreviations used herein is set forth immediately below:

TRHY=trichohyalin

TGase=transglutaminase

TGase3=transglutaminase-3 (also transglutaminase E)

CE=cornified cell envelope

FFT=Fast Fourier Transform

IF=intermediate filaments

IFAP=intermediate filament associated protein

KIF=keratin intermediate filaments

PCR=polymerase chain reaction nt=nucleotide(s)

knt=kilonucleotides bp=base pair(s)

kbp=kilobase pairs kDa=kilodalton

µg=micrograms ng=nanograms fmol=femtomoles pmol=picomoles d=day h=hour

Other terms and abbreviations used herein are defined below.

I. Human Trichohyalin

We have now discovered the full-length sequence of human TRHY, deduced from the sequences of PCR-derived cDNA clones and of a genomic clone. Analyses of its secondary structure suggest that it adopts a flexible single-stranded α-helical rod-like conformation. In this way, TRHY is remarkably similar to but about four times longer than involucrin, a known protein constituent of the cornified cell envelope of the epidermis. However, unlike involucrin, TRHY possesses functional calcium-binding motifs of the EF-hand type at its amino terminus as does profilaggrin, the precursor of a known interfilamentous matrix protein of the epidermis. The potential significance of these several structural motifs suggests TRHY may have multiple functions in the epidermis and hair follicle cells.

Figure 6:
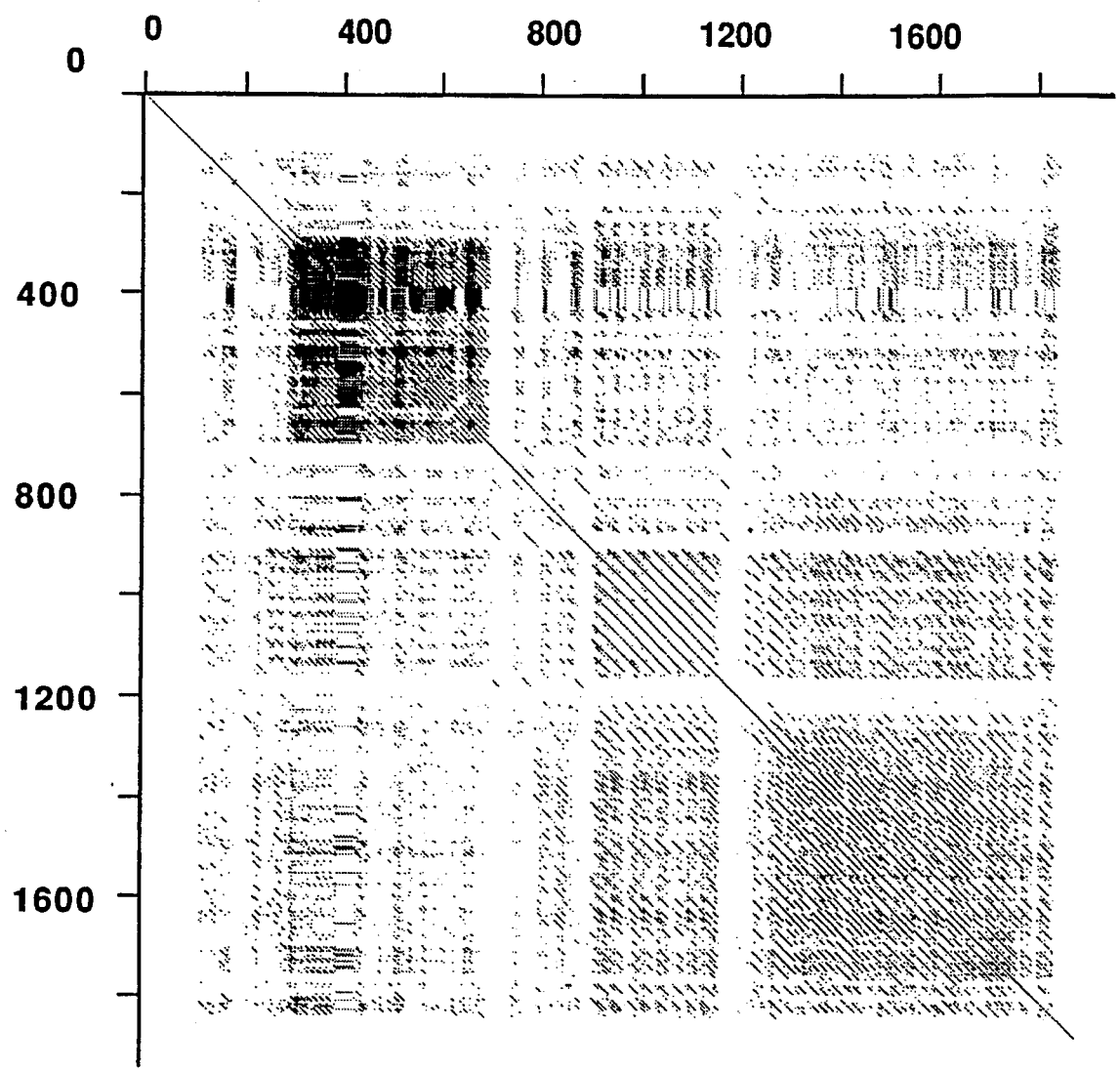
FIG. 6 is a dot matrix profile which reveals that human TRHY evolved assembled from multiple repeating peptide sequences. The homology scoring method of Pearson, W. R. and Lipman, D. J., *Proc. Natl. Acad. Sci. U.S.A.,* 85:2444–2448 (1988) was used with a window size of 18 residues and homology of 50%. Several major and some minor blocks of repeating sequences are evident, suggesting that the TRHY molecule was formed during evolution from blocks of peptide repeats that were joined together by non-conserved sequences.

Trichohyalin is an intermediate filament associated protein that associates in regular arrays with keratin filaments (KIF) of the inner root sheath cells of the hair follicle and the granular layer of the epidermis, and is a substrate of transglutaminases. We have determined the full-length sequence of human trichohyalin by use of RNA-mediated anchored PCR methods and from a genomic clone, and have analyzed its potential secondary structure. We show here that trichohyalin may have at least three important functions in these cells. The protein of 248 kDa is unusual in that it contains one of the highest contents of charged residues of any protein. Of several defined domains (shown in FIG. 6), domains 2, 3, 4, 6 and 8 are almost entirely α-helical, configured as a series of peptide repeats of varying regularity, and are thought to form a single stranded α-helical rod stabilized by ionic interactions between successive turns of the α-helix. Domain 6 is the most regular and may bind KIF directly by ionic interactions. Domains 5 and 7 are less well organized and may introduce folds in the molecule. Thus, human trichohyalin is predicted to be an elongated flexible rod at least 215 nm long, and to function as a KIF associated protein by crosslinking the filaments in loose networks.

A. Procedures Used to Isolate and Sequence the Trichohyalin Gene

1. Procedures for the Isolation and Sequencing of cDNA and Genomic Clones

A large portion of the cDNA sequences encoding human TRHY was determined by RNA-mediated anchored PCR (as taught in Frohman, M. A., *PCR Protocols: A Guide to Methods and Applications* Innis, M. A., et al., eds., Academic Press Inc., New York, 28–38 (1990)) and by characterization of the resulting sequence information. The carboxyl-terminal portion of the TRHY sequence was first identified by probing human genomic DNA with primers which coded for portions of the carboxyl-terminal portion of sheep TRHY (Fietz, M. J., et al., *J. Cell Biol.* 110:427–436 (1990)). In this way, a 504 bp cDNA clone (later determined to code for the carboxyl-terminal end of human trichohyalin) was identified (see Lee, S.-C., et al., *J. Invest. Dermatol.* 98:626 (1992)). This probe was then used to reverse transcribe an aliquot of 200 ng of DNase1-treated total foreskin epidermal RNA (Steinert, P. M., et al., *J. Biol. Chem.* 260:7142–7149 (1985)) at 70° C., resulting in the minus strand marked as 2– in FIG. 2 (SEQ ID NO:3). Approximately 20 picomoles of a primer of about 20 nt having a unique sequence found in the 2– strand was then reverse transcribed at 70° to produce the 3– strand (SEQ ID NO:4). A series of minus strand primers (listed in Table 2 below) were designed in this way and used to determine the full-length sequence of human trichohyalin.

The PCR reactions using the specific primers in Table 2 were performed with a commercial DNA amplification reagent kit (from Perkin-Elmer Cetus, Norwalk, Conn.) by following the manufacturer's specifications, using 25 pmol of an adaptor dG oligonucleotide as the plus primer and 25 pmol of one of the specific primers shown in Table 2 as the minus primer. The conditions of PCR were: 95° C. (5 min); and cycled for 30 cycles at denaturation of 95° C. (0.5 min); annealing at 42° C. (0.5 min); and elongation at 72° C. (1.5 min). In some cases where the yield was low (due to difficulties of amplifying the multiple exact repeat regions), a portion of the PCR reaction mixture was then diluted 1:1000 with buffer and 1 µl was reamplified in a second round of PCR. After each round of PCR, the primer was removed using Chroma spin 100 columns (made by Clontech, Palo Alto, Calif.), and the cDNAs thus produced were tailed in the presence of 200 µM dCTP with 25 units of terminal deoxytransferase (supplied by Gibco-BRL, Gaithersburg, Md.) for 1 h at 37° C.

The cDNA products of these PCR procedures were fractionated on low-melting agarose gels and the largest fragments containing the most extended products were excised. Following purification through Chroma spin columns, the ends of the amplified cDNAs were filled in with Klenow DNA polymerase (as taught in Sambrook, J., Fritsch, E. F. & Maniatis, T., *Molecular Cloning: A Laboratory Manual*, Cold Spring Harbor Press, Cold Spring Harbor, N.Y. (1989)), subcloned into the pGEM-3z vector (supplied by Promega, Madison, Wis.), and then sequenced by the didexoy chain-termination method with Sequenase 2.0 (sold by United States Biochemical Corp., Cleveland, Ohio). Following analysis of the sequence information of the amplified cDNAs from each round of PCR, new primers with unique (non-repeating) sequences were designed. For example, after analyzing the sequence of the 2– strand, a 2– primer was selected which had a unique sequence and this primer was then used to generate the 3– strand. This process was continued as far as possible in a total of nine steps.

Because of uncertainties with the location of the likely initiation codon and 5'-end of the mRNA, the 504 bp cDNA clone referred to above was used as a probe to screen a human placental genomic DNA library (provided by Clontech, Palo Alto, Calif.). Using this 504 bp probe, a 14 kbp genomic clone, termed λH-TRHY-18, was isolated and plaque-purified. Following Southern blotting analyses of this genomic clone, 6.5 kbp Sac 1 and 8.0 kbp Xho 1 fragments of the clone containing the entire coding region of the human TRHY gene were cloned into pGEM-3z. Sequencing of these clones was done following creation of a nested set of deletion subclones by use of the Erase-a-Base kit system (available from Promega, Madison, Wis.) with the T7 and SP6 vector primers.

2. Northern Blot Analyses

Using established methods, total cellular RNA was prepared from human foreskins (see Steinert, P. M., et al., *J. Biol. Chem.* 260:7142–7149 (1985)), newborn mouse epidermis (see Roop, D. R., et al., *Proc. Natl. Acad. Sci. U.S.A.* 80:716–720 (1983)), and human and mouse epidermal keratinocytes grown to confluency in the presence of low (0.1 mM) or high (0.6 mM) $Ca^{2+}$ (see Yuspa, S. H., et al., *J. Cell Biol.* 109:1207–121 (1989) and Hohl, D., et al., *J. Invest. Dermatol.* 96:414–418 (1991)). RNA was also prepared from hair follicles purified from 5 day old mice. Northern gels loaded with 25 µg of RNA were performed by established procedures (Hamilton, E. H., et al., *J. Invest. Dermatol.* 98:881–889 (1992)), and calibrated with standard RNA size markers (available from Gibco-BRL, Gaithersburg, Md.).

Northern slot blotting was done as described in Sambrook, J., Fritsch, E. F. & Maniatis, T., *Molecular Cloning. A Laboratory Manual.*, Cold Spring Harbor Press, Cold Spring Harbor, N.Y. (1989). In this case, the blots were calibrated with 0.01 to 10 femtomole amounts of cloned probes for human and mouse keratin 10 (see Zhou, X.-M., et al., *J. Biol. Chem.* 263:15584–15589 (1988) and Steinert, P. M., et al., *Nature* (London) 302:794–800 (1983)); human (33) and mouse (34) filaggrin (see McKinley-Grant, L. G., et al., *Proc. Natl. Acad. Sci. U.S.A.* 86:4848–4852 (1989) and Rothnagel, J. A. and Steinert, P. M., *J. Biol. Chem.* 265:1862–1865 (1990)); loricrin (see Hohl, D., et al., *J. Biol. Chem.* 266:6626–6636 (1991)); and a 6.5 kbp human TRHY genomic clone described below. Slots of samples containing 10 μg of total cellular RNA were then tested with specific 3'-non-coding probes to each of the above. All Northern filters were washed with a final stringency of 0.5×SSC at 65° C. for 30 min. The resulting X-ray films were exposed for varying amounts of time in order to facilitate quantitation of the abundance of the specific mRNA species by scanning densitometry.

3. Protein Secondary Structure Analyses

Protein sequence homologies and secondary structure predictions were performed using the AASAP (Amino Acid Sequence Analysis Program (obtained from Dr. David Parry in New Zealand), the University of Wisconsin sequence analysis software packages (UWGCG) compiled by the Wisconsin Genetics Computer Group (Devereux, J., et al., *Nucleic Acids Res.* 12:387–395 (1984)), the International Biotechnologies Inc. Pustell sequence software (version 3.5) (from IBI, New Haven, Conn.) and Intelligenics Geneworks software (Pearson, W. R. and Lipman, D. J., *Proc. Natl. Acad. Sci. U.S.A.* 85:2444–2448 (1988)). Dot matrix comparisons were performed using the COMPARE and DOT-PLOT program on UWGCG running on the Massey University VAX or Geneworks. Fast Fourier Transform (FFT) analyses to determine the periodic distributions of residues or residue types were carried out as described by McLachlan, A. D. and Stewart, M., *J. Mol. Biol.* 103:271–298 (1976). General structural principles pertaining to α-helic-rich proteins (Cohen, C. and Parry, D. A. D., *Proteins: Structure, Function and Genetics* 7:1–15 (1990)) were used in preliminary analyses.

Numbers of potential intrachain ionic interactions between oppositely-charged residues four apart (that is, i→i+4) in a likely α-helical structure were calculated and placed on a per heptad (seven residue) basis. These values, designated here as I4, represent a measure the number of charged to uncharged amino acids in a peptide. They allow direct comparisons with the interchain ionic interactions made between the chains of multi-stranded α-fibrous proteins. Such values typically lie in the range 0.2–0.8 (Conway, J. F. and Parry, D. A. D., *Int. J. Biol. Macromol.* 12:328–334 (1988)). Ionic interactions are known to stabilize an α-helical structure through the formation of salt links between residues on adjacent turns of the α-helix.

B. Results of Experiments to Isolate and Sequence the Trichohyalin Gene

1. Northern Blot Analyses

The previously described 504 bp cDNA clone representing the carboxyl-terminal portion of TRHY was used as a probe to estimate the size, relative abundance and expression characteristics of human TRHY mRNA. On Northern gels, human and mouse TRHY mRNAs are approximately 6.7 kb in size (FIG. 1A). This estimate is about 10% larger than for sheep TRHY mRNA. In slot blotting assays, we estimated the abundance of human TRHY mRNA in relation to a number of major epidermal mRNA species, including keratin 10, profilaggrin and loricrin (FIG. 1B). As shown in Table 1 below, densitometric scanning of slot blots, including that depicted in FIG. 1B, revealed that TRHY is <0.4% and <0.6% as abundant as keratin 10 or profilaggrin, respectively, in both human and mouse epidermis. The results of Table 1 were determined by exposing X-ray films with the blots for several different time periods, ranging from 4 hours to 46 days.

Since the keratin 10 mRNA is thought to constitute about 25% of epidermal mRNA, this means that TRHY represents about 0.1% of total epidermal mRNA. While we have no information on the rates of turnover or the efficiency of translation of the TRHY mRNA, these data nevertheless confirm that TRHY protein is a minor but significant component of the terminal differentiation pathway of human epidermis. Similar experiments have revealed that the mRNA for involucrin is about five times more abundant than TRHY. In addition, the expression of TRHY mRNA is down-regulated in submerged liquid cultures of both mouse and human epidermal cells grown in low calcium (0.1 mM medium, and its expression is somewhat elevated by raising the calcium concentration to near optimal levels (0.6 mM) (see FIG. 1B and Table 1). Thus, the expression of TRHY mRNA is closely coordinated with that of other late differentiation products of the epidermis such as keratin 10, profilaggrin and loricrin (Table 1).

2. The Deduced Amino Acid Sequence of Human TRHY

Figure 2:
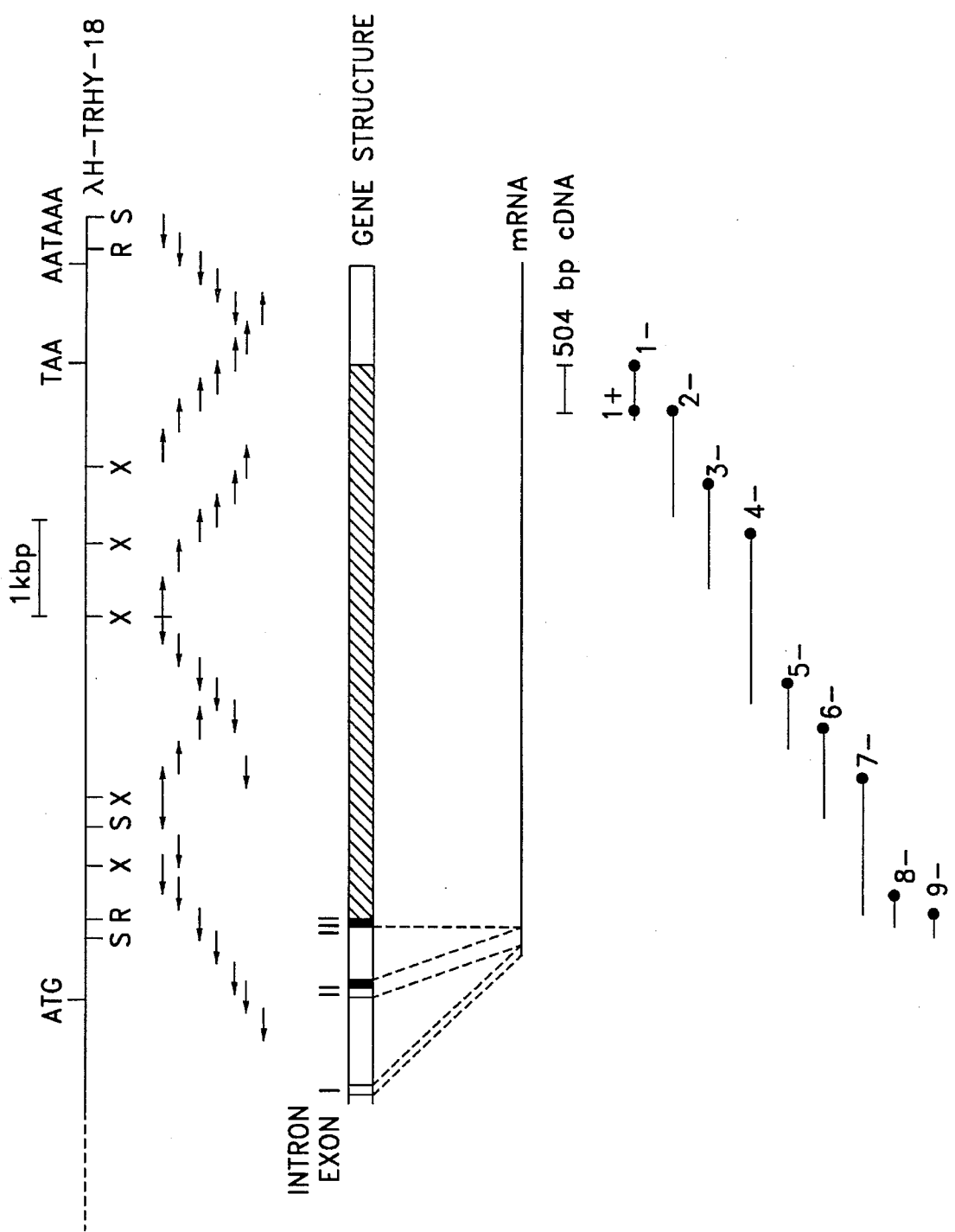
FIG. 2. is a strategy map for the sequencing of human TRHY cDNA and genomic clones. The upper line designates the location of the genomic clone λH-TRHY-18 in relation to the sequencing information. The abbreviations for restriction enzyme sites are: R=EcoRI; S=Sac I; X=Xho I. The nested arrows denote sequences determined by deletion subcloning. The second line illustrates the structure of TRHY gene. Exon I of 63 nt consists entirely on 5'-noncoding sequences; intron 1 is 1275 nt long; exon II of 169 nt contains the likely initiation codon and encodes the first EF-hand motif; intron 2 is 864 nt long; and the large exon III (6609 nt) consists of an additional 5553 nt of coding sequences and 1056 nt of 3'-non-coding sequences to the polyadenylation signal sequence. The positions of the two EF-hand calcium binding domains are shown in black; the remainder of the coding sequences are hatched; 5'- and 3'-non-coding sequences are open boxes. The third line designates mRNA structure. Dotted lines connect the exon sequences to the mRNA structure. Below this are shown the locations of the 504 bp cDNA clone referred to above and of the various cDNA clones constructed by primer extension and anchored PCR methods. The numbered spots 1+ (SEQ ID NO: 1), 1– (SEQ ID NO: 2) denote the primers used to amplify the 504 bp cDNA clone; primers 2– (SEQ ID NO: 3), 3– (SEQ ID NO: 4), etc. refer to the primers used for extension and PCR. The sequences and numbered locations of these primers are listed in Table 2 below.

We have used a combination of two strategies to obtain the full-length coding sequence of human TRHY. In the first, human TRHY-specific oligonucleotide primers (listed in Table 2) were constructed and used to prepare cDNAs by primer extension. In this way, it was possible to "walk" up most of the length of the mRNA (as shown in FIG. 2). The primer 9-(SEQ ID NO:10) extended only an additional 230 bp, indicating that we had extended close to the 5'-end of the mRNA. The sequences of the oligo-dG-tailed product of primer 9-included a potential initiation codon that conformed to a Kozak initiation site (Steinert, P. M. and Steven, A. C., *J. Invest. Dermatol.* 98:559 (1992)), but we were uncertain whether this represented the true initiation codon, largely because we found these TRHY sequences shared a high degree of homology to those of the much more abundant profilaggrin mRNA (see FIG. 7 below).

Accordingly, in the second approach, the 504 bp cDNA clone was used to isolate a 14 kbp genomic clone, λH-TRHY-18. By Southern blotting techniques using the aforementioned 504 bp clone and several of the primer-extended cDNA clones described above, λH-TRHY-18 was found to extend several kbp upstream and thus contains the entire coding region of human TRHY (FIG. 2). Following subcloning, a 4.1 kbp portion overlapping the cDNA information was sequenced using Erase-a-Base methods (Promega, Madison, Wis.).

Comparisons of the sequences of the available cDNA clones and λH-TRHY-18 revealed the presence of two introns toward the 5'-end of the TRHY gene. One intron of 1275 bp splices sequences 54 bp and a second intron of 864 bp splices sequences 223 bp from the 5'-end of our cDNA sequence information. These introns define an exon I of at least 54 bp and an exon II of 169 bp. Exon II contains the in-frame initiation codon described above (FIG. 2, 3). Because we were unable to further primer-extend TRH mRNA sequences, we conclude that the primer extension experiments had reached very close to the cap-site for the TRHY mRNA. Indeed, searches for consensus sequences revealed a likely capsite just 9 bp upstream, at position 139 of FIG. 3.

Potential TATA and CAT boxes reside 23–33 bp and about 100 bp above this capsite. Thus, the 5'-end of the TRHY gene is remarkably similar to the 5'-end of the profilaggrin gene (Markova, N., et al., *Mol. Cell Biol.* 13:167–182 (1993)) and to several genes encoding small calcium-binding proteins of the S100 family that contain EF-hand motifs (Kligman, D. and Hilt, R. H., *Novel Calcium-Binding Proteins*, Heizman, C. W., ed., Springer-Verlag, Berlin, 65–103 (1991)). The TRHY gene, like all of these other genes, contains an exon I of 50–70 nt in 5'-non-coding sequences, an intron of 1 of 1–10 knt, an exon II of 150–170 nt containing the initiation codon and the first EF-hand motif, a short intron 2, and exon III which contains the second EF-hand motif and the entire remainder of the coding and 3'-non-coding sequences. In the case of TRHY, exon III 6609 nt (to a consensus polyadenylation signal sequence) including 5553 nt of coding and 1056 nt of 3'-non-coding sequences. The human TRHY mRNA is likely to be about 6.9 kb in length (including a polyA tail), in good agreement with the size estimate of 6.7 kbp estimated by Northern blotting (FIG. 1A).

The nucleotide sequence from the likely initiation codon defines a single open reading coding frame of 5691 nt, and thus the deduced amino acid sequence for human TRHY contains 1897 amino acids (excluding initiating methionine) of calculated molecular weight of 248 kDa and pI (isoelectric point) of 5.4 (FIG. 3). Thus, the molecular weight of human TRHY is about 25% and 15% higher than has been reported by SDS polyacrylamide gel electrophoresis for sheep or pig TRHY.

The net calculated pI is lower than predicted previously from histochemical staining methods for arginines (Rogers, G. E., *Expt. Cell Res.*, 14:378–387 (1958)). Only about 3 of the 45 serines+threonines are potential targets for phosphorylation by known protein kinases, and none of the 8 asparagines are likely candidates for glycosylation. The human TRHY sequence contains an extraordinarily high number (59%) of charged residues (aspartic acid D, glutamic acid E, histidine H, lysine K and arginine R), as well as many glutamines (Q). Comparisons with the GenBank and NBRF databases reveal that only one other described protein, involucrin, has similar high content of charged residues (49%). TRHY is also homologous to members of the S100 class of small calcium binding proteins.

3. Secondary Structure Features of Human Trichohyalin

Figure 4:
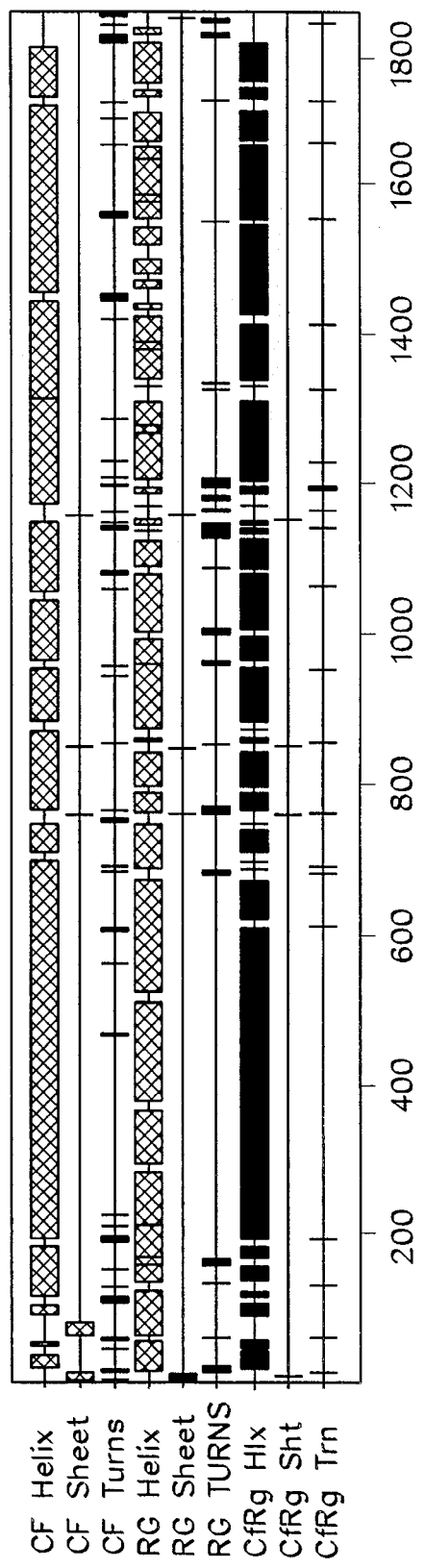
FIG. 4 depicts the predicted secondary structure features of human TRHY. This is set out in linear form for three structural motifs based on Chou-Fasman (CF), Robson-Garnier (RG) or consensus (CfRg) analyses of the WGCG package of analyses (Devereux, J., et al., *Nucleic Acids Res.* 12:387–395 (1984)). The molecule is mostly α-helical, configured in a series of long segments, interspersed by less regular regions matching the occasional proline residues, and it contains three potential sheet structures.

Secondary structure analyses suggest that about 75% of the human TRHY protein will adopt an α-helical conformation. Two pairs of short α-helical segments are predicted to occur in the first 90 residues, followed by a series of α-helical segments of 50 to 600 residues in length which encompass all the protein except for a short non-α-helical carboxyl-terminal domain about 40–50 residues long (FIG. 4). The α-helical segments are interrupted by occasional short β-turn sequences containing proline residues (FIG. 4). These algorithms predict only small sections of sheet structure near the amino-terminus, and three other sections along the protein between residues 720–730, 780–790, 885–910, where an (apolar-polar)$_{3-4}$ periodically occurs.

Figure 5:
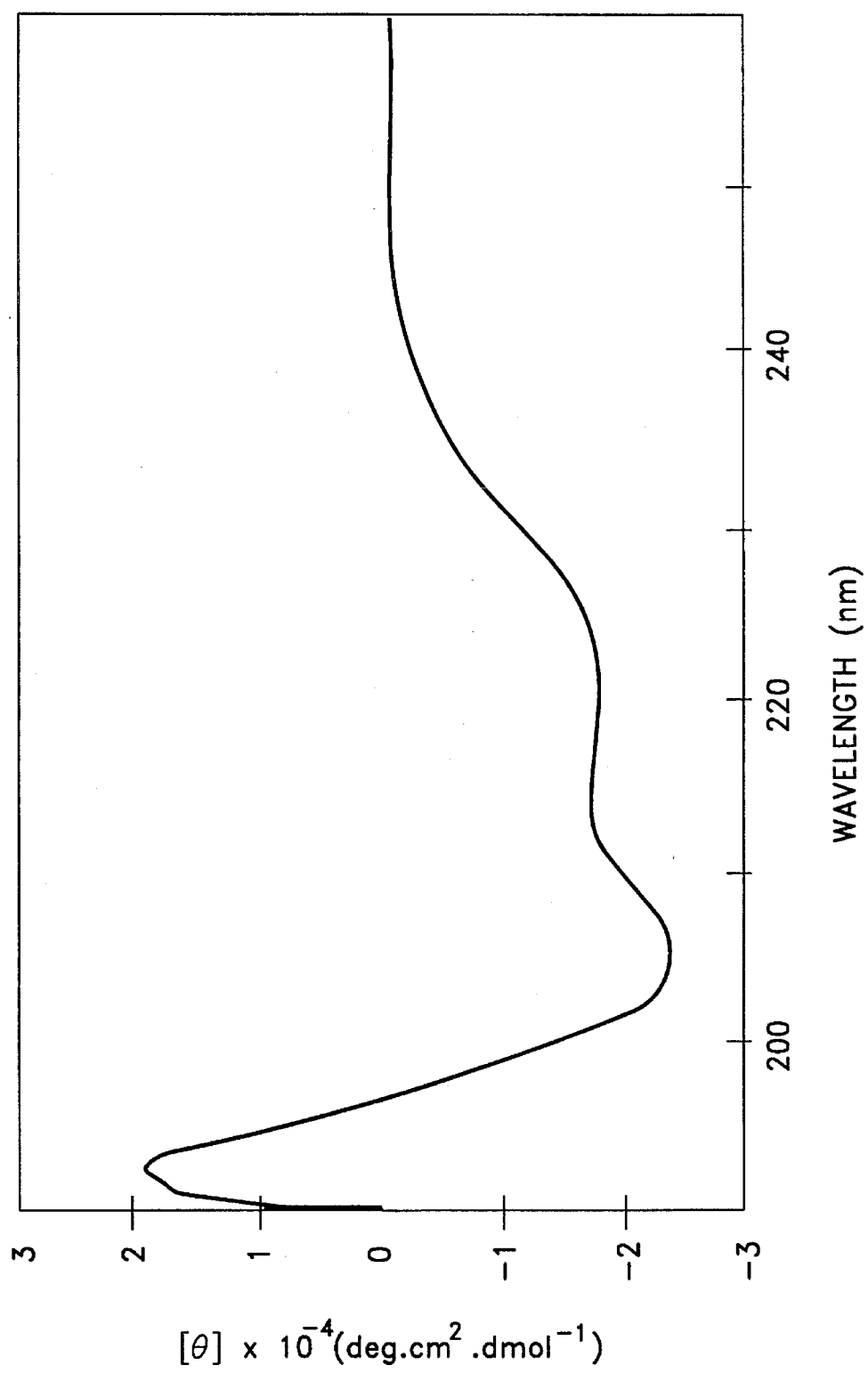
FIG. 5 is a graph of the circular dichroism spectrum of pig tongue TRHY showing that this protein is a highly α-helical molecule. The pig tongue TRHY, prepared under non-denaturing conditions, was equilibrated into 20 mM sodium phosphate (pH 7.0) containing 1M NaCl, and its circular dichroism spectrum was measured in a Jasco J600 spectropolarimeter.

The presence of the high α-helical content is supported by direct physical measurement with circular dichroism of pig TRHY (FIG. 5). Although human TRHY had not been isolated from any tissue before the present invention, it has been recently shown that pig tongue TRHY can be isolated in bulk using non-denaturing conditions (Hamilton, E. H., et al., *J. Invest. Dermatol.* 98:881–889 (1992)). Based on poly(L) lysine standards (Kligman, D. and Hilt, R. H., *Novel Calcium-Binding Proteins,* Heizman, C. W., ed., Springer-Verlag, Berlin, 65–103 (1991)), the mean molar ellipticity value of –21,400 deg.cm$^2$/dmol suggests that pig TRHY has an α-hfelical content of 65–70%, β-sheet content of 10–15% and with 10–20% random coil These values are in good agreement with the computer predictions of human TRHY shown in FIG. 4.

Figure 7:
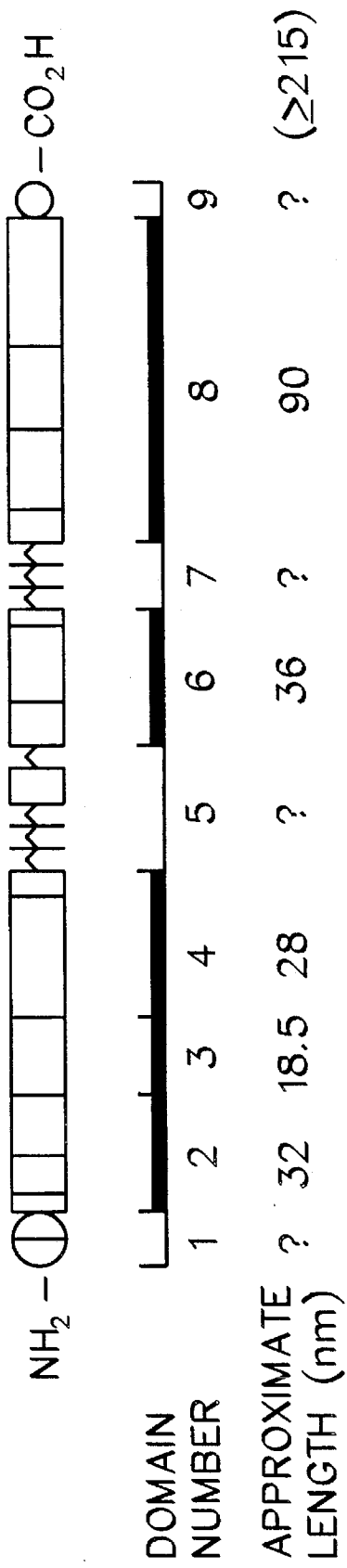
FIG. 7 depicts a model of the structure of human TRHY. This model consists of 9 domains. Domain 1, shown as a circle, contains two EF-hand calcium binding domains. Domains 2, 3, and 4 are largely α-helical and delineated by varying peptide repeats (see Table 3). Domain 5 contains several short and one longer stretch of α-helix interspersed by turn, coil or possibly sheet regions. Domain 6 also adopts an elongated configuration and constitutes the most regular portion of the molecule, to which KIF may associate through periodic ionic interactions. Domain 7 is also likely to be folded. The long domain 8 consists of peptide repeats which adopt an elongated α-helical configuration. Domain 9 contains the carboxyl-terminus, apparently conserved among TRHY molecules of different species. The lengths (in nm) of the more regular domains are shown. Human TRHY appears to either: (a) fold in half around domains 5 and 7 so as to produce an elongated configuration about 100 nm long with a large bend 15–20 nm in diameter corresponding to domain 6; or (b) remain extended and is >215 nm.

Analysis of the human TRHY sequence by dot matrix plots using the homology scoring system of Pearson and Lipman (see Pearson, W. R. and Lipman, D. J., *Proc. Natl. Acad. Sci. U.S.A.* 85:2444–2448 (1988)) reveals the presence of several regions of peptide repeats (see FIG. 6 and Table 3). These repeating regions are interspersed by regions of various lengths that lack the degree of regularity in the primary structure that is characteristic of most of the molecule. These observations indicate that the TRHY molecule consists of multiple domains, as set forth in detail below. Fast Fourier Transform (FFT) analyses (described in McLachlan, A. D. and Stewart, M., *J. Mol. Biol.* 103:271–298 (1976)) were used to evaluate these regions in detail and the results are summarized in Table 3. Repeating peptide sequence motifs are shown. A model based on these analyses is shown in FIG. 7. This model contains the following motifs:

(1) The first 94 residues, which are predicted to be about 50% α-helical, contain two calcium binding domains of the EF-hand type which have 60–70% sequence homology in this region with members of the S100 class of small calcium binding proteins (described in Kligman, D. and Hilt, R. H., *Novel Calcium-Binding Proetins,* Heizman, C. W., ed., Springer-Verlag, Berlin, 65–103 (1991)), and 70% homology to human profilaggrin (see Markova, N., et al., *Mol. Cell Biol.* 13:167–182 (1993) and see also FIG. 8). Each domain is composed of an ordered series of polar residues that are flanked by hydrophobic sequences and which adopt the helix-turn-helix conformation required to bind a single $Ca^{2+}$ ion. The two EF-hand motifs are separated and immediately flanked by sequences that have not been well conserved between members of the S100 class of proteins.

(2) Residues 95–312 are predicted to be largely α-helical (>75%) but will suffer disruptions at the two proline residues. There are no developed peptide repeats in this region. Nonetheless, charged residues of opposite sign frequently interface each other on alternate turns of the α-helix, thereby stabilizing a single-stranded α-helix through intrachain ionic interactions of the type i→i+4 (Marquesee, S. and Baldwin, R. L., *Proc. Natl. Acad. Sci. U.S.A.* 84:8898–8902 (1987)). The remarkably high charged/apolar ratio of 4.4 and I4 value of 1.54 (Table 3) are suggestive of an elongated α-helical rod structure about 32 nm long.

(3) Residues 313–443 can be subdivided into two sections, 313–389 and 390–443, on the basis of two well-developed types of repeats of 13 and 6 residues, respectively (Table 3). These are predicted to be entirely α-helical, and again, adjacent turns of the α-helix are likely to be stabilized by favorable ionic interactions between interfaced oppositely charged residues. Thus, the high I4 value and the high charged/apolar ratio together favor the formation of an elongated α-helical rod structure about 19 nm in length.

(4) Residues 444–702 consist of an irregular repeat dominated by numerous net deletions, but with a consensus repeat of 28 residues (Table 3). It is likely to be almost entirely α-helical, though disrupted once by a single proline. It may possess additional flexible regions around multiple adjacent glutamines, the tryptophan and/or serines, threonines. The I4 value of 2.17 is the highest in the entire molecule, indicating the potential for a very stable α-helical structure also stabilized by intrachain ionic interactions on alternate turns of the α-helix. This rod-like domain would be about 38 nm long.

(5) Although residues 703–922 are predicted to have a significant amount of α-helical structure, there are likely to be numerous breaks due to multiple prolines. Also, a semi-conserved repeat containing a characteristic pair of tryptophan (Table 3) is less clearly α-helical than most of this segment and may even favor the formation of intrachain or interchain sheet structures about the (polar-apolar)$_{3-4}$ environment. No other clear-cut repeat is evident and the I4 value of 1.05 is one of the lowest in the entire molecule. Because of the predicted turns and the tryptophan-rich quasi-repeats, this region may adopt a more folded configuration of indeterminate net length.

(6) Residues 923–1163 consist of eight almost perfect repeats of 30 residues (as evident from the matrix plot of FIG. 6) that are almost entirely α-helical, save for two potential kinks about the prolines. The very high I4 value of 2.03 and the charged/apolar ratio of 4.85 indicate a highly stabilized elongated rod structure of about 36 nm, common in segments 2–4 above. Interestingly, the 30 residue repeat also contains significant subrepeats (Table 3), especially one of length 7.5 residues. This occurs for glutamic acid (scaled Fourier intensity 43.61 and probability of occurring by chance 1.1 s $10^{-19}$), leucine, and for arginine (Table 3) and shows that the true period is approximately quartered. It also has the effect of placing an arginine or glutamate on almost every other turn of one face of the α-helix. Since this is slightly out of phase with 7.2 residues per two turns of an α-helix, it will result in positively- and negatively-charged stripes winding around the axis of the α-helix with a pitch length of about 14 nm.

(7) Residues 1164–1249 have similarities to those in segment 5 in that they are predicted to have significant α-helical content, but are nonetheless likely to be folded at least in part through the presence of predicted turns. Also present is a reasonably well defined tryptophan-containing quasi-repeat previously noted in segment 5. There are no other evident repeats and the relatively low I4 value of 0.73 may be insufficient to stabilize a single-stranded α-helix. A folded rather than extended conformation of indeterminate net length may result. In contrast, however, the charged/apolar ratio is still high and is more compatible with a conformation with an appreciable axial ratio. Thus, there is some difficulty in assigning a likely structure to this segment. Different conformations are likely to result under different conditions.

(8) Residues 1250–1849 consist of an almost uninterrupted stretch of α-helix configured as an irregular consensus 26 residue repeat (Table 3); many of the repeats are actually 24 residues long and about half are much shorter, containing only about 16 residues. The sequence RQERDRKFREEEQ (SEQ ID NO:19) is the common conserved element. Again, these repeats are characterized by long stretches in which oppositely charged residues would interface each other on alternate turns of an α-helix. Interestingly, elements of a 7.7–7.9 residue repeat of very high probability are evident in glutamate and lysine+arginine residues (Table 3), suggestive of a spiral of charged residues about the α-helix of the general type described above for segment 6. The very high I4 value of 1.86 and the high charged/apolar ratio (3.72) favor the formation of an elongated single-chain α-helical rod of length about 90 nm.

(9) Residues 1850–1897: The carboxyl-terminal sequences are likely to adopt a folded or random coil conformation, due to the presence of prolines and glycines. Interestingly, the terminal 20 residues have been precisely conserved between sheep (5) and human, and have afforded the manufacture of a TRHY-specific antibody (Hamilton, E. H., et al., *J. Invest. Dermatol.* 98:881–889 (1992)).

The net overall length of human TRHY is thus estimated to be at least 215 nm, arising from several distinct elongated rods. Segments 1 and 9 represent the globular amino- and carboxyl-terminal domains respectively whereas segments 5 and 7 occur within the rod domain but have α-helix-rich structure of indeterminate net length. It is possible that the human TRHY molecule in vitro (and possibly in vivo as well) folds about domains 5 and 7, and forms a rod of about 100 nm with a knob of 15–20 nm (that is, half of the length of domain 6) at the bend. This value compares with the approximate 85 nm long rod with a 12 nm bead on one end as visualized for native pig TRHY by shadowing electron microscopy (Hamilton, E. H., et al., *J. Invest. Dermatol.* 98:881–889 (1992)). Such a folded structure, consisting of antiparallel α-helices, conceivably could be stabilized by ionic interactions between the many charged residues along the equal-length segments 2+3+4 and 8. It remains unclear, however, whether human TRHY is folded in half in vivo (as seen in the in vitro preparations studied by electron microscopy) or whether it is a single α-helix at least 215 nm long.

4. Trichohyalin is a Functional Calcium Binding Protein

Figure 8:
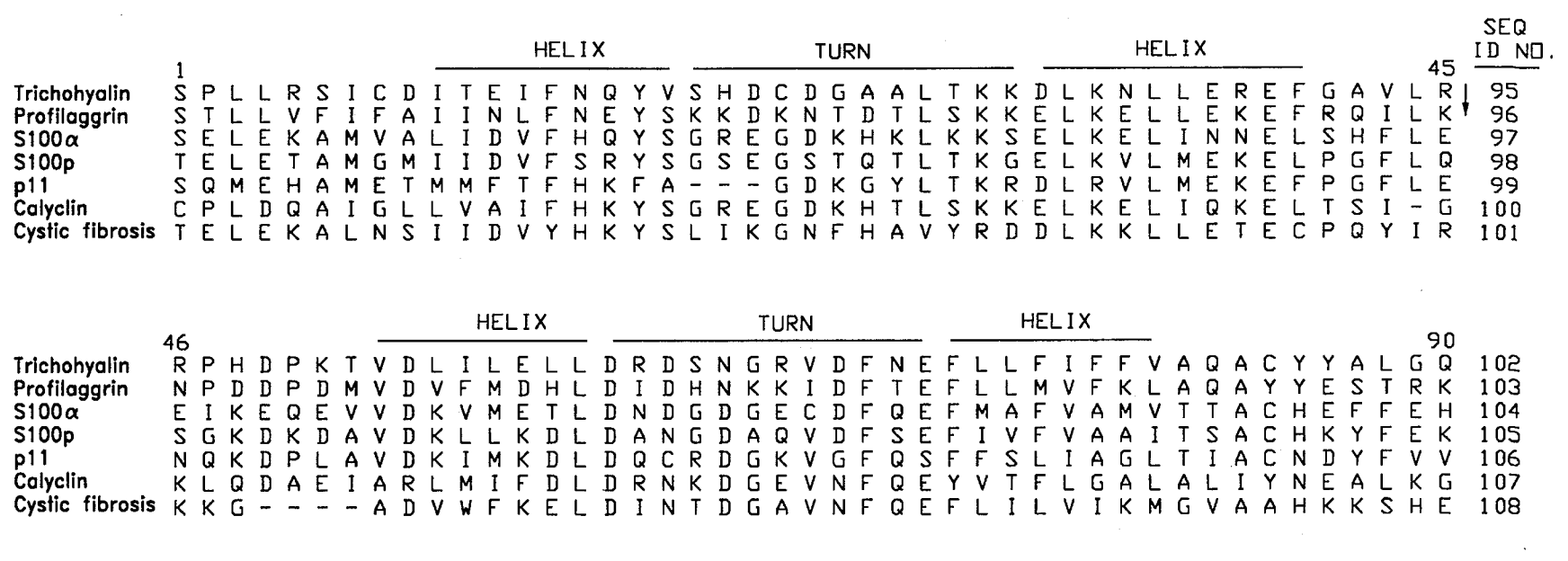
Figures 9A, 9B:
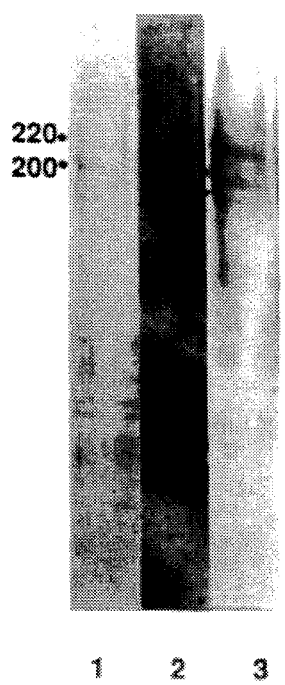
FIG. 9A is a picture of pig TRHY which as been electrophoresed on a polyacrylamide gel. This picture reveals two bands of about 220 and 200 kDa that can be stained with coomassie blue (lane 1), and can also be detected by $^{45}$Ca binding (lane 2) or by use of a specific carboxyl-terminal epitope antibody (lane 3).
FIG. 9B is a dot blot for quantitating $^{45}$Ca binding. The indicated proteins (1–10 µg) were applied and incubated with $^{45}$CaCl$_2$. The first lane of numbers describes a quantitative value determined by scanning densitometry. In the second lane, these values have been scaled in relation to calmodulin (1.00) as $^{45}$Ca binding/mol.

The sequence data of FIG. 3 and sequence homology data of FIG. 8 indicate the presence of two well-defined calcium binding domains of the EF-hand type. Prior to the present invention, methods were not described for the isolation of human epidermal or hair follicle TRHY. However, we show in FIG. 9A that pig tongue TRHY is capable of binding $^{45}$Ca in vitro (lane 2). Interestingly, unlike human, pig TRHY appears as two bands of about 220 and 200 kDa (lane 1), both of which bind calcium (lane 2). In addition, a Western blot using a new TRHY antibody (Hamilton, E. H., et al., *J. Invest. Dermatol.* 98:881–889 (1992)) elicited against the carboxyl-terminal 18 amino acids, which have been precisely conserved between human and sheep and presumably in pig TRHY as well, also reveals two bands of the same sizes (FIG. 9A, lane 3). Since these data indicate that the amino- and carboxyl-terminal ends have been conserved, this means that pig TRHY is expressed as two distinct protein products. By slot blotting (FIG. 9B), we show that pig TRHY (about 210 kDa, 2 EF-hands/mol) binds $^{45}$CaCl$_2$ as effectively as calmodulin (14 kDa, 4 EF-hands/mol). Profilaggrin binds calcium somewhat more efficiently (Kozak, M. (1989), *J. Cell Biol.* 108, 229–241). Most of the calcium binding in the total epidermal extract is presumably due to the profilaggrin.

C. Description of Human Trichohyalin

1. Human Trichohyalin is a Long Segmented Rod-Shaped Molecule That Has the Potential to Interact with Keratin Intermediate Filaments The human TRHY protein is unique in possessing the highest known content of charged residues. By use of secondary structure prediction and FFT analyses, we show that it consists of 9 well-defined domains. The bulk of the sequences, defined by domains 2, 3, 4, 6 and 8, are very highly charged, configured as a series of peptide repeats of varying degrees of regularity, which adopt an α-helical configuration. A point of great significance here is that the α-helix-rich segments do not have a heptad substructure characteristic of all α-fibrous proteins that form a two- or three-stranded coiled-coil conformation (Cohen, C. and Parry, D. A. D., *Proteins: Structure, Function and Genetics* 7:1–15 (1990)). In each of the α-helical domains, there are well-defined regularities in the disposition of charged residues so that oppositely-charged residues frequently lie on alternate turns of the α-helix, thereby stabilizing the α-helix by intrachain ionic salt bonds. Indeed the very high ratio of charged to apolar residues and the number of intrachain ionic interactions per seven residues (I4 values, see Table 3), are characteristic of a stable single-stranded α-helical configuration (see, e.g., Kligman, D. and Hilt, R. H., *Novel Calcium-Binding Proteins*, Heizman, C. W., ed., Springer-Verlag, Berlin, 65–103 (1991)). In addition, the very large numbers of polar glutamine residues are to be expected to further contribute to this α-helical structure by H-bonding. Nevertheless, each of these domains is interrupted by an occasional proline residue which is therefore likely to introduce bends or kinks along their length (FIG. 7). More importantly, domains 5 and 7 have distinct and unusual features. While they still contain important elements of the other domains with respect to high α-helix content and high charged/apolar residue ratios, they are likely to adopt a more complex conformation due not only to the presence of multiple prolines, but also to multiple tryptophan and other residues that favor the introduction of turns and even limited sheet structures. Our conclusion is that these regions promote folds in the human TRHY structure. Domains 2+3+4 (total length about 89 nm) and 8 (length about 90 nm), could fold back on each other, hinged about domains 5 and 7, and stabilized by the potential to form many ionic salt bonds across the two arms of the molecule. This would create a molecule about 100 nm long with a knob of 15–20 nm comprising segments 5, 6 and 7. This model is generally consistent with existing data. Native pig TRHY is about 85–90 nm long and possesses a 12–15 nm bead on one end. Pig TRHY is about 15% smaller than human TRHY, but possesses functional calcium binding domains (FIG. 9) and a conserved carboxyl-terminal domain 9.

Our calculations show that unfolded human TRHY is at least 215 nm long in toto, and perhaps as much as 260 nm (including length contributions of domains 5 and 7, but not 1 and 9). This length is the same as the range of the periodicities of interaction of TRHY with KIF in inner root sheath cells (see, e.g., O'Guin, W. M., et al., *J. Invest. Dermatol.* 98:24–32 (1992)). Thus, it appears that TRHY constitutes an elongated, somewhat flexible crosslinking IFAP in these cells. Based on these analyses, it is clear that the likely secondary structure of human TRH is different from an intermediate filament (IF) chain. Such proteins are characterized by a well-defined central α-helical rod domain, the sequences of which form a two-chain segmented coiled-coil motif.

Of the α-helical domain segments, domain 6 is the most regular with eight near-exact 30 residue repeats (see FIG. 6) but it nonetheless possesses unusual features. The glutamic acid, arginine and leucine residues are each configured as a quasi-repeat of about 7.5 residues (that is, 30/4) (Table 3), corresponding to slightly more than two turns of the α-helix (3.6 residues/turn). A similar repeat is also evident to some extent in domain 8. Thus while many of the positive and negative charges will form stable ionic interactions, the net result will be a slow spiral of charged residues around the axis of the α-helix. While the pitch length of this spiral is critically dependent on the number of residues per turn in the α-helix, a length of 14 nm seems likely.

The 1B and 2 rod domain segments of intermediate filament chains possess a 9.8 residue periodicity in the linear distributions of charged residues. This is equivalent to a linear rise of the coiled-coil of approximately 1.4 nm, or one-tenth of the periodicity of domain 6. Accordingly, by formation of periodic ionic interactions of the charged residues on the IF rod domain segments with the highly ordered domain 6 (and perhaps also with domain 8), human TRHY could function as an IFAP in the epidermis and inner root sheath cells.

Human TRHY has 332 glutamine and 104 lysine residues, which are potential targets for crosslinking by transglutaminases. Earlier peptide sequencing data suggested the presence of numerous isodipeptide crosslinks in both inner root sheath and medulla proteins. In the case of the inner root sheath, many of these involved the non-α-helical end domain sequences of the KIF of the cells, perhaps because of accessibility, and are likely to involve interchain links between the TRHY and KIF.

Early amino acid composition and sequencing data showed that in the mature inner root sheath and medulla proteins of the guinea pig hair follicle, approximately 25% and 40–50%, respectively, of the arginines are converted to citrullines by desimidation. We estimate that conversion of 200 or more arginines to citrullines will lower the pl of the intact human TRHY protein to about 4. Similarly, a significant although unknown number of lysines will be effectively discharged by the formation of the isodipeptide crosslinks. Since the arginines and lysines lie on the periphery of the α-helix, they will be readily accessible by the peptidyl arginine desimidase and transglutaminase(s) enzymes. This discharging of many basic residues will likely interfere with the formation of ionic salt bonds responsible for stabilizing the single-stranded α-helix. Conversion of 200 arginines will lower the charged/apolar ratio substantially, effectively destabilizing the structure. Accordingly, we predict that TRHY becomes a much less regularly-organized molecule upon postsynthetic modification.

2. Trichohyalin is a Functional Calcium Binding Protein

The amino acid sequence information provided by the nucleic acid sequence of trichohyalin has revealed the surprising finding of a pair of calcium binding domains on the TRHY molecule. These domains are of the EF-hand type, typically found in small S100-like calcium binding proteins (FIG. 3,8,9). TRHY and the S100 proteins share significant homology with each other at the level of gene structure: their transcribed sequences consist of three exons, of which the first consists of 5'-non-coding sequences; the second contains the initiation codon and first EF-hand motif; and the third exon contains the second EF-hand motif, as well as the remainder of the coding sequences. Moreover, the locations of the exon/intron boundaries of human TRHY and the S100 proteins have been precisely conserved. In addition, we have recently discovered that human profilaggrin also contains two EF-hand motifs at its amino terminus that are organized at the protein and gene levels in an identical fashion to the S100 class and to the human TRHY gene. The experiments of FIG. 9 for pig TRHY and other experiments with human profilaggrin (Markova, N., et al., *Mol. Cell Biol.* 13:167–182 (1993)), have revealed that these EF-hand motifs in the two proteins are in fact functional in binding calcium in vitro. Therefore, it seems likely that human TRHY is a functional $Ca^{2+}$ binding protein in vivo.

The most notable difference between TRHY and the S100 class of proteins is the size and nature of the amino acid sequences beyond the EF-hand motifs. Most members of the S100 class of proteins possess only short sequences flanking the second EF-hand motif and share little overt sequence homology with one another. These sequences are thought to be involved in $Ca^{2+}$-mediated interactions with different target effector molecules. In contrast, the human TRHY sequences extend for more than 1700 residues, largely configured in a series of quasi-repeating peptides. Moreover, as discussed, these sequences are subjected to at least two different types of postsynthetic modifications that are calcium dependent: certain lysin donor and/or glutamine acceptor residues become involved in the formation of $N^{\epsilon}$-(λglutamyl)lysine isodipeptide crosslinks catalyzed by transglutaminases (6,10,11); and many arginines are converted to citrullines by the enzyme peptidylarginine deiminase (12–16). It seems likely, therefore, that the calcium binding properties of the EF-hand motifs are involved in these post-translational reactions.

II. Human Transglutaminase-3

Another discovery of the present invention is the structure and sequence of human and mouse TGase3. As described herein, the mouse and human protransglutaminase-3 enzymes contain 692 amino acids of calculated molecular weight about 77 kDa. While these proteins share 38–53% identity to other members of the transglutaminase family, the mouse, human, and guinea pig enzymes surprisingly have not been highly conserved and show only 50–75% identity to each other. Much of the sequence variation occurs in the vicinity of the proteolytic activation site which lies at the most flexible and hydrophilic region of the molecule and is flanked by a sequence of 12 residues that are absent from all other transglutaminases. Cleavage of this exposed flexible hinge region promotes a conformational change in the protein to a more compact form resulting in greatly increased enzymic activity. Expression of mouse and human transglutaminase-3 mRNA is regulated by calcium, as with other late differentiation products of the epidermis, suggesting that this enzyme is responsible for the later stages of cell envelope formation in the epidermis and hair follicle.

Methods Used to Determine the Sequences of Human and Mouse TGase3

1. Determination of the Amino Acid Sequences of Selected Peptides of Guinea Pit TGase3

The 50 kDa amino-terminal and 27 kDa carboxyl-terminal fragments of guinea pig TGase3, derived by dispase treatment, were fractionated and purified as described by Kim, H.-C., et al., *J. Biol. Chem.* 265:29171–21978 (1990). Each portion was cleaved with trypsin (Boehringer sequencing grade, Boehringer Mannheim Biochemicals, Indianapolis, Ind.) at 10 mg/ml in 0.1M $NH_4HCO_3$ with a final enzyme to protein ratio of 1:50 and digested for a total of 4 h at 37° C. Following drying, the peptides were redissolved in 0.1% aqueous trifluoroacetate, fractionated by HPLC (High Pressure Liquid Chromatography). Well-resolved peaks with absorbances at both 210 nm and 350 nm were then selected for sequence analysis. Absorbance at 350 nm was taken as an indication of cysteine residues alkylated with 5-N [(iodoacetidoethyl)amino]naphthalene-1 sulfonic acid, possibly corresponding to active-site peptides. Sequence analysis of selected peptides was then performed on an Applied Biosystems 470A protein sequenator (Applied Biosystems Inc., Foster City, Calif.) using the automated Edman degradation method (see Kim, H.-C., et al., *J. Biol. Chem.* 265:29171–21978 (1990); Hohl, D., et al., *J. Biol. Chem.* 266:6626–6636 (1991); and Hewick, R. M., et al., *J. Biol. Chem.* 256:7990–7997 (1981)).

2. Anchored-PCR Cloning Strategies

Once the sequences of the selected guinea pig peptides were obtained, we set out to determine the sequence of mouse TGase3. The strategy for obtaining mouse TGase3 is thus set forth below. However, a very similar strategy was then carried out to identify human TGase3. Rather than repeat the common steps of the protocols for obtaining mouse and human TGase3, the protocol for obtaining mouse TGase3 will be set forth in detail below, and the steps taken to obtain the sequence of human TGase3 which differ from those taken to obtain mouse TGase3 will be pointed out.

Initially, we constructed a series of degenerate oligonucleotide primers based on the available guinea pig TGase3 peptide sequences (see Table 4 for lists of sequences from which primers were prepared) and used these to amplify DNA obtained from a random-primed cDNA library prepared from mouse epidermal mRNA (Roop, D. R., et al., *Proc. Natl. Acad. Sci. U.S.A.* 80:716–720 (1983)). In obtaining human TGase3, a cDNA library prepared from human epidermal mRNA was prepared by the same method.

PCR was performed with a commercial DNA amplification reagent kit (from Perkin-Elmer Cetus, Norwalk, Conn.) by following the manufacturer's specifications, using 25 pmol of primers and with conditions of: 95° C. (5 min), and 35 cycles of denaturation at 94° C. (0.5 min), annealing at 42° C. (0.5 min) and elongation at 72° C. (1.5 min). The PCR products were fractionated through low-melting agarose, excised, and purified through Chroma spin 100 columns (Clontech, Palo Alto, Calif.). The ends of the amplified DNA were filled in with Klenow DNA polymerase (see Sambrook, J., Fritsch, E. F. and Maniatis, T., *Molecular Cloning: A Laboratory Manual,* Cold Spring Harbor Press, Cold Spring Harbor, N.Y. (1989)), subcloned into the pGEM 3z vector (Promega Corp., Madison, Wis.), and then sequenced by the dideoxy chain termination method with Sequenase 2.0 (United States Biochemical Corp., Cleveland, Ohio). Although most sets of degenerate primers did not work, apparently because of the substantial nucleotide sequence differences between guinea pig and mouse TGase3 mRNAs (see Table 9), four were found sufficiently useful to proceed.

Subsequently, RNA mediated anchored PCR was used to "walk" in both directions along the mouse TGase3 mRNA by using specific mouse TGase3 nucleotide sequences as primers and by using additional degenerate primers. Aliquots of 200 ng of DNase 1-treated total newborn mouse epidermal RNA (Roop, D. R., et al., *Proc. Natl. Acad. Sci. U.S.A.* 80:716–720 (1983)) were reverse transcribed at 42° C. In obtaining human TGase3, a lambda-gtll cDNA library prepared from newborn human foreskin was similarly reverse transcribed.

Following removal of the dNTPs through Chroma spin columns, the cDNAs so produced were tailed in the presence of 200 µM dGTP with 25 units of terminal deoxytransferase (Gibco-Bethesda Research Laboratories Inc., Gaithersburg, Md.) for 1 h at 37° C. (Sambrook, J., Fritsch, E. F. and Maniatis, T., *Molecular Cloning: A Laboratory Manual,* Cold Spring Harbor Press, Cold Spring Harbor, N.Y. (1989)). PCR was then done in two steps. The conditions for the first round were exactly as described above, with 25 pmol of the primer used as the minus primer, and either a degenerate primer, a specific mouse TGase3 primer, or oligo-dC as the plus primer (when identifying human TGase3, a specific human primer was used instead of the specific mouse primer). These specific primers are listed in Table 5 below.

A portion of the PCR reaction mixture was diluted 1:1000 with buffer and 1 µl was reamplified in a second round of PCR using the more stringent conditions of: denaturation at 94° C. (0.5 min), annealing at 55° C. (0.5 min) and elongation at 72° C. (1.5 min), and using primers on one end that were nested inside those used in the first PCR reaction (see Table 5, FIG. 10). The further subcloning and sequencing procedures were performed as above. In this way, it was possible to "walk" along the entire length of the mouse TGase3 mRNA in both directions in six steps. The human TGase3 cDNA sequence was generated in essentially the same way using the nested primers listed in Table 5 and using the adduced mouse sequence data.

The result of these procedures was the discovery of the DNA coding sequences for human TGase3 (SEQ ID NO:LLL) and mouse TGase3 (SEQ ID NO:QQQ). As is known to those of skill in the art, a purified molecule of DNA containing the mouse or human TGase3 coding sequence can also be synthesized by probing mRNA from mouse or human epidermal tissue, respectively, with a probe specific to either mouse or human TGase3 (see Table 5), extending that probe with a DNA polymerase such as the Klenow fragment of *E. coli,* and then isolating the resulting DNA strands produced. Desirably, such strands are then subcloned into a vector such as a plasmid reproducible in *E. coli*.

Once the coding sequences of human and mouse TGase3 were known, it also became possible to produce further probes for these sequences. Such probes are designed by selecting 20 consecutive nucleic acids from the coding sequences of either SEQ ID NO:LLL or SEQ ID NO:QQQ and can be synthesized by various means known to the art, including the use of automated DNA synthesizers. These probes can be used, for example, to identify TGase3 in the mRNA or genomic DNA of cells or cell cultures.

3. Northern Blotting Procedures

Total cellular RNA was prepared from human foreskin epidermis (Steinert, P. M., et al., *J. Biol. Chem.* 260:7142–7149 (1985)), newborn BALB/c mouse epidermis (Roop, D. R., et al., *Proc. Natl. Acad. Sci. U.S.A.* 80:716–720 (1983)), and human and mouse keratinocytes grown to confluence in the presence of low (0.1 mM) or high (0.6 mM) $Ca^{2+}$ (see Yuspa, S. H., et al., *J. Cell Biol.* 109:1207–1217 (1989) and Hohl, H., et al., *J. Invest. Dermatol.* 96:414–418 (1991)). RNA from the hair follicles of 5 day old mice was also isolated. Northern gels using denaturing conditions were loaded with 25 µg of total cellular RNA, performed as described in Yaminishi, K., et al., *J. Biol. Chem.* 267:17858–17863 (1992), and calibrated with standard RNA size markers (Gibco-BRL, Gaithersburg, Md.).

Northern slot blots were then prepared as described in Sambrook, J., Fritsch, E. F. and Maniatis, T., *Molecular Cloning: A Laboratory Manual,* Cold Spring Harbor Press, Cold Spring Harbor, N.Y. (1989). In this case, the blots were calibrated with 10, 1.0, 0.1, 0.01 fmol amounts of probes encoding the full-length TGase1 (Kim, H.-C., et al., *J. Biol. Chem.* 266:536–539 (1991)), a 0.9 kbp PCR fragment of 3'-non-coding region for TGase3 (SEQ ID NO:53) and a 0.7 kbp 3'-non-coding region of the published sequences of TGase2 (Gentile, V., et al., *J. Biol. Chem.* 266:478–483 (1991)) (see Table 5 for the two primers used). Aliquots of 10 µg of the several RNA samples were tested separately with the three TGase specific probes. All Northern filters were washed with a final stringency of 0.5×SSC at 65° C. for 30 min. The resulting X-ray films were exposed for varying amounts of time in order to facilitate quantitation of the abundance of the specific mRNAs by densitometry.

4. Computer Analyses of Sequences

Nucleic acid and protein sequence homologies were performed using the University of Wisconsin software packages compiled by the Wisconsin Genetics Computer Group (Devereux, J., et al. *Nucleic Acids Res.* 12:387–394 (1984)), the IBI Pustell sequence software (version 3.5, International Biotechnologies Inc.) and Geneworks sequence software (Intelligenics Inc.), based on published algorithms (see Chou, P. Y. and Fasman, G. D., *Biochemistry* 13:222–245 (1974); Garnier, J., et al., *J. Mol. Biol.* 120:97–118 (1978); and Pearson, W. R. and Lipman, D. J., *Proc. Natl. Acad. Sci. U.S.A.* 85:2444–2448 (1988)).

B. Results of Search for Human and Mouse TGase3

Our initial attempts to locate clones for either mouse or human TGase3 in available λgt11 libraries using low-stringency hybridizations with TGase1 or TGase2 probes or active-site probes (Kim, H.-C., et al., *J. Biol Chem.* 266:536–539 (1991)) were unsuccessful, perhaps because of low mRNA levels. Accordingly, we made TGase3-specific degenerate oligonucleotide probes derived from the amino acid sequences of tryptic peptides of TGase3 isolated from guinea pig epidermis. The implicit assumption was that the guinea pig, mouse and human TGase3 proteins would share high degrees of sequence homology, as found for the TGase1 and TGase2 systems.

1. Amino Acid Sequences of Guinea Pig TGase3 Tryptic Peptides

Although the 27 kDa fragment resulting from dispose treatment yielded a clean amino acid sequence for 28 cycles corresponding to its amino-terminus and the activation site of proteolytic cleavage, no useful information on the larger catalytic 50 kDa portion was obtained. Accordingly, using larger quantities, both peptide portions were cleaved to completion with trypsin. Selected well-resolved peptides, especially those containing cysteine residues, were chosen for sequencing. In this way, sequences from a total of 12 tryptic peptides (six from each of the 50 kDa and 27 kDa portions) and the amino-terminus of the 27 kDa portion were obtained (Table 4). These represented 180 sequenced residues, or about 25% of the total protein. Peptides 1 and 3 (order 3-1) are recognizable as constituting the active site region, based on comparisons with the known sequences of the TGase family members. The amino acid substitutions in this active site region in relation to the other family members are diagnostic for the TGase3 system (see Table 7 below).

Figure 10:
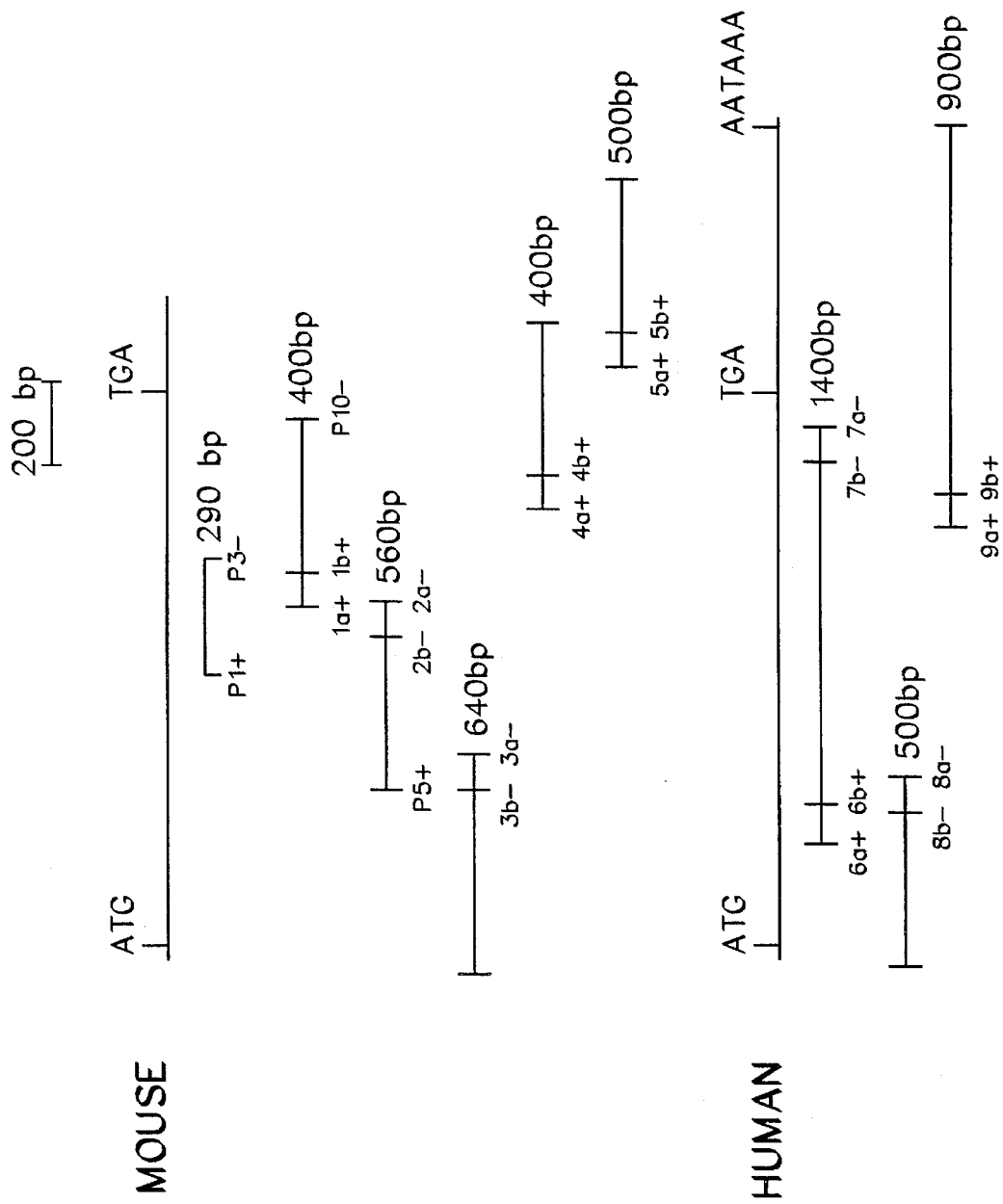
FIG. 10 illustrates the strategy employed in generating the nucleotide information of the mouse TGase3 enzyme (SEQ ID NO:111) and human TGase3 enzyme (SEQ ID NO: 112). In each case, the upper line represents the full-length sequence showing the initiation, termination and polyadenylation signal sequences. Below are shown bars displaying the primers used (primer sequences are listed in Table 5) and the extent of sequence information obtained with each PCR step.

2. Cloning by Anchored-PCR and Deduced Amino Acid Sequences of Mouse and Human TGase3 Proteins Degenerate oligonucleotide probes based on the above amino acid sequences of guinea pig TGase3 failed to identify positive-clones in available mouse or human λgt11 cDNA libraries. However, when such oligonucleotides were employed in primer extension experiments with poly(A)-enriched RNA from newborn mouse or human foreskin epidermis, weak signals corresponding to the presumed size of the TGase3 mRNAs (Kim, H.-C., et al., *J. Biol. Chem.* 266:536–539 (1991)) were found. Therefore, we used the oligonucleotide primers to amplify by PCR the DNA extended by primer P3-(Table 5). One pair of primers (P1+P3−; FIG. 10, Table 5) yielded a product of 292 bp, and was subcloned into pGEM-3z. About 5% of such clones contained TGase-like sequences, including the active site region, which were identical to peptides 3+1 of the available guinea pig tryptic peptides (Table 4). This finding afforded confidence that we were indeed amplifying the mouse TGase3 mRNA system. Accordingly, we used this exact sequence data to extend the mouse TGase3 sequence by use of RNA-mediated anchored PCR as described above. First, we used one set of specific nested primers and another degenerate primer from the guinea pig peptide information (1a+/P10− and 1b+/P10−; P5+/2a- and P5+/2b-) (FIG. 10, Table 5). The remainder of the 5'-end up to the capsite was recovered by primer extension, tailing with dG, and PCR amplification in two steps with nested primers (3a-/oligo-dC; then 3b-/oligo-dC) (FIG. 10). The 3'-end sequence information was recovered in two steps by use of primer extension with a random hexamer, followed by tailing with dG. The cDNA products were amplified by PCR in two steps with two sets of nested primers (4a+/oligo-dC; then 4b+/oligo-dC) and (5a+/oligo-dC; then 5b+/oligo-dC) (FIG. 10, Table 5).

The human TGase3 sequence was generated in essentially the same manner in three steps, except that an oligo-dT primer was used to generate the full-length 3'-non-coding information. The primers (see Table 5) and strategy used are outlined in FIG. 10.

A series of further RNA-mediated anchored PCR experiments was performed using primers that crossed over those shown in FIG. 10 and in Table 5 in order to confirm and check the sequences for PCR-induced sequence mutations (lists of primers used are not shown). The natures of 7 ambiguous nt were resolved in additional PCR experiments.

The available nucleotide sequence information consists of 2297 nt for mouse, including the entire 5'-non-coding information, but incomplete 3'-non-coding sequences (FIG. 10). The human data extends for 2645 nt, and is assumed to be near full-length because of the inclusion of the polyadenylation signal sequence (FIG. 11); thus, its estimated mRNA size is about 2.8 kb. In both cases, there is an open reading frame of 2079 bp, so that both proteins contain 692 amino acids of calculated molecular weight of 77.1 kDa (mouse) and 76.6 kDa (human), which are very close to the values adduced for guinea pig TGase3 by analytical ultracentrifugation and SDS-polyacrylamide gel electrophoresis experiments (see Negi, M., et al., *J. Invest. Dermatol.* 85:75–78 (1985) and Kim, H.-C., et al., *J. Biol. Chem.* 265:29171–21978 (1990)). Interestingly, mouse TGase3 is near neutral in charge (pl 6.5) compared to human TGase3 (pl 5.6), findings that are also consistent with earlier chromatographic observations.

3. Abundance and Expression of Mouse and Human TGase3 mRNAs

Figure 12A:
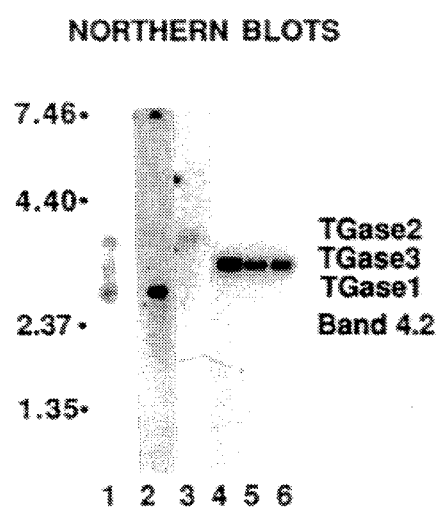
FIG. 12A is a picture of an X-ray film exposure of Northern blots depicting the sizes of human and mouse TGase3 mRNAs. Aliquots of 25 µg of total cellular RNA from human foreskin epidermis (lanes 1–4), newborn mouse epidermis (lane 5) or five day old mouse hair follicles (lane 6) were probed with: lane 1, a 58 nt antisense degenerate oligonucleotide encoding active site sequences (see Kim, H.-C., et al., *J. Biol. Chem.* 266:536–539 (1991) and Sambrook, J., Fritsch, E. F. and Maniatis, T., *Molecular Cloning: A Laboratory Manual.*, Cold Spring Harbor Press, Cold Spring Harbor, N.Y. (1989)); lane 2, a 175 bp 3'-non-coding probe of a TGase1 cDNA clone; lane 3, a 0.7 kbp 3'-non-coding portion of TGase2 generated by PCR (see Table 5); lanes 4–6, a 1 kbp cDNA probe encoding 3'-non-coding sequences of human TGase3 (see FIG. 10). The individual strips were exposed for: lane 1, 14 d; lane 2, 2d; lane 3, 4d; lanes 4–6, 23d. Positions of migration of RNA size markers are shown to the left of the lanes.

A series of cDNA probes containing specific 3'-non-coding sequence information for human TGase1 (Kim, H.-C., et al., *J. Biol. Chem.* 266:536–539 (1991)), TGase2 (generated by PCR; see Table 5 and Gentile, V., et al., *J. Biol. Chem.* 266:478–483 (1991)), and TGase3 (generated with PCR primers 6a+/6b, Table 5), were used to separately test human foreskin RNA on Northern blots (FIG. 12A). Four distinct bands are seen with a degenerate oligonucleotide probe (Kim, H.-C., et al., *J. Biol. Chem.* 266:536–539 (1991)) for active site sequences (lane 1), which correspond to the four known TGase-like activities expressed in the epidermis. The TGase3 probe SEQ ID NO:53 identified only the central mRNA species of about 2.9 kb (lane 4). This is consistent with the size of the TGase3 mRNA adduced from the above sequencing data. Furthermore, it is now known that the mRNA encoding TGase 2 is the largest (about 3.4 kb, lane 3) and that encoding TGase1 is smaller (about 2.7 kbp, lane 2). The fourth and smallest band of about 2.4 kb corresponds to the mRNA for band 4.2 (Korsgren, C., et al., *Proc. Natl. Acad. Sci. U.S.A.* 87:613–617 (1990)). Mouse epidermis and hair follicles also express a TGase3 mRNA species of the same size as human TGase3 mRNA (FIG. 12a, lanes 5,6), consistent with the biochemical data which suggests that the epidermal and hair follicle TGase3 pro-enzymes are in fact the same gene product (Kim, H.-C., et al., *J. Biol. Chem.* 265:29171–21978 (1990)). These highly specific probes displayed almost no cross-hybridization. The data therefore confirm the identity of the TGase3 probes.

Figure 12B:
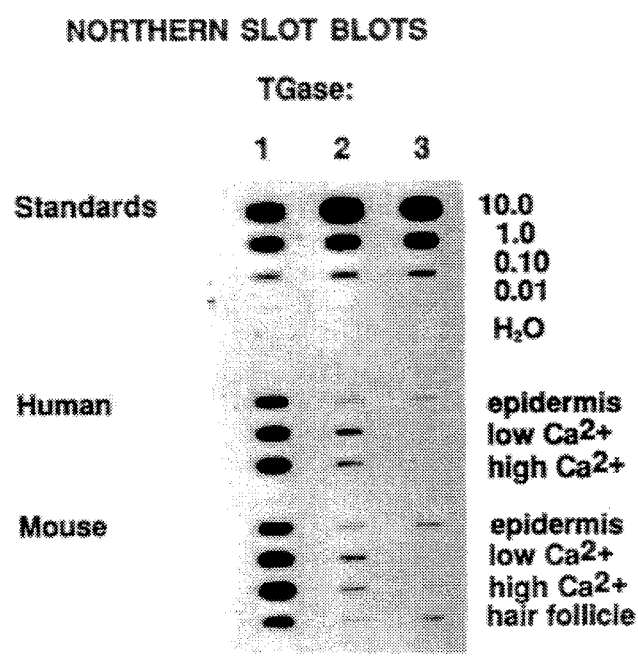
FIG. 12B is a picture of an X-ray film exposure of Northern slot blots in which aliquots of 10 µg of RNA from the sources shown (TGase1, TGase2, and TGase3) were probed with the above TGase-specific probes. For quantitation purposes (see Table 6), the X-ray films were exposed for several different times; this figure shows one exposure (for 6d) only.

Using slot blotting techniques, we also examined the expression characteristics of these mRNA species (FIG. 12B). By using specific cloned probes as calibra2tion standards for each TGase species to account for variations in hybridization and labeling efficiencies, we could estimate the amounts of each species expressed in intact epidermis, hair follicles or cultured cells (Table 6). Whereas the TGase1 and TGase2 mRNAs are unregulated in submerged liquid cultures, TGase3 mRNA is greatly diminished and essentially absent in low $Ca^{2+}$ medium conditions. Furthermore, TGase3 expression is modestly up-regulated in media containing near-optimal levels of $Ca^{2+}$, whereas the former two species are down-regulated. Thus, the TGase3 system is regulated differently from the TGase1 and TGase2 enzymes. These data establish that the TGase3 system is regulated in the same general way as other late epidermal differentiation products such as loricrin, profilaggrin, and keratins 1 and 10. These data also support the view that the TGase3 enzyme is involved in a later stage of CE formation or assembly than the TGase1 enzyme.

The data of Table 6 also show that in intact epidermis, the level of TGase1 mRNA is about 5–7 times greater than that of TGase3. While little information is currently available on the turnover rates or rates of translation of these mRNAs (compare Michel, S., et al., *J. Invest. Dermatol.* 98:373–378 (1992) with Schroeder, W. T., et al., *J. Invest. Dermatol.* 99:27–34 (1992) for TGase1), our present data imply that TGase1 is a more abundant enzyme in epidermis than TGase3. Nevertheless, activated TGase3 appears to constitute about 75% of total epidermal TGase enzymic activity (Kim, H.-C., et al., *J. Biol. Chem.* 265:29171–21978 (1990)). Therefore, it seems possible that the specific activity of TGase3 enzyme is higher than TGase1.

4. Amino Acid Sequences of the Human, Mouse and Guinea Pig TGase3 Proteins Are Not Highly Conserved In Table 7 are listed the several tryptic peptides generated for guinea pig TGase3 that were found in the mouse and human TGase3 sequences. The comparisons further extend confidence for the correct identity of these sequences. In addition, the availability of the amino-terminal information of the 27 kDa fragment formed on proteolytic cleavage activation enabled identification of the activation region in the mouse and human TGase3 proteins as well (Table 7).

Previous studies have shown that the sequences of human and mouse TGase1 and TGase2 enzymes have been very highly conserved: sequences show identities of about 93% and homologies of about 97%. In contrast, the data of FIG. 11 reveal that mouse and human TGase3 sequences have deviated more widely (Table 8). Overall, the sequences show 75% identity and 84% homology, with the 27 kDa fragment generated following proteolytic activation somewhat less conserved: 71% identity and 81% homology. Interestingly, the amino acid sequences of the available tryptic peptides of the guinea pig TGase3 show far more variation from mouse and human such that the 27 kDa fragment displays as little as 45% sequence identity in available comparable sequences. Most of the variations have occurred in the vicinity of the proteolytic activation site, which may mean that the different species have evolved alternate mechanisms for proteolytic activation of the TGase3 pro-enzyme. These sequence variations can account for the difficulties we initially encountered in generating mouse and human sequence information using the guinea pig data.

5. Comparisons Show that Human TGase3 is Distantly Related to Other Members of the TGase Family Human and mouse TGase3 proteins are notably different from the other four TGase-like proteins by the net insertion of approximately 12 highly polar residues at the side of proteolytic activation. Overall homology and identity scores between the five TGases are shown in Table 8. The sequences were aligned to maximize homologies according to the protocol of Pearson and Lipman (Pearson, W. R. and Lipman, D. J., *Proc. Natl. Acad. Sci. U.S.A.* 85:2444–2448 (1988)). We have chosen to analyze only sequences bounded by conserved intron locations identified previously (Kim, I.-G., et al., *J. Biol. Chem.* 267:7710–7717 (1992)), which presumably delineate the conserved structural regions of the TGases. Each TGase chain deviates widely as its termini in both sequence and length, which thus does not admit meaningful comparisons. The human TGase3 protein is most closely related to TGase1 and TGase2, and more similar to band 4.2 than factor XIIIa, although band 4.2 is least related to the other TGases.

Figure 14A:
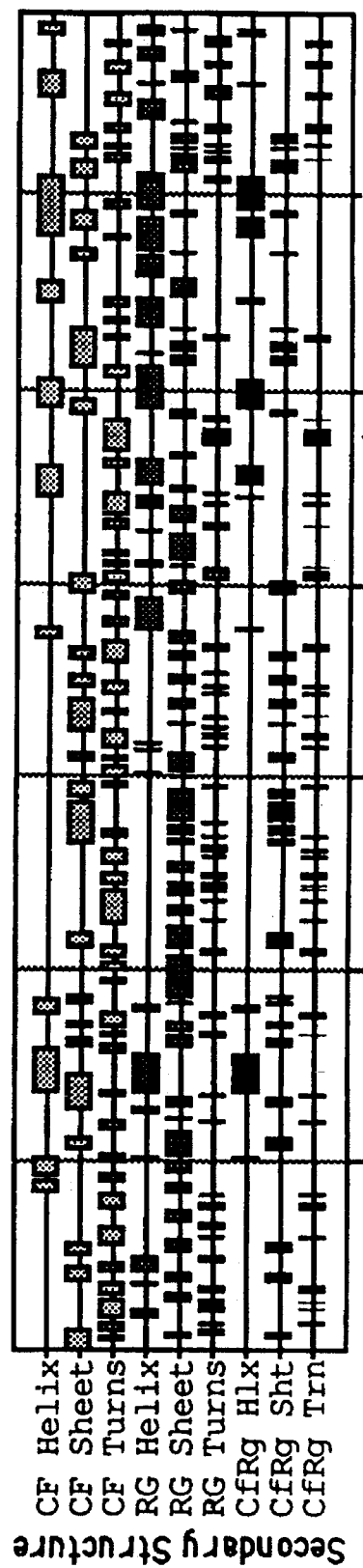
FIG. 14 shows three charts which show the predicted structural features of human TGase3. The charts were produced using the IBI Pustell and Intelligenics Geneworks software packages and are based on known analytical methods (see Devereux, J., Haeberli, P. and Smithies, O., *Nucleic Acids Res.* 12:387–394 (1984); Chou, P. Y. and Fasman, G. D., *Biochemistry* 13:222–245 (1974); Garnier, J., et al., *J. Mol. Biol.* 120:97–118 (1978); and Pearson, W. R. and Lipman, D. J., *Proc. Nail Acad. Sci. U.S.A.* 85:2444–2448 (1988)). The predicted secondary structure, flexibility and hydrophilicity profiles are shown. The arrows centered at residue 475 demarcate the point of cleavage activation of the zymogen and denote a prominent turn region of highest flexibility and hydrophilicity in the entire protein.

6. The TGase3 Proteins Consist of Two Globular Domains Separated by a Flexible Hinge at the Site of Activation Secondary structural analyses (see Devereux, J., et al. *Nucleic Acid Res.* 12:387–394 (1984); Chou, P. Y. and Fasman, G. D., *Biochemistry* 13:222–245 (1974); Garnier, J., et al., *J. Mol. Biol.* 120:97–118 (1978); and Pearson, W. R. and Lipman, D. J., *Proc. Natl. Acad. Sci. U.S.A.* 85:2444–2448 (1988)) of the human and mouse TGase3 proteins reveal multiple interspersed regions of turns, sheet structures and α-helix, in both the 50 kDa amino-terminal and 27 kDa carboxy-terminal portions (FIG. 14). In general, these features suggest a folded compact configuration. However, the 12 residue insertion immediately following the cleavage site required for activation of the pro-enzyme describes a prominent protein turn that is surrounded by sequences that are the most hydrophilic and flexible in the entire protein (FIG. 14). Thus, this sequence describes a flexible hinge region and is likely to be located near the surface of the molecule. From these observations, we can infer that intact TGase3 molecules adopt an elongated shape consisting of two globular domains, a larger amino-terminal and a smaller carboxyl-terminal, that are separated by a flexible hinge corresponding to the activation site. This is flanked by highly polar residues, which are predicted to lie near the surface of the protein, that may be involved in recognition by and accessible to the activating protease(s). Following cleavage, the hinge region appears to collapse, promoting a more compact configuration that greatly enhances catalytic activity of the TGase3 molecule. No other members of the TGase family possess a flexible hinge region (FIG. 14) and all are predicted to adopt a compact globular form.

III. DNA Sequences of the Present Invention

A. Coding Sequences

As described earlier, the entire coding sequence of human TRHY (SEQ ID NO:93), human TGase3 (SEQ ID NO:109), and mouse TGase3 (SEQ ID NO:110) have been discovered. In most applications, it is anticipated that the portion of these sequences corresponding to the exons of the sequence, that is, the coding portions, will be most useful. A purified molecule of DNA corresponding to any of these coding sequences can be produced through various means known to the art, such as by using an automated DNA synthesizer.

As is known to those of skill in the art, a purified molecule of DNA containing the coding sequence of one of SEQ ID NO:93, SEQ ID NO:109, or SEQ ID NO:110 can also be produced by probing a cDNA library made from mRNA from human epidermal tissue (for human trichohyalin or TGase3) or mouse epidermal tissue (for mouse TGase3) with a probe specific to the desired sequence (such as one of those shown in Tables 2 and 5). Once a cDNA clone has been identified, it can be purified and at least partially sequenced in order to determine whether it contains the entire coding sequence.

It is advantageous that the DNA sequences used in the methods referred to herein be in purified form. The term "purified" does not require absolute purity; rather, it is intended as a relative definition. For example, individual clones isolated from a cDNA library, as described above, can be conventionally purified to homogeneity by running the DNA from such clones on an electrophoresis gel. Such cDNA clones can be said to be purified because they do not naturally occur as such, but rather are obtained via manipulation of a partially purified naturally occurring substance (messenger RNA). The conversion of mRNA into a cDNA library involves the creation of a synthetic substance (cDNA) and pure individual cDNA clones can be isolated from the synthetic library by clonal selection. Thus, creating a cDNA library from messenger RNA and subsequently isolating individual clones from that library results in an approximately $10^6$-fold purification of the native message. Purification of starting material or natural material (such as mRNA or genomic DNA) to at least one order of magnitude, preferably two or three orders, and more preferably four or five orders of magnitude is expressly contemplated.

1. DNA Probes

Since the coding sequences of TRHY, human TGase3, and mouse TGase3 are known, further probes for these sequences as well as primers for amplifying the sequences via PCR can be produced. The sequences falling within the scope of the present invention are not limited to the specific sequences described, such as those in Table 2, but include human allelic and species variations thereof and portions of SEQ ID NO:93, SEQ ID NO:109, and SEQ ID NO:110 of at least 15–18 consecutive nucleic acids. Such probes can be synthesized by various means known to the art, including the use of automated DNA synthesizers. These probes can be used, for example, to identify TRHY in the mRNA or genomic DNA of cells or cell cultures, or to amplify TRHY sequences using PCR.

B. DNA Vectors

The DNA sequences identified and purified as described above can further be cloned into any of a variety of vectors which are known to those of skill in the art, and are commercially available. The following vectors are provided by way of example:

Bacterial: pBs, phagescript, φX174, pBluescript SK, pBs KS, pNH8a, pNH16a, pNH18a, pNH46a (Stratagene); pTrc99A, pKK223-3, pKK233-3, pDR540, pRIT5 (Pharmacia); and Eukaryotic: pWLneo, pSV2cat, pOG44, pXT1, pSG (Stratagene); pSVK3, pBPV, pMSG, pSVL (Pharmacia).

Bacteriophage vectors, such as phage lambda can, of course, also be used.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, and trc. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

C. Cell Lines Containing Vectors

In order to express vectors containing the DNA sequences of the present invention, such vectors can be placed in appropriate cell lines. A wide variety of cell lines, including bacterial, insect, yeast, mammalian, and other cell lines, are available and known to those of skill in the art. The choice of which cell line to use with which vector is also within the knowledge of one of skill in the art. Introduction of a vector into a host cell line can be effected by calcium phosphate transfection, DEAE dextran mediated transfection, or electroporation (Davis, L., Dibner, M., Battey, I., Basic Methods in Molecular Biology, (1986)).

IV. RNA Sequences of the Present Invention

According to a further embodiment of the present invention, RNA can be produced from the DNA sequences of the present invention. The RNA molecules of the present invention are homologous or complementary to SEQ ID NO:93, SEQ ID NO:109, or SEQ ID NO:110 except that the thymine molecules are replaced by uracil molecules. Included in the invention are RNA molecules which comprise 20 or more consecutive nucleic acids of such RNA molecules homologous or complementary to SEQ ID NO:93, SEQ ID NO:109, or SEQ ID NO:110.

The RNA molecules of the present invention can be produced from the DNA molecules of the present invention by methods known to the art. For example, such molecules can be produced by inserting a DNA molecule having the sequence of SEQ ID NO:93 into a plasmid that has a bacteriophage promoter such as SP6, T7, or T3 upstream of the inserted DNA sequence. The appropriate RNA polymerase (SP6, T7, or T3) can then be used to generate RNA molecules having sequences which can be translated into TRHY (see *Short Protocols In Molecular Biology*, Ausbel, et al. eds., John Wiley & Sons (1989) and see also Sambrook, J., Fritsch, E. F. and Maniatis, T., *Molecular Cloning: A Laboratory Manual*, Cold Spring Harbor Press, Cold Spring Harbor, N.Y. (1989)).

Example 1: Production of Trichohyalin RNA

A DNA molecule having the sequence of SEQ ID NO:93 IS subcloned into a pGEM-3z plasmid vector. This plasmid is transfected into *E. coli* or other suitable host, and the host is cultured in order to increase the amount of plasmid material available to be transcribed into RNA (see Sambrook, J., Fritsch, E. F. and Maniatis, T., *Molecular Cloning: A Laboratory Manual*, Cold Spring Harbor Press, Cold Spring Harbor, N.Y. (1989)). Once sufficient material is available, the plasmid material can be isolated, purified, and transcribed in vitro with T7 RNA polymerase into an RNA molecule which has the sequence of SEQ ID NO:93 except that molecules of uracil are substituted for the thymine molecules. RNA molecules so produced can then be purified, such as by treating the in vitro reaction mixture with a DNase enzyme and then electrophoresing the mixture on an agarose gel.

V. Protein Molecules of the Present Invention

A. Expression of Protein Molecules

Another aspect of the present invention involves the production of protein molecules from the DNA and RNA molecules previously described. Such protein molecules will be homologous to at least a portion of SEQ ID NO:94, SEQ ID NO:111, and SEQ ID NO:112 and can be produced by methods known to those of skill in the art.

At the simplest level, the amino acid sequence encoded by the foregoing polynucleotide sequences can be synthesized using commercially available peptide synthesizers. This is particularly useful in producing small peptides and fragments of larger polypeptides. (Fragments are useful, for example, in generating antibodies against the native polypeptide.)

Alternatively, the DNA encoding the desired polypeptide can be inserted into a host organism and expressed. The organism can be a bacterium, yeast, cell line, or multicellular plant or animal. The literature is replete with examples of suitable host organisms and expression techniques. For example, naked polynucleotide (DNA or mRNA) can be injected directly into muscle tissue of mammals, where it is expressed. This methodology can be used to deliver the polypeptide to the animal, or to generate an immune response against a foreign polypeptide. Wolff, et al., Science 247:1465 (1990); Felgner, et al., Nature 349:351 (1991).

A DNA molecule of the present invention coding for all or part of any of SEQ ID NO:94, SEQ ID NO:111, or SEQ ID NO:112 can also be introduced into an expression vector in order to express one of these proteins. Techniques to transfer cloned sequences into expression vectors that direct protein translation in mammalian, yeast, insect or bacterial expression systems are well known in the art. Commercially available vectors and expression systems are available from a variety of suppliers including Stratagene (La Jolla, Calif.), Promega (Madison, Wis.), and Invitrogen (San Diego, Calif.). If desired, to enhance expression and facilitate proper protein folding, the codon context and codon pairing of the sequence may be optimized for the particular expression organism, as explained by Hatfield, et al., U.S. Pat. No. 5,082,767.

Example 2: Gene Expression from DNA Sequences of the Present Invention

The methionine initiation codon for a DNA molecule of the present invention and the poly A sequence of this molecule are first identified. If the molecule lacks a poly A sequence, this sequence can be added to the molecule by, for example, splicing out the Poly A sequence from pSG5 (Stratagene) using BglI and SalI restriction endonuclease enzymes and incorporating it into the mammalian expression vector pXT1 (Stratagene). pXT1 contains the LTRs and a portion of the gag gene from Moloney Murine Leukemia Virus. The position of the LTRs in the construct allow efficient stable transfection. The vector includes the Herpes Simplex Thymidine Kinase promoter and the selectable neomycin gene. cDNA is obtained by PCR from the bacterial vector using oligonucleotide primers complementary to the cDNA and containing restriction endonuclease sequences for Pst I incorporated into the 5'primer and BglII at the 5' end of the corresponding cDNA 3' primer, taking care to ensure that the cDNA molecule is positioned inframe with the poly A sequence.

The purified DNA molecule obtained from the resulting PCR reaction is digested with PstI, blunt ended with an exonuclease, digested with Bgl II, purified and ligated to pXT1, now containing a poly A sequence and digested BglII.

The ligated product is transfected into mouse NIH 3T3 cells using Lipofectin (Life Technologies, Inc., Grand Island, N.Y.) under conditions outlined in the product specification. Positive transfectants are selected after growing the transfected cells in 600 ug/ml G418 (Sigma, St. Louis, Mo.). The protein is preferrably released into the supernatant. However if the protein has membrane binding domains, the protein may additionally be retained within the cell or expression may be restricted to the cell surface.

Since it may be necessary to purify and locate the transfected product, synthetic 15-mer peptides synthesized from the predicted cDNA sequence are injected into mice to generate antibody to the polypeptide encoded by the cDNA. The antibody can then be used to identify and purify the protein of interest by known methods.

If antibody production is not possible, the cDNA sequence is additionally incorporated into eukaryotic expression vectors and expressed as a chimeric with, for example, β-globin. Antibody to β-globin is used to purify the chimeric. Corresponding protease cleavage sites engineered between the β-globin gene and the cDNA are then used to separate the two polypeptide fragments from one another after translation. One useful expression vector for generating β-globin chimerics is pSG5 (Stratagene). This vector encodes rabbit β-globin. Intron II of the rabbit β-globin gene facilitates splicing of the expressed transcript, and the polyadenylation signal incorporated into the construct increases the level of expression.

These techniques as described are well known to those skilled in the art of molecular biology. Standard methods are published in methods texts such as Davis et al. and many of the methods are available from the technical assistance representatives from Stratagene, Life Technologies, Inc., or Promega. Polypeptide may additionally be produced from either construct using in vitro translation systems such as In vitro Express™ Translation Kit (Stratagene).

B. Production of Antibodies

Another aspect of the present invention comprises producing antibodies to the proteins of the present invention. Such antibodies can be used, for example, in assays for the detection of the proteins of the present invention.

Example 3: Producing Antibodies to the Proteins of the Present Invention

Substantially pure protein or polypeptide is isolated from the transfected or transformed cells as described above in Example 2. The concentration of protein in the final preparation is adjusted, for example, by concentration on an Amicon filter device, to the level of a few micrograms/ml. Monoclonal or polyclonal antibody to the protein can then be prepared as follows:

(1) Monoclonal Antibody Production by Hybridoma Fusion

Monoclonal antibody to epitopes of any of the peptides identified and isolated as described can be prepared from murine hybridomas according to the classical method of Kohler, G. and Milstein, C., Nature 256:495 (1975) or derivative methods thereof. Briefly, a mouse is repetitively inoculated with a few micrograms of the selected protein over a period of a few weeks. The mouse is then sacrificed, and the antibody producing cells of the spleen isolated. The spleen cells are fused by means of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as Elisa, as originally described by Engvall, E., Meth. Enzymol. 70:419 (1980), and derivative methods thereof. Selected positive clones can be expanded and their monoclonal antibody product harvested for use. Detailed procedures for monoclonal antibody production are described in Davis, L. et al. Basic Methods in Molecular Biology Elsevier, N.Y. Section 21-2.

(2) Polyclonal Antibody Production by Immunization

Polyclonal antiserum containing antibodies to heterogenous epitopes of a single protein can be prepared by immunizing suitable animals with the expressed protein described above, which can be unmodified or modified to enhance immunogenicity. Effective polyclonal antibody production is affected by many factors related both to the antigen and the host species. For example, small molecules tend to be less immunogenic than other and may require the use of carriers and adjuvant. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis, J. et al. J. Clin. Endocrinol. Metab. 33:988–991 (1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony, O. et al., Chap. 19 in: Handbook of Experimental Immunology D. Wier (ed) Blackwell (1973). Plateau concentration of antibody is usually in the range of 0.1 to 0.2 mg/ml of serum (about 12 µM). Affinity of the antisera for the antigen is determined by preparing competitive binding curves, as described, for example, by Fisher, D., Chap. 42 in: Manual of Clinical Immunology, 2d Ed. (Rose and Friedman, eds.) Amer. Soc. For Microbiol., Washington, D.C. (1980).

Antibody preparations prepared according to either protocol are useful in quantitative immunoassays which determine concentrations of antigen-bearing substances in biological samples; they are also used semi-quantitatively or qualitatively to identify the presence of antigen in a biological sample.

VI. Uses of Trichohyalin and Transglutaminase-3

A. Gel Formation

Human TRHY has 332 glutamine and 104 lysine residues, which are potential targets for crosslinking by transglutaminases. Since the arginines and lysines lie on the periphery of the α-helix, they will be readily accessible by the peptidyl arginine desimidase and transglutaminase(s) enzymes. Thus, when TRHY is present in sufficient concentration in solution and an active TGase3 enzyme is added, the TRHY will become cross-linked and form a gel. Another embodiment of the present invention therefore involves the formation of gels with TRHY and TGase3 or other suitable enzymes.

The appropriate salt concentration, pH, and other solution variables for such a solution can be determined by one of skill in the art through routine experimentation. Such variables are determined by exposing solutions of TRHY having different salt concentrations, etc. to TGase3 (or another enzyme capable of cross-linking TRHY) and then determining the speed and extent to which TRHY becomes cross-linked. Physiological conditions, i.e. those found in mammalian epidermal tissue, are preferred for gel formation, however.

Concentrations of TRHY from approximately 0.01% to approximately 5% by weight of the solution can be used, depending on the rigidity desired in the resulting gel. Preferably, TRHY is present in concentrations of between 0.05% to 1.0%, and more preferably in a concentration of about 0.1%. Thus, 1 gram of TRHY in one liter of aqueous solution can be used to form a gel. In general, higher concentrations of TRHY will result in more rigid gels. This correlates to the finding that more TRHY is found in hard, terminally differentiated epidermal tissue than in softer, developing epidermal tissue. The desired physical characteristics of a gel for a particular use can, of course, be determined through routine skill in the art.

Concentrations of TGase3 which can be used to form gels with TRHY range from approximately 0.5% by weight of the TRHY to approximately 5% by weight. As is known to those of skill in the art, increasing the amount of enzyme used will, in general, both speed the cross-linking reaction and cause the reaction to proceed further (cause more cross-links to be made). Again, the proper amount of TGase3 to be used can be determined through the application of routine skill.

It is preferred that when the protein to be cross-linked is human TRHY, the enzyme used should be human TGase3. Mouse TGase3 can also be used, however, unless contraindicated by the use to which the gel is to be put. For example, a gel used in a cosmetic or food preparation might preferably be cross-linked by human TGase3 rather than mouse TGase3, since mouse TGase3 might cause an allergic reaction in some individuals exposed to the cosmetic or food preparation. Other cross-linking agents, such as human TGase1, can also be used in place of TGase3.

The gels formed according to this aspect of the invention can contain any number of other ingredients, as long as the presence or amount of such ingredients does not substantially interfere with gel formation. Ingredients used in the food and cosmetic industries can, for example, be added to form food and cosmetic compositions. It is a matter of routine experimentation to determine the range of possible ingredients which can be used in the gels produced according to the present invention. If one desires to know whether a particular ingredient can be included in such a gel, the ingredient can be added along with a gel-forming amount of TGase3 or other cross-linking agent to a solution of TRHY. If a gel is formed and the gel has the characteristics necessary to act as a food or cosmetic preparation, then the ingredient is one which can be used in the present invention to produce a food or cosmetic gel in combination with TRHY.

Example 4: Gel-Containing Food Preparation

Approximately 50 mg of human TGase3 is added to a 1 liter aqueous solution containing the following ingredients:

1 gram of TRHY, enough food coloring (such as a dye approved by the F.D.A. for use in human food products) to impart color to the resulting foodstuff, a preservative, and sufficient aspartame to sweeten the resulting foodstuff. Such a food preparation can be served as a dessert.

Example 5: Gel-Containing Breast Implant

A gel-containing breast implant is prepared by first lining a sterile mold with a sterile biocompatible plastic, one which will not cause adverse reactions when implanted into a human body. The mold is shaped and sized so as to produce an implant of suitable size and shape for implantation into a human patient. A sterile solution containing TRHY is poured into the plastic-lined mold, after which a sterile solution containing human TGase3 is poured into the mold. If necessary, another aqueous solution which does not carry either of these components is added to the mold to fill the mold. Sufficient TRHY should be used so that TRHY is present in the filled mold in an amount between 0.01% and 5% by weight of the solution, and preferably in an amount of about 0.1%. Human TGase3 should be present in an amount between about 1% and 5% by weight of the TRHY in solution. After a sufficient period of time to allow gel formation, a gel is formed in the mold surrounded by the plastic. The plastic is sealed, and any excess plastic not surrounding the gel is removed. A breast implant is thus formed which can then be implanted in a human patient.

B. Tissue Glue

In a further embodiment of the present invention, TRHY and TGase3 can be used to form structurally rigid gels for use in promoting the healing of wounds. In this embodiment, TRHY and an agent capable of cross-linking TRHY proteins such as TGase3 are mixed and applied to an open wound. The gel which forms then acts as a "scaffold" over which new tissue, such as skin, can grow. The gel can thus act not only to cover and protect damaged tissue but also to promote the healing and regrowth of tissue.

In treating humans, the use of human TRHY and human TGase3 is preferred so as to avoid the possibility of an allergic reaction. Other non-allergenic cross-linking enzymes or agents, such as a truncated mouse TGase3 protein which does not present mouse allergens but still retains cross-linking activity, for example, can also be used.

The amount of TRHY and enzyme used on a particular wound will depend on the desired characteristics of the gel to be formed. Preferably, TRHY is present in an amount between 0.01% and 5.0% by weight of the solution, and more preferably in an amount of about 0.1%. When treating wounds to soft, internal tissues, a less rigid gel may be called for, meaning that a solution having a lower concentration of TRHY should be used. Conversely, when the wound being treated is a skin tear that is open to the environment, a tougher, relatively more rigid composition may be called for, and a higher concentration of TRHY can be used. In this embodiment, the gel can supplement or replace a bandage to cover the exposed tissue. In general, the properties of the wound-healing composition according to the present invention can be varied as described above for controlling the rigidity of TRHY gels, that is, by varying the amount of TRHY and the amount of enzyme used to form the composition.

Example 6: Use of TRHY to Form a Tissue Glue

A sterile solution of approximately 1% by weight TRHY is prepared. Just prior to the application of the solution to a tear in the skin, a concentrated, sterile solution containing human TGase3 is mixed with the TRHY solution such that the resulting solution contains approximately 3% human TGase3 by weight of the TRHY in solution. Before the gel completely solidifies, the mixture of TGase3 and TRHY is applied to the skin wound so as to fill and cover the wound. After the gel solidifies, the wound is protected from the environment by the gel. In addition, the gel helps to bind the torn edges of the wound, thus further promoting healing.

Although the present invention has been described in terms of certain preferred embodiments, such embodiments are provided herein as examples and are not meant to limit the scope of the present invention. The disclosures of the references referred to herein are, in addition, hereby incorporated by reference.

TABLE 1

Abundances of selected mRNAs in mouse and human epidermis and cultured cells (fmol/10 μg of total cellular RNA)

| | Keratin 10 | Profilaggrin | Loricrin | Trichohyalin |
|---|---|---|---|---|
| Human foreskin epidermis | 63.5 ± 5.5 | 42.3 ± 3.7 | 39.4 ± 3.8 | 0.28 ± 0.03 |
| Human, cultured, low $Ca^{2+}$ | 0.25 ± 0.33 | 0.17 ± 0.22 | 0.07 ± 0.11 | 0.01 ± 0.02 |
| Human, cultured, high $Ca^{2+}$ | 1.75 ± 0.24 | 0.73 ± 0.11 | 1.05 ± 0.17 | 0.05 ± 0.04 |
| Mouse epidermis | 43.6 ± 3.4 | 29.8 ± 4.1 | 27.4 ± 2.5 | (0.33 ± 0.46) |
| Mouse, cultured, low $Ca^{2+}$ | 0.23 ± 0.33 | 0.11 ± 0.13 | 0.09 ± 0.10 | (0.00 ± 0.02) |
| Mouse, cultured, high $Ca^{2+}$ | 2.35 ± 0.22 | 0.28 ± 0.19 | 0.16 ± 0.09 | (0.05 ± 0.11) |
| Mouse hair follicles | 0.47 | 0.58 | 0.97 | (8.85) |

The data are the average (± s.d.) of four different experiments, except for mouse hair follicles (one batch, gift of Dr. Ulrike Lichti). These values were calculated from the Northern slot blots (FIG. 1b) based on calibrations of 10, 1, 0.1 and 0.01 fmol of known cloned probes. Because we do not have a specific cloned probe of mouse TRH, the numbers in parenthesis adduced here are based on the hybridization signal obtained with the human TRHY probe.

TABLE 2

Synthetic oligonucleotides used as primers for anchored PCR primer extension of human TRHY mRNA

| Primer | Sequence | SEQ ID NO. | Location (numbered as in FIG. 3) |
|---|---|---|---|
| 1– | 5'-AGGGCGGTATTGAGATCTCTGCTCT | 1 | 8067–8044 |
| 1+ | 5'-GACAGAAAATTCCGCGAGGAGGAGG | 2 | 7546–7569 |
| 2– | 5'-CCTCCTCCTCGCGGAATTTTCTGTC | 3 | 7569–7546 |
| 3– | 5'-CCTGACGCCGCTGTTGGCCGCGCTC | 4 | 6895–6871 |
| 4– | 5'-TCAGCAACTGCTTTTCCTCTTGGGA | 5 | 6211–6187 |
| 5– | 5'-GTTGCCACCTCCATTTTTGGTC | 6 | 5055–5035 |

TABLE 2-continued

Synthetic oligonucleotides used as primers for anchored PCR primer extension of human TRHY mRNA

| Primer | Sequence | SEQ ID NO. | Location (numbered as in FIG. 3) |
|---|---|---|---|
| 6– | 5'-CTTTGCCGTGCGTCGGCCTC | 7 | 4580–4560 |
| 7– | 5'-GCTCGCGTCTTAGTTGTTGCTCGCT | 8 | 4054–4029 |
| 8– | 5'-GTCGATCTTGTAACAGGCTTTCCTT | 9 | 2742–2719 |
| 9– | 5'-CTACCGTCTTAGGGTCATGTGGTC | 10 | 2536–2513 |

TABLE 3

Fast Fourier Transforms of segments of the human TRH sequence

| Domain | Segment | Charged/apolar[a] Ratio | 14 value[b] | Residue | Period | Intensity[c] | Comments |
|---|---|---|---|---|---|---|---|
| 1 | 1–94 | 0.6 | | | | | two well-defined EF-hand calcium binding domains |
| 2 | 95–312 | 4.4 | 1.54 | | | | no organized repeating element; largely α-helical; elongated rod, ca 32 nm |
| 3 | 313–389 | 10.4 | 1.91 | | | | repeat of 13 residues; RREQEEERREQQL (SEQ ID NO: 11) |
| | 390–443 | 3.0 | 1.02 | | | | repeat of 6 residues: RREQQL (SEQ ID NO: 12) both form highly stabilized α-helix; elongated rod, ca 19 nm |
| | | | | R | 6.40 (12.8/2) | 24.15 | |
| | | | | Q | 6.38 (12.8/2) | 18.11 | |
| | | | | E | 12.64 (12.8/1) | 7.88 | |
| 4 | 444–702 | 6.25 | 2.17 | | | | irregular consensus repeat of 28 residues LKREQEERREQRLKREEEEREQERREQR (SEQ ID NO: 13) or [(REQRLKRE$^E$/$_Q$EER)$_2$EQER] (SEQ ID NO: 14) highly stabilized α-helix; elongated flexible rod, a 38 nm |
| | | | | R + K | 6.07 | 18.76 | |
| | | | | R | 6.08 | 14.60 | |
| | | | | Q | 6.08 | 8.19 | |
| | | | | Q | 5.90 | 9.36 | |
| | | | | E | 10.19 | 9.92 | |
| 5 | 703–922 | 2.62 | 1.05 | | | | potential regularity around W residues QEQARERIKSRIPKWQWQLESEADAR (SEQ ID NO: 15) contains α-helix but also several turns; potential for β-turns or even β-sheet; folded or globular |
| 6 | 923–1163 | 4.85 | 2.03 | | | | highly regular 30-residue repeat QEEEQLLREEREKRRRQERERQYR$^E$/$_K$EEELQ (SEQ ID NO: 16) highly stabilized α-helix; elongated rod ca 36 nm |
| | | | | L | 29.90 (30/1) | 8.69 | |
| | | | | | 10.06 (30/3) | 14.47 | |
| | | | | | 7.50 (30/4) | 18.34 | |
| | | | | | 6.01 (30/5) | 11.11 | |
| | | | | | 4.29 (30/7) | 9.71 | |
| | | | | R + K | 29.90 (30/1) | 22.26 | |
| | | | | R | 29.90 (30/1) | 22.05 | |
| | | | | | 4.29 (30/7) | 9.84 | |
| | | | | E | 7.52 (30/4) | 43.61 | |
| | | | | | 6.00 (30/5) | 10.60 | |
| | | | | Q | 15.06 (30/2) | 11.12 | |
| | | | | | 5.99 (30/6) | 12.89 | |
| | | | | | 4.28 (30/7) | 23.12 | |
| 7 | 1164–1249 | 3.15 | 0.73 | | | | no apparent regularity; contains α-helix but also several turns; folded or globular |

TABLE 3-continued

Fast Fourier Transforms of segments of the human TRH sequence

| Domain | Segment | Charged/apolar[a] Ratio | 14 value[b] | Residue | Period | Intensity[c] | Comments |
|---|---|---|---|---|---|---|---|
| 8 | 1250–1849 | 3.72 | 1.86 | | | | well defined but irregular repeat with consensus of 26 residues, but several are shorter RQERDRKFREEEQQLRRQEREEQQLR (SEQ ID NO: 17) or [(EEQQLRRQER)$_2$DRKFRE (SEQ ID NO: 18) most common element of: RQERDRKFREEEQ (SEQ ID NO: 19) highly stablilized α-helix; elongated rod ca 90 nm |
| | | | | L | 7.85 | 13.28 | |
| | | | | | 4.91 | 9.08 | |
| | | | | R + K | 7.89 | 9.25 | |
| | | | | E + D | 7.88 | 9.25 | |
| | | | | | 7.73 | 39.90 | |
| | | | | E | 7.88 | 39.98 | |
| | | | | | 7.73 | 22.68 | |
| | | | | Q | 4.00 | 10.19 | |
| 9 | 1850–1897 | | | | | | no repeats; likely to be folded or globular due to frequent turns |

[a]Charged/apolar = DEKHR/LIVMFYA
[b]Number of possible intrachain ionic interactions arising from residues four apart (48). The result (14) is presented here on a per seven residue basis for ease of comparison with the interchain ionic interactions that stabilize coiled-coil ropes in α-fibrous proteins (39, 40). The higher the 14 values, the more stable is an α-helix; typical values are: four- or more-stranded α-helical bundled, charged/apolar <0.5, 14 ca 0; three-stranded α-helical coiled-coil, charged/apolar ca 0.8 14=0.5; two-stranded α-helical coiled-coil, charged/apolar ca 1.0, 14=0.8; overall charged/apolar ratio of TRHY is 4.1, 14=1.7. This supports the idea that TRHY forms a single-stranded α-helical rod stabilized by ionic salt bridges between oppositely-charged residues which lie four residues apart on adjacent turns of the α-helix.
[c]The major scaled intensities >9 corresponding to periods >4 residues are given. The probability of intensity (/) occurring by change is exp (–/).

TABLE 4

Amino Acid Sequences of Tryptic Peptides of Guinea Pig TGase3

| | SEQ ID NO | PEPTIDE ORDER | |
|---|---|---|---|
| 50 kDa fragment: | 20 | 1 | CLGVRSR[a] |
| | 21 | 2 | VSQGVFQCGPASVIAV |
| | 22 | 3 | FGQCWVFAGTLNTVL[a] |
| | 23 | 4 | E$^{G/_N}$DVDLNFVMPFIY |
| | 24 | 5 | GSDSVWNFHVWNVAWFVR |
| | 25 | 6 | LGTFVLLFNPWLQADDVFMS |
| 27 kDa fragment: | 26 | 7 | AQRSPGREQAPSISGRFKVNGVLAVGQE[b] |
| | 27 | 8 | TTAICK |
| | 28 | 9 | ITYAQYEK |
| | 29 | 10 | FEILPTR |
| | 30 | 11 | D/$_H$LVLDFEGSCLLR |
| | 31 | 12 | DVILDNPTLTEVLD |
| | 32 | 13 | KP$^{V/_G}$NVQCLFSNPLDG |

[a]By comparisons with other TGase sequences, these two peptides constitute the active site (order: 3–1); sequence alignments show that they are unique to and thus diagnostic for the TGase3 system.
[b]This is the amino-terminus of the 27 kDa fragment (21) and thus represents the cleavage activation site of guinea pig TGase3.

TABLE 5

Sequences of Oligonucleotide Primers Used For Anchored-PCR Experiments

| Primer | | SEQ ID NO: | How Used |
|---|---|---|---|
| Mouse primers: | | | |
| P1+ | 5'-TGGGTITT$^T/_C$GCIGGNACN$^T/_C$TIAA$^T/_C$AC | 33 | PCR P1+, P3– |
| P3– | 5'-GCIGGICC$^{G/_A}$CA$^T/_C$TG$^{A/_G}$AANACICC$^T/_C$TG | 34 | |
| 1a+ | 5'-ACTGACCTAGGCCCCACATACA | 35 | PCR 1a+, P10–; then 1b+, P10– |
| 1b+ | 5'-AGAAGCCAAGGCGTATTCCAA | 36 | |
| P10– | 5'-ACNCC$^{A/_G}$TT$^{A/_G}$TA$^T/_C$TT$^{A/_G}$AAIC$^T/_G$CC | 37 | |
| P5+ | 5'-CA$^{A/_G}$GCNGA$^T/_C$GA$^T/_C$GTITT$^T/_C$ATG | 38 | PCR P5+, 2a–; then P5+, 2b– |
| 2a– | 5'-TGTATGTGGGGCCTAGGTCAGT | 39 | |
| 2b– | 5'-CATGGCATCGTAGTACACATCCAC | 40 | |
| 3a– | 5'-GTCACGACGGAAATTCAGACTCCT | 41 | primer extension with 3a–, dG tail |
| 3b– | 5'-TTGTCTTTCGGCGTGGTTACT | 42 | PCR oligo-dC, 3b– |

TABLE 5-continued

Sequences of Oligonucleotide Primers Used For Anchored-PCR Experiments

| Primer | | SEQ ID NO: | How Used |
|---|---|---|---|
| 4a+ | 5'-GGCTTTGGACAAACTCAAACC | 43 | primer extension with random hexamer |
| 4b+ | 5'-GACAAGGAGCCCAGCATTTCT | 44 | dG tail. PCR 4a+, oligo-dC; then 4b+, oligo-dC |
| 5a+ | 5'-GAGAGATACCTGAAGACAGAGAC | 45 | primer extension with random hexamer |
| 5b+ | 5'-AACATGATCCGGATCTCAGCC | 46 | dG tail. PCR 5a+, oligo-dC; then 5b+, oligo-dC |
| Human primers: | | | |
| 6a+ | 5'-TCCTCTCTGAAACTTGGCTTT | 47 | PCR 6a+, 7a–; then 6b+, 7b– |
| 6b+ | 5'-CAAGCGGATGATGTCTTTATG | 48 | |
| 7a– | 5'-GAAAATCATCTGCACGTTCAC | 49 | |
| 7b– | 5'-GTCCAGGGGGTTGGAGGAAAAT | 50 | |
| 8a– | 5'-ACGGCGGAAATTCAGACTCCT | 51 | primer extension with 8a–, dG tail. |
| 8b– | 5'-CATGCCAATTCGGTTTGTGCT | 52 | PCR oligo-dC, 8b– |
| 9a+ | 5'-GAACATCCCATAAAGATCTCG | 53 | primer extension with oligo-dT |
| 9b+ | 5'-GTACGCTCAGTATGAGAGGTA | 54 | PCR 9a+, oligo-dA; then 9b+, oligo-dA |
| TGase2+ | 5'-CCAGCCTGCTGAGAGCCC | 55 | PCR primers to amplify 0.7 kbp |
| TGase2– | 5'-CAGTGGACTCAGCGTCAG | 56 | 3'-non-coding region, using λgt11 cDNA library (45) DNA as template |

"P" oligonucleotides were derived from numbered peptide sequences (see Table 4).
"+" means plus (left) primer; "–" means minus (right) primer. The "a" primers were used in the first PCR reaction. The "b" primers were nested inside the "a" primers and used for the second round of PCR on a diluted sample of the first reaction. I = inosine; N = all 4 nt. Note, the primers 6a+, 6b+, 7b–, 7a– are from corresponding mouse TGase sequences.

TABLE 6

Abundances of Mouse and Human TGase mRNAs (fmol/10 µg of Total Cellular RNA)

| | TGase1 | TGase2 | TGase3 |
|---|---|---|---|
| Human foreskin epidermis | 0.45 ± 0.06 | 0.071 ± 0.023 | 0.078 ± 0.022 |
| Human, cultured, low $Ca^{2+}$ | 0.91 ± 0.08 | 0.135 ± 0.015 | <0.002 |
| Human, cultured, high $Ca^{2+}$ | 1.05 ± 0.11 | 0.112 ± 0.021 | 0.008 ± 0.002 |
| Mouse epidermis | 0.57 ± 0.01 | 0.053 ± 0.017 | 0.081 ± 0.019 |
| Mouse, cultured, low $Ca^{2+}$ | 1.37 ± 0.16 | 0.121 ± 0.028 | <0.002 |
| Mouse hair follicles | 0.27 | 0.029 | 0.087 |

The data are the average (±s.d.) of four difference experiments, except for mouse hair follicles (one batch, a gift of Dr. Ulrike Lichti). These values were calculated from the Northern slot blots (FIG. 12b), based on calibrations of 10, 1, 0.1, 0.01 fmol of known cloned probes.

TABLE 7

Comparisons of Amino Acid Sequences of Human, Mouse and Guinea Pig TGase3 Tryptic Peptides

| | | SEQ ID NO: |
|---|---|---|
| 50 kDa fragment: | | |
| human | YGQCWVFAGTLNTALRSLGIPSR | 57 |
| mouse | F............V..C..VR.. | 58 |
| guinea pig | F............V..C..VR.. | 59 |
| human | AHDTDRNLSVDVYYD | 60 |
| mouse | ............... | 61 |
| guinea pig | EG.V.L.F-.MPFIY | 62 |
| human | RSQGVFQCGPASVIGV | 63 |
| mouse | ............NAI | 64 |
| guinea pig | V............A. | 65 |
| human | GSDSVWNFHVWNEGWFVR | 66 |
| mouse | ................... | 67 |
| guinea pig | ............VA.... | 68 |
| human | LGTFILLFNPWLNVDSVFMG | 69 |
| mouse | ....V.......QA.D...S | 70 |
| guinea pig | ....V.......QA.D...S | 71 |
| 27 kDa fragment: | | |
| human | SMGLETEEQEPSIIGKLKVAGMLAVGKE | 72 |
| mouse | .RNP.G.DK....S..F..T.I...... | 73 |
| guinea pig | AQRSPGR..A...S.RF..N.V....Q.* | 74 |
| human | ISYAQYER | 75 |
| mouse | .A.S.... | 76 |
| guinea pig | .T.....K | 77 |

TABLE 7-continued

Comparisons of Amino Acid Sequences of Human, Mouse and Guinea Pig TGase3 Tryptic Peptides

|  |  | SEQ ID NO: |
|---|---|---|
| human | ITAVCK | 78 |
| mouse | .S.... | 79 |
| guinea pig | T..I.. | 80 |
| human | FDILPSR | 81 |
| mouse | .E.F.T. | 82 |
| guinea pig | .E...T. | 83 |
| human | KPVNVQMLFSNPLDE | 84 |
| mouse | .......I......Q | 85 |
| guinea pig | ......C.......G | 86 |
| human | DIILDNPTLTLEVLN | 87 |
| mouse | .V.....A......E | 88 |
| guinea pig | .V............D | 89 |
| human | DCVLMVEGSGLLL | 90 |
| mouse | N...L.....CSV | 91 |
| guinea pig | .L..DF...C..R | 92 |

*This peptide is the amino terminus of the 27 kDa fragment and thus represents the cleavage activation site of TGase3.

TABLE 8

Homology Scores Between Different TGase-like Proteins

A. Inter-species comparisons

| human TGase3: mouse TGase3 | 75% identity, 84% homology |
|---|---|
| human TGase3: guinea pig TGase3[a] | 50% identity, 80% homology, overall |
|  | 60% identity, 84% homology, 50 kDa portion |
|  | 45% identity, 78% homology, 27 kDa portion |
| human TGase1: mouse TGase1 | 93% identity, 97% homology |
| human TGase2: mouse TGase2 | 90% identity, 95% homology |

B. Inter-chain comparisons[b]

| human TGase3: human TGase1 | 53% identity, 68% homology |
|---|---|
| human TGase3: human TGase2 | 48% identity, 64% homology |
| human TGase3: human band 4.2 | 46% identity, 62% homology |
| human TGase3: human XIIIa | 38% identity, 56% homology |
| human TGase1: human TGase2 | 42% identity, 57% homology |
| human TGase1: human XIIIa | 47% identity, 61% homology |
| human TGase1: human band 4.2 | 28% identity, 47% homology |
| human XIIIa: human band 4.2 | 43% identity, 64% homology |

[a]includes only information from available 180 sequenced amino acids of guinea pig TGase3 tryptic peptides (Table 4).
[b]includes only regions bounded by conserved intron junctions.

---

What we claim is:

1. A purified molecule of DNA comprising the sequence of SEQ ID NO:109.

2. A purified molecule of DNA according to claim 1, wherein said molecule is present in a recombinant DNA vector.

3. The vector of claim 2, wherein said vector comprises a plasmid.

4. The vector of claim 2, wherein said vector is present in a cell line and wherein said cell line does not naturally contain said molecule of DNA.

5. A purified molecule of DNA comprising the sequence of SEQ ID NO:110.

6. A purified molecule of DNA according to claim 5, wherein said molecule is present in a recombinant DNA Vector.

7. The vector of claim 6, wherein said vector comprises a plasmid.

8. The vector of claim 6, wherein said vector is present in a cell line and wherein said cell line does not naturally contain said molecule of DNA.

9. A purified molecule of RNA comprising the coding sequence of SEQ ID NO:109, wherein the thymine molecules of SEQ ID NO:109 are replaced by uracil molecules.

10. A purified molecule of RNA comprising the sequence of SEQ ID NO:110, wherein the thymine molecules of SEQ ID NO:110 are replaced by uracil molecules.

11. A purified molecule of DNA which codes for human transglutaminase-3, said transglutaminase-3 having an amino acid sequence given by SEQ ID NO:112.

12. A purified molecule of DNA which codes for mouse transglutaminase-3, said transglutaminase-3 having an amino acid sequence given by SEQ ID NO:111.

* * * * *

SEQUENCE LISTING ( 1 ) GENERAL INFORMATION:

( i i i ) NUMBER OF SEQUENCES: 117

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:1:

AGGGCGGTAT TGAGATCTCT GCTCT    25

( 2 ) INFORMATION FOR SEQ ID NO:2:

( i ) SEQUENCE CHARACTERISTICS:
        ( A ) LENGTH: 25 base pairs ( B ) TYPE: nucleic acid
            ( C ) STRANDEDNESS: single
            ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:2:

GACAGAAAAT TCCGCGAGGA GGAGG 25

( 2 ) INFORMATION FOR SEQ ID NO:3:

( i ) SEQUENCE CHARACTERISTICS:
            ( A ) LENGTH: 25 base pairs
            ( B ) TYPE: nucleic acid
            ( C ) STRANDEDNESS: single
            ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:3:

CCTCCTCCTC GCGGAATTTT CTGTC 25

( 2 ) INFORMATION FOR SEQ ID NO:4:

( i ) SEQUENCE CHARACTERISTICS:
            ( A ) LENGTH: 25 base pairs
            ( B ) TYPE: nucleic acid
            ( C ) STRANDEDNESS: single
            ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:4:

CCTGACGCCG CTGTTGGCCG CGCTC 25

( 2 ) INFORMATION FOR SEQ ID NO:5:

( i ) SEQUENCE CHARACTERISTICS:
            ( A ) LENGTH: 25 base pairs
            ( B ) TYPE: nucleic acid
            ( C ) STRANDEDNESS: single
            ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:5:

TCAGCAACTG CTTTTCCTCT TGGGA 25

( 2 ) INFORMATION FOR SEQ ID NO:6:

( i ) SEQUENCE CHARACTERISTICS:
            ( A ) LENGTH: 22 base pairs
            ( B ) TYPE: nucleic acid
            ( C ) STRANDEDNESS: single
            ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:6:

GTTGCCACCT CCATTTTTGG TC 22

( 2 ) INFORMATION FOR SEQ ID NO:7:

( i ) SEQUENCE CHARACTERISTICS:
                        ( A ) LENGTH: 20 base pairs
                        ( B ) TYPE: nucleic acid
                        ( C ) STRANDEDNESS: single
                        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:7:

CTTTGCCGTG CGTCGGCCTC 20

( 2 ) INFORMATION FOR SEQ ID NO:8:

( i ) SEQUENCE CHARACTERISTICS:
                        ( A ) LENGTH: 25 base pairs
                        ( B ) TYPE: nucleic acid
                        ( C ) STRANDEDNESS: single
                        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:8:

GCTCGCGTCT TAGTTGTTGC TCGCT 25

( 2 ) INFORMATION FOR SEQ ID NO:9:

( i ) SEQUENCE CHARACTERISTICS:
                        ( A ) LENGTH: 25 base pairs
                        ( B ) TYPE: nucleic acid
                        ( C ) STRANDEDNESS: single
                        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:9:

GTCGATCTTG TAACAGGCTT TCCTT 25

( 2 ) INFORMATION FOR SEQ ID NO:10:

( i ) SEQUENCE CHARACTERISTICS:
                        ( A ) LENGTH: 24 base pairs
                        ( B ) TYPE: nucleic acid
                        ( C ) STRANDEDNESS: single
                        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:10:

CTACCGTCTT AGGGTCATGT GGTC 24

( 2 ) INFORMATION FOR SEQ ID NO:11:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:11:

Arg Arg Glu Gln Glu Glu Glu Arg Arg Glu Gln Gln Leu
1               5                   10

( 2 ) INFORMATION FOR SEQ ID NO:12:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:12:

Arg Arg Glu Gln Gln Leu
1               5

( 2 ) INFORMATION FOR SEQ ID NO:13:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:13:

Leu Lys Arg Glu Gln Glu Glu Arg Arg Glu Gln Arg Leu Lys Arg Glu
1               5                   10                  15
Glu Glu Glu Arg Glu Gln Glu Arg Arg Glu Gln Arg
                20                  25

( 2 ) INFORMATION FOR SEQ ID NO:14:

( i ) SEQUENCE CHARACTERISTICS:
        ( A ) LENGTH: 28 amino acids
        ( B ) TYPE: amino acid
        ( C ) STRANDEDNESS: single ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:14:

```
Arg Glu Gln Arg Leu Lys Arg Glu Xaa Glu Glu Arg Arg Glu Gln Arg
 1               5                  10                      15
Leu Lys Arg Glu Xaa Glu Glu Arg Glu Gln Glu Arg
                20                  25
```

( 2 ) INFORMATION FOR SEQ ID NO:15:

( i ) SEQUENCE CHARACTERISTICS:
      ( A ) LENGTH: 26 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:15:

```
Gln Glu Gln Ala Arg Glu Arg Ile Lys Ser Arg Ile Pro Lys Trp Gln
 1               5                  10                      15
Trp Gln Leu Glu Ser Glu Ala Asp Ala Arg
                20                  25
```

( 2 ) INFORMATION FOR SEQ ID NO:16:

( i ) SEQUENCE CHARACTERISTICS:
      ( A ) LENGTH: 30 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:16:

```
Gln Glu Glu Glu Gln Leu Leu Arg Glu Glu Arg Glu Lys Arg Arg Arg
 1               5                  10                      15
Gln Glu Arg Glu Arg Gln Tyr Arg Xaa Glu Glu Glu Leu Gln
                20                  25                  30
```

( 2 ) INFORMATION FOR SEQ ID NO:17:

( i ) SEQUENCE CHARACTERISTICS:
      ( A ) LENGTH: 26 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO (iv) ANTI-SENSE: NO (v) FRAGMENT TYPE: internal (xi) SEQUENCE DESCRIPTION: SEQ ID NO:17:

Arg Gln Glu Arg Asp Arg Lys Phe Arg Glu Glu Gln Gln Leu Arg
1               5                   10                  15

Arg Gln Glu Arg Glu Glu Gln Gln Leu Arg
            20              25

(2) INFORMATION FOR SEQ ID NO:18:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:18:

Glu Glu Gln Gln Leu Arg Arg Gln Glu Arg Glu Glu Gln Gln Leu Arg
1               5                   10                  15

Arg Gln Glu Arg Asp Arg Lys Phe Arg Glu
            20              25

(2) INFORMATION FOR SEQ ID NO:19:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:19:

Arg Gln Glu Arg Asp Arg Lys Phe Arg Glu Glu Glu Gln
1               5                   10

(2) INFORMATION FOR SEQ ID NO:20:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:20:

Cys Leu Gly Val Arg Ser Arg 5,616,500

51

-continued 1                               5

( 2 ) INFORMATION FOR SEQ ID NO:21:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:21:

Val  Ser  Gln  Gly  Val  Phe  Gln  Cys  Gly  Pro  Ala  Ser  Val  Ile  Ala  Val
1                   5                        10                       15

( 2 ) INFORMATION FOR SEQ ID NO:22:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:22:

Phe  Gly  Gln  Cys  Trp  Val  Phe  Ala  Gly  Thr  Leu  Asn  Thr  Val  Leu
1                   5                        10                       15

( 2 ) INFORMATION FOR SEQ ID NO:23:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:23:

Glu  Xaa  Asp  Val  Asp  Leu  Asn  Phe  Val  Met  Pro  Phe  Ile  Tyr
1                   5                        10

( 2 ) INFORMATION FOR SEQ ID NO:24:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO (i v) ANTI-SENSE: NO (v) FRAGMENT TYPE: internal (x i) SEQUENCE DESCRIPTION: SEQ ID NO:24:

```
Gly Ser Asp Ser Val Trp Asn Phe His Val Trp Asn Val Ala Trp Phe
1               5                   10                  15
Val Arg
```

(2) INFORMATION FOR SEQ ID NO:25:

(i) SEQUENCE CHARACTERISTICS:
        (A) LENGTH: 20 amino acids
        (B) TYPE: amino acid
        (C) STRANDEDNESS: single
        (D) TOPOLOGY: linear (i i) MOLECULE TYPE: cDNA (i i i) HYPOTHETICAL: NO (i v) ANTI-SENSE: NO (v) FRAGMENT TYPE: internal (x i) SEQUENCE DESCRIPTION: SEQ ID NO:25:

```
Leu Gly Thr Phe Val Leu Leu Phe Asn Pro Trp Leu Gln Ala Asp Asp
1               5                   10                  15
Val Phe Met Ser
            20
```

(2) INFORMATION FOR SEQ ID NO:26:

(i) SEQUENCE CHARACTERISTICS:
        (A) LENGTH: 28 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:26:

```
Ala Gln Arg Ser Pro Gly Arg Glu Gln Ala Pro Ser Ile Ser Gly Arg
1               5                   10                  15
Phe Lys Val Asn Gly Val Leu Ala Val Gly Gln Glu
            20                  25
```

(2) INFORMATION FOR SEQ ID NO:27:

(i) SEQUENCE CHARACTERISTICS:
        (A) LENGTH: 6 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:27:

```
    Thr  Thr  Ala  Ile  Cys  Lys
    1                 5
```

(2) INFORMATION FOR SEQ ID NO:28:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:28:

```
    Ile  Thr  Tyr  Ala  Gln  Tyr  Glu  Lys
    1                 5
```

(2) INFORMATION FOR SEQ ID NO:29:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:29:

```
    Phe  Glu  Ile  Leu  Pro  Thr  Arg
    1                 5
```

(2) INFORMATION FOR SEQ ID NO:30:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:30:

```
    Xaa  Leu  Val  Leu  Asp  Phe  Glu  Gly  Ser  Cys  Leu  Leu  Arg
    1                 5                           10
```

(2) INFORMATION FOR SEQ ID NO:31:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:31:

```
Asp  Val  Ile  Leu  Asp  Asn  Pro  Thr  Leu  Thr  Glu  Val  Leu  Asp
1              5                        10
```

(2) INFORMATION FOR SEQ ID NO:32:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE: internal (xi) SEQUENCE DESCRIPTION: SEQ ID NO:32:

```
Lys  Pro  Xaa  Asn  Val  Gln  Cys  Leu  Phe  Ser  Asn  Pro  Leu  Asp  Gly
1              5                        10                       15
```

(2) INFORMATION FOR SEQ ID NO:33:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:33:

TGGGTNTT YG CNGGNACN YT- NAA Y AC         26

(2) INFORMATION FOR SEQ ID NO:34:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:34:

GCNGGNCCRC A Y TGRAANAC NCC Y TG         26

(2) INFORMATION FOR SEQ ID NO:35:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:35:

ACTGACCTAG GCCCCACATA CA 22

(2) INFORMATION FOR SEQ ID NO:36:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:36:

AGAAGCCAAG GCGTATTCCA A 21

(2) INFORMATION FOR SEQ ID NO:37:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:37:

ACNCCRTTRT AYTTRAANCK CC 22

(2) INFORMATION FOR SEQ ID NO:38:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:38:

CARGCNGAYG AYGTNTTYAT G 21

(2) INFORMATION FOR SEQ ID NO:39:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (iv) ANTI-SENSE: NO (xi) SEQUENCE DESCRIPTION: SEQ ID NO:39:

TGTATGTGGG GCCTAGGTCA GT     22

(2) INFORMATION FOR SEQ ID NO:40:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:40:

CATGGCATCG TAGTACACAT CCAC     24

(2) INFORMATION FOR SEQ ID NO:41:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:41:

GTCACGACGG AAATTCAGAC TCCT     24

(2) INFORMATION FOR SEQ ID NO:42:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:42:

TTGTCTTTCG GCGTGGTTAC T     21

(2) INFORMATION FOR SEQ ID NO:43:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:43:

GGCTTTGGAC AAACTCAAAC C　　　　　　　　　　　　　　　　　　　　　　　　　　　　21

( 2 ) INFORMATION FOR SEQ ID NO:44:

( i ) SEQUENCE CHARACTERISTICS:
　　　　　　　　( A ) LENGTH: 21 base pairs
　　　　　　　　( B ) TYPE: nucleic acid
　　　　　　　　( C ) STRANDEDNESS: single
　　　　　　　　( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:44:

GACAAGGAGC CCAGCATTTC T　　　　　　　　　　　　　　　　　　　　　　　　　　　　21

( 2 ) INFORMATION FOR SEQ ID NO:45:

( i ) SEQUENCE CHARACTERISTICS:
　　　　　　　　( A ) LENGTH: 23 base pairs
　　　　　　　　( B ) TYPE: nucleic acid
　　　　　　　　( C ) STRANDEDNESS: single
　　　　　　　　( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:45:

GAGAGATACC TGAAGACAGA GAC　　　　　　　　　　　　　　　　　　　　　　　　　　　23

( 2 ) INFORMATION FOR SEQ ID NO:46:

( i ) SEQUENCE CHARACTERISTICS:
　　　　　　　　( A ) LENGTH: 21 base pairs
　　　　　　　　( B ) TYPE: nucleic acid
　　　　　　　　( C ) STRANDEDNESS: single
　　　　　　　　( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:46:

AACATGATCC GGATCTCAGC C　　　　　　　　　　　　　　　　　　　　　　　　　　　　21

( 2 ) INFORMATION FOR SEQ ID NO:47:

( i ) SEQUENCE CHARACTERISTICS:
　　　　　　　　( A ) LENGTH: 21 base pairs
　　　　　　　　( B ) TYPE: nucleic acid
　　　　　　　　( C ) STRANDEDNESS: single
　　　　　　　　( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:47:

TCCTCTCTGA AACTTGGCTT T　　　　　　　　　　　　　　　　　　　　　　　　　　　　21

( 2 ) INFORMATION FOR SEQ ID NO:48:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:48:

CAAGCGGATG ATGTCTTTAT G        21

( 2 ) INFORMATION FOR SEQ ID NO:49:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:49:

GAAAATCATC TGCACGTTCA C        21

( 2 ) INFORMATION FOR SEQ ID NO:50:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:50:

GTCCAGGGGG TTGGAGGAAA AT        22

( 2 ) INFORMATION FOR SEQ ID NO:51:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:51:

ACGGCGGAAA TTCAGACTCC T        21

( 2 ) INFORMATION FOR SEQ ID NO:52:

( i ) SEQUENCE CHARACTERISTICS:
        ( A ) LENGTH: 21 base pairs (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:52:

CATGCCAATT CGGTTTGTGC T                                                         21

(2) INFORMATION FOR SEQ ID NO:53:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:53:

GAACATCCCA TAAAGATCTC G                                                         21

(2) INFORMATION FOR SEQ ID NO:54:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:54:

GTACGCTCAG TATGAGAGGT A                                                         21

(2) INFORMATION FOR SEQ ID NO:55:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:55:

CCAGCCTGCT GAGAGCCC                                                             18

(2) INFORMATION FOR SEQ ID NO:56:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:56:

CAGTGGACTC AGCGTCAG 18

(2) INFORMATION FOR SEQ ID NO:57:

(i) SEQUENCE CHARACTERISTICS:
        (A) LENGTH: 23 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:57:

Tyr Gly Gln Cys Trp Val Phe Ala Gly Thr Leu Asn Thr Ala Leu Arg
1               5                   10                  15

Ser Leu Gly Ile Pro Ser Arg
            20

(2) INFORMATION FOR SEQ ID NO:58:

(i) SEQUENCE CHARACTERISTICS:
        (A) LENGTH: 23 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:58:

Phe Gly Gln Cys Trp Val Phe Ala Gly Thr Leu Asn Thr Val Leu Arg
1               5                   10                  15

Cys Leu Gly Val Arg Ser Arg
            20

(2) INFORMATION FOR SEQ ID NO:59:

(i) SEQUENCE CHARACTERISTICS:
        (A) LENGTH: 23 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:59:

Phe Gly Gln Cys Trp Val Phe Ala Gly Thr Leu Asn Thr Val Leu Arg

```
          1               5                    10                    15
      Cys  Leu  Gly  Val  Arg  Ser  Arg
                         20
```

(2) INFORMATION FOR SEQ ID NO:60:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:60:

```
      Ala  His  Asp  Thr  Asp  Arg  Asn  Leu  Ser  Val  Asp  Val  Tyr  Tyr  Asp
      1               5                         10                        15
```

(2) INFORMATION FOR SEQ ID NO:61:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:61:

```
      Ala  His  Asp  Thr  Asp  Arg  Asn  Leu  Ser  Val  Asp  Val  Tyr  Tyr  Asp
      1               5                         10                        15
```

(2) INFORMATION FOR SEQ ID NO:62:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:62:

```
      Glu  Gly  Asp  Val  Asp  Leu  Asn  Phe  Xaa  Val  Met  Pro  Phe  Ile  Tyr
      1               5                         10                        15
```

(2) INFORMATION FOR SEQ ID NO:63:

(i) SEQUENCE CHARACTERISTICS:
        (A) LENGTH: 16 amino acids
        (B) TYPE: amino acid
        (C) STRANDEDNESS: single
        (D) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:63:

Arg Ser Gln Gly Val Phe Gln Cys Gly Pro Ala Ser Val Ile Gly Val
1               5                   10                  15

( 2 ) INFORMATION FOR SEQ ID NO:64:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:64:

Arg Ser Gln Gly Val Phe Gln Cys Gly Pro Ala Ser Val Asn Ala Ile
1               5                   10                  15

( 2 ) INFORMATION FOR SEQ ID NO:65:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:65:

Val Ser Gln Gly Val Phe Gln Cys Gly Pro Ala Ser Val Ile Ala Val
1               5                   10                  15

( 2 ) INFORMATION FOR SEQ ID NO:66:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:66:

Gly Ser Asp Ser Val Trp Asn Phe His Val Trp Asn Glu Gly Trp Phe
1               5                   10                  15

Val Arg ( 2 ) INFORMATION FOR SEQ ID NO:67:

( i ) SEQUENCE CHARACTERISTICS:
    ( A ) LENGTH: 18 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:67:

```
Gly  Ser  Asp  Ser  Val  Trp  Asn  Phe  His  Val  Trp  Asn  Glu  Gly  Trp  Phe
1                   5                        10                       15
Val  Arg
```

( 2 ) INFORMATION FOR SEQ ID NO:68:

( i ) SEQUENCE CHARACTERISTICS:
    ( A ) LENGTH: 18 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:68:

```
Gly  Ser  Asp  Ser  Val  Trp  Asn  Phe  His  Val  Trp  Asn  Val  Ala  Trp  Phe
1                   5                        10                       15
Val  Arg
```

( 2 ) INFORMATION FOR SEQ ID NO:69:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:69:

```
Leu  Gly  Thr  Phe  Ile  Leu  Leu  Phe  Asn  Pro  Trp  Leu  Asn  Val  Asp  Ser
1                   5                        10                       15
Val  Phe  Met  Gly
                20
```

( 2 ) INFORMATION FOR SEQ ID NO:70:

( i ) SEQUENCE CHARACTERISTICS:
    ( A ) LENGTH: 20 amino acids
    ( B ) TYPE: amino acid (C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:70:

Leu Gly Thr Phe Val Leu Leu Phe Asn Pro Trp Leu Gln Ala Asp Asp
1               5                   10                  15

Val Phe Met Ser
            20

(2) INFORMATION FOR SEQ ID NO:71:

(i) SEQUENCE CHARACTERISTICS:
    (A) LENGTH: 20 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:71:

Leu Gly Thr Phe Val Leu Leu Phe Asn Pro Trp Leu Gln Ala Asp Asp
1               5                   10                  15

Val Phe Met Ser
            20

(2) INFORMATION FOR SEQ ID NO:72:

(i) SEQUENCE CHARACTERISTICS:
    (A) LENGTH: 28 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:72:

Ser Met Gly Leu Glu Thr Glu Glu Gln Glu Pro Ser Ile Ile Gly Lys
1               5                   10                  15

Leu Lys Val Ala Gly Met Leu Ala Val Gly Lys Glu
            20                  25

(2) INFORMATION FOR SEQ ID NO:73:

(i) SEQUENCE CHARACTERISTICS:
    (A) LENGTH: 28 amino acids
    (B) TYPE: amino acid
    (C) STRANDEDNESS: single
    (D) TOPOLOGY: linear (ii) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:73:

| Ser | Arg | Asn | Pro | Glu | Gly | Glu | Asp | Lys | Glu | Pro | Ser | Ile | Ser | Gly | Lys |
|---|---|---|---|---|---|---|---|---|---|---|---|---|---|---|---|
| 1 | | | | 5 | | | | | 10 | | | | | 15 | |

| Phe | Lys | Val | Thr | Gly | Ile | Leu | Ala | Val | Gly | Lys | Glu |
|---|---|---|---|---|---|---|---|---|---|---|---|
| | | | 20 | | | | | 25 | | | |

(2) INFORMATION FOR SEQ ID NO:74:

(i) SEQUENCE CHARACTERISTICS:
 (A) LENGTH: 28 amino acids
 (B) TYPE: amino acid
 (C) STRANDEDNESS: single
 (D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:74:

| Ala | Gln | Arg | Ser | Pro | Gly | Arg | Glu | Gln | Ala | Pro | Ser | Ile | Ser | Gly | Arg |
|---|---|---|---|---|---|---|---|---|---|---|---|---|---|---|---|
| 1 | | | | 5 | | | | | 10 | | | | | 15 | |

| Phe | Lys | Val | Asn | Gly | Val | Leu | Ala | Val | Gly | Gln | Glu |
|---|---|---|---|---|---|---|---|---|---|---|---|
| | | | 20 | | | | | 25 | | | |

(2) INFORMATION FOR SEQ ID NO:75:

(i) SEQUENCE CHARACTERISTICS:
 (A) LENGTH: 8 amino acids
 (B) TYPE: amino acid
 (C) STRANDEDNESS: single
 (D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:75:

| Ile | Ser | Tyr | Ala | Gln | Tyr | Glu | Arg |
|---|---|---|---|---|---|---|---|
| 1 | | | | 5 | | | |

(2) INFORMATION FOR SEQ ID NO:76:

(i) SEQUENCE CHARACTERISTICS:
 (A) LENGTH: 8 amino acids
 (B) TYPE: amino acid
 (C) STRANDEDNESS: single
 (D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:76:

Ile Ala Tyr Ser Gln Tyr Glu Arg
            1               5

( 2 ) INFORMATION FOR SEQ ID NO:77:

( i ) SEQUENCE CHARACTERISTICS:
                ( A ) LENGTH: 8 amino acids
                ( B ) TYPE: amino acid
                ( C ) STRANDEDNESS: single
                ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:77:

Ile Thr Tyr Ala Gln Tyr Glu Lys
            1               5

( 2 ) INFORMATION FOR SEQ ID NO:78:

( i ) SEQUENCE CHARACTERISTICS:
                ( A ) LENGTH: 6 amino acids
                ( B ) TYPE: amino acid
                ( C ) STRANDEDNESS: single
                ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:78:

Ile Thr Ala Val Cys Lys
            1               5

( 2 ) INFORMATION FOR SEQ ID NO:79:

( i ) SEQUENCE CHARACTERISTICS:
                ( A ) LENGTH: 6 amino acids
                ( B ) TYPE: amino acid
                ( C ) STRANDEDNESS: single
                ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:79:

Ile Ser Ala Val Cys Lys
            1               5

( 2 ) INFORMATION FOR SEQ ID NO:80:

( i ) SEQUENCE CHARACTERISTICS:
                ( A ) LENGTH: 6 amino acids
                ( B ) TYPE: amino acid
                ( C ) STRANDEDNESS: single
                ( D ) TOPOLOGY: linear ( i i ) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:80:

Thr Thr Ala Ile Cys Lys
1               5

(2) INFORMATION FOR SEQ ID NO:81:

(i) SEQUENCE CHARACTERISTICS:
   (A) LENGTH: 7 amino acids
   (B) TYPE: amino acid
   (C) STRANDEDNESS: single
   (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:81:

Phe Asp Ile Leu Pro Ser Arg
1               5

(2) INFORMATION FOR SEQ ID NO:82:

(i) SEQUENCE CHARACTERISTICS:
   (A) LENGTH: 7 amino acids
   (B) TYPE: amino acid
   (C) STRANDEDNESS: single
   (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:82:

Phe Glu Ile Phe Pro Thr Arg
1               5

(2) INFORMATION FOR SEQ ID NO:83:

(i) SEQUENCE CHARACTERISTICS:
   (A) LENGTH: 7 amino acids
   (B) TYPE: amino acid
   (C) STRANDEDNESS: single
   (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:83:

Phe Glu Ile Leu Pro Thr Arg
1               5

(2) INFORMATION FOR SEQ ID NO:84:

( i ) SEQUENCE CHARACTERISTICS:
  ( A ) LENGTH: 15 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:84:

Lys Pro Val Asn Val Gln Met Leu Phe Ser Asn Pro Leu Asp Glu
1               5                   10                  15

( 2 ) INFORMATION FOR SEQ ID NO:85:

( i ) SEQUENCE CHARACTERISTICS:
    ( A ) LENGTH: 15 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:85:

Lys Pro Val Asn Val Gln Met Ile Phe Ser Asn Pro Leu Asp Gln
1               5                   10                  15

( 2 ) INFORMATION FOR SEQ ID NO:86:

( i ) SEQUENCE CHARACTERISTICS:
    ( A ) LENGTH: 15 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:86:

Lys Pro Val Asn Val Gln Cys Leu Phe Ser Asn Pro Leu Asp Gly
1               5                   10                  15

( 2 ) INFORMATION FOR SEQ ID NO:87:

( i ) SEQUENCE CHARACTERISTICS:
    ( A ) LENGTH: 15 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:87:

Asp Ile Ile Leu Asp Asn Pro Thr Leu Thr Leu Glu Val Leu Asn
1               5                   10                  15

( 2 ) INFORMATION FOR SEQ ID NO:88:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:88:

Asp Val Ile Leu Asp Asn Pro Thr Leu Thr Leu Glu Val Leu Asp
1               5                   10                  15

( 2 ) INFORMATION FOR SEQ ID NO:89:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:89:

Asp Val Ile Leu Asp Asn Pro Thr Leu Thr Leu Glu Val Leu Asp
1               5                   10                  15

( 2 ) INFORMATION FOR SEQ ID NO:90:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:90:

Asp Cys Val Leu Met Val Glu Gly Ser Gly Leu Leu Leu
1               5                   10

( 2 ) INFORMATION FOR SEQ ID NO:91:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:91:

```
Asn Cys Val Leu Leu Val Glu Gly Ser Gly Cys Ser Val
1               5                   10
```

(2) INFORMATION FOR SEQ ID NO:92:

(i) SEQUENCE CHARACTERISTICS:
        (A) LENGTH: 13 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: internal (x i) SEQUENCE DESCRIPTION: SEQ ID NO:92:

```
Asp Leu Val Leu Asp Phe Glu Gly Ser Cys Leu Leu Arg
1               5                   10
```

(2) INFORMATION FOR SEQ ID NO:93:

(i) SEQUENCE CHARACTERISTICS:
        (A) LENGTH: 9551 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (i x) FEATURE:
        (A) NAME/KEY: CDS
        (B) LOCATION: 1507..1644

(i x) FEATURE:
        (A) NAME/KEY: intron
        (B) LOCATION: 1645..2511

(i x) FEATURE:
        (A) NAME/KEY: CDS
        (B) LOCATION: 2512..8070

(x i) SEQUENCE DESCRIPTION: SEQ ID NO:93:

```
AACAAGCCAT TTGTGGAGAC AGAGGTGGAG CTGGGCTTGG TTAGGAATGA ATCAGGCCAT    60
TCCACAGAGT GGGTGTCTCC TTCCCAAGTT GCTTTCCAGG GCACAATTAA AACCCCTATA   120
AAAGGCCCAG CTCCCAGTTA CCCAGTACAC TTGCCTGTGG TGTCAGCAAG CACTGTCGAC   180
TTCTTCCTCT GGTGAAGTGG GTAAGTCCCA TTCTGTGGGA TCGTGGTCTT CTTTATGATT   240
CTCCATTTTT ATAGCTATTT CAGATGTTGG GATATGGGGG GAGGTTCCAT GTGCCAGAAG   300
GTATCAGTAT TGCAGGGATA AATAAACTAT CACTAACTCT ATCCATCTT CTTATGGTTG    360
GAGCCATCAC TTGAACTGAA GCATGACCCT TCTCCTTGGG CTCTGAACTC TATACTTCTG   420
CACATCAAGG ATGATCATGT GTGGCTCTGA TAGGGTTCAT CTTCCTAAAA ACTGCTATCT   480
```

| | | | | | | |
|---|---|---|---|---|---|---|
| CAAAAGTTTG | CCAGCCTTCT | GTTCTCTTTT | ACATTGGTTC | TACCTAATAT | GGGCCATATT | 540 |
| CATACAGTCA | CAGCATTTAA | GGTACTGGAG | TTGAGAAGTA | CATAAAGAAG | TCAGCTAGAT | 600 |
| GAACGACTAC | CTTATCCCAC | CAGCAAAGCC | ATTCCATGTA | TTCTTATAAC | ATTGATCTAC | 660 |
| TGCTGGCTAA | TGTTTTATAA | AAAGCCAAGA | TTCCAATGAT | GCATTTGGGT | TTAACAAAAC | 720 |
| CAATATCATT | CACAGTTTTC | TGGATTCCGT | TTGGTTTAGA | AAGGACCTCT | CAGAAGCTTT | 780 |
| CAATACTTCA | ATATCCGAAT | ATCTTACTAT | ATCTGAGTTG | AGGCAGGTAA | TATACAGTCT | 840 |
| CTGTTTTCTG | CATTTGTGTA | TCTGAATGTT | ACATGCCATC | TTTTGACTAG | GAAGAAGTAC | 900 |
| TATTTAATCT | TAGAATTGCT | GACTTACAAA | TTATATTCTA | TAAGAGTTCC | TAAATCCCTT | 960 |
| TATGGACTGT | AATGTTGAGG | AATCATTCAT | ATTCCCTTTT | CATTGTTCTA | TTTTCTACCA | 1020 |
| ATCGTTTGC | TGACATGGCC | TCTATCCACT | TTAAGATACT | CTCAAGTCTT | CCTTCACCTT | 1080 |
| TTGGCTTTAC | CTGTCCTCTT | CGCTCAACTT | TAAAGGAAGG | TGTGTAGCCA | TATATAAAT | 1140 |
| TTTAATTTCT | GCACTCTTCT | CTTAATTTTC | TACTCTGAAA | TACGGTGGAG | AGCTGGAAGA | 1200 |
| AAGACAGAAG | AAAAGGGCAT | AGATAATCCA | CATTGGGTGG | ACAATCAAAA | GCTGACAACA | 1260 |
| GGATAGTCTG | AAGATGATTC | CCTGGCTTGG | AATTTCTCAG | GATCGCTCTT | TCTCTTTCTG | 1320 |
| ATACAATATT | CAAATATTAA | AGTGCTCTGA | AAGTCCAGGT | TGAAATTACC | GCTATAAATT | 1380 |
| CAAATTATTT | AGGGATCTGC | CTGAAATAGT | GTGAATGAAG | CCTTCCCAAA | AGCAGAAACG | 1440 |
| GGATTTTGAT | TCTGGATCTT | ATTTTATTGT | TCTAGGTTTA | CTTGAACTTG | AAGGAAAGAA | 1500 |

| | | | | | | |
|---|---|---|---|---|---|---|
| AAAAAA ATG | TCT CCA CTT | CTG AGA AGC | ATC TGT GAC | ATC ACT GAA ATT | | 1548 |
| Met | Ser Pro Leu | Leu Arg Ser | Ile Cys Asp | Ile Thr Glu Ile | | |
| 1 | | 5 | | 10 | | |
| TTC AAT CAG | TAT GTC TCT | CAT GAT TGT | GAT GGA GCA | GCA TTA ACT AAG | | 1596 |
| Phe Asn Gln | Tyr Val Ser | His Asp Cys | Asp Gly Ala | Ala Leu Thr Lys | | |
| 15 | | 20 | | 25 | 30 | |
| AAA GAC CTG | AAG AAC CTC | CTT GAA AGG | GAA TTT GGA | GCT GTG CTT CGG | | 1644 |
| Lys Asp Leu | Lys Asn Leu | Leu Glu Arg | Glu Phe Gly | Ala Val Leu Arg | | |
| | 35 | | 40 | | 45 | |

| | | | | | | |
|---|---|---|---|---|---|---|
| GTAAGAACTA | ACAAGAAAAT | GAGATCTATT | GACTTGAGGC | TATGAGATTT | ATTCTCAGAG | 1704 |
| GAGACCAGAG | CAAGGAATGG | TGGTTTTATA | TTCATTTTAC | ACCACAACAG | GTCTACACTA | 1764 |
| CATCCCCCAT | TCATTTCTGA | GTCAAAAGGT | ACTTACTTGA | CATTGTAGTC | TGAATAATAA | 1824 |
| AGTATTTCAT | GTACTTGATG | GCATGGCATG | TGAATGAGCT | CTTCATGGGA | CATTACTACA | 1884 |
| AAAGATGTCA | AATCACACTA | GACTTGGAGG | AACTTGGAGG | AACTTAAATT | TGTTTCCAAA | 1944 |
| TTTCAAAACT | GAGATCAGCC | TGACTCTATT | AAATGGTGCT | ACCCGTAAAT | GTTTTGTTCT | 2004 |
| GTTTTCTAAT | ATGGAATAGA | AACCAAATCA | AGAATACTGG | CTGCTTCAGA | CAGAAATGGC | 2064 |
| TACTGCAAAT | CCTCATAAAT | TTCTATTGTA | TCTCTCTCAA | GGATGAGTTC | ATTCTTTCTC | 2124 |
| AATTAAAGCG | AACTTGTGTT | ATTCTTTCTT | GATGTTGAGT | AGCTTTGTTA | ATTTACACAC | 2184 |
| AAGTTCACGA | TGCTGTTTTG | AATCTTCACC | TCAGGCTCTG | CTCTAAGGTG | CGTAGGCTTA | 2244 |
| CCTGCTATCT | ACTTGTGTCT | CTCTTCCTGC | TTCCTTAGGT | TGATCAGCA | CTAAATTACG | 2304 |
| AGATGTAAAA | ATTTCAAACG | AATATATGCT | TTAAAGTGAG | GGTTCACATT | TTACATGGGG | 2364 |
| ACAAACTTG | ATACACACTG | GACATTTTTC | TAATTGCTCT | GAATGTCTCT | TGAATGTCAG | 2424 |
| CATAGCATAA | AATATATCAT | GTGTGAATAT | AATTTTACCA | CCTGTAAATA | GTGCATTGTA | 2484 |
| AAATTTTTGT | TTTTCACCAT | TTTATAG AGA | CCA CAT GAC | CCT AAG ACG GTA | | 2535 |
| | | Arg | Pro His Asp | Pro Lys Thr Val | | |
| | | 1 | | 5 | | |

| | | | | | | |
|---|---|---|---|---|---|---|
| GAT CTG ATC | CTG GAA CTT | CTG GAT CGT | GAC AGT AAT | GGG CGT GTC GAT | | 2583 |
| Asp Leu Ile | Leu Glu Leu | Leu Asp Arg | Asp Ser Asn | Gly Arg Val Asp | | |

|  |  |
|---|---|
| TTC AAC GAA TTC CTC CTA TTT ATT TTC AAA GTG GCT CAA GCT TGT TAC<br>Phe Asn Glu Phe Leu Leu Phe Ile Phe Lys Val Ala Gln Ala Cys Tyr<br>25                              30                            35                            40 | 2631 |
| TAT GCT CTC GGC CAG GCC ACG GGA CTG GAT GAG GAG AAG CGA GCC CGG<br>Tyr Ala Leu Gly Gln Ala Thr Gly Leu Asp Glu Glu Lys Arg Ala Arg<br>                              45                            50                            55 | 2679 |
| TGT GAC GGA AAG GAG AGC CTG TTA CAA GAT CGA CGG ACA GAA GAA GAC<br>Cys Asp Gly Lys Glu Ser Leu Leu Gln Asp Arg Arg Thr Glu Glu Asp<br>                              60                            65                            70 | 2727 |
| CAA AGG AGA TTC GAG CCC CGG GAC AGA CAA CTG GAA GAA GAA CCT GGG<br>Gln Arg Arg Phe Glu Pro Arg Asp Arg Gln Leu Glu Glu Glu Pro Gly<br>       75                             80                            85 | 2775 |
| CAA CGA CGC AGG CAG AAG AGG CAG GAA CAG GAG AGG GAG CTA GCT GAG<br>Gln Arg Arg Arg Gln Lys Arg Gln Glu Gln Glu Arg Glu Leu Ala Glu<br>       90                             95                            100 | 2823 |
| GGA GAG GAG CAA AGT GAG AAA CAA GAG CGA CTT GAA CAG CGC GAC AGG<br>Gly Glu Glu Gln Ser Glu Lys Gln Glu Arg Leu Glu Gln Arg Asp Arg<br>105                            110                          115                          120 | 2871 |
| CAG CGC CGC GAC GAG GAG CTG TGG CGG CAA AGG CAA GAA TGG CAA GAA<br>Gln Arg Arg Asp Glu Glu Leu Trp Arg Gln Arg Gln Glu Trp Gln Glu<br>                              125                          130                          135 | 2919 |
| CGG GAA GAG CGC CGT GCA GAG GAA GAG CAG CTG CAG AGT TGC AAA GGT<br>Arg Glu Glu Arg Arg Ala Glu Glu Glu Gln Leu Gln Ser Cys Lys Gly<br>               140                          145                          150 | 2967 |
| CAC GAA ACT GAG GAG TTT CCA GAC GAA GAG CAA CTG CGA AGG CGG GAG<br>His Glu Thr Glu Glu Phe Pro Asp Glu Glu Gln Leu Arg Arg Arg Glu<br>               155                          160                          165 | 3015 |
| CTG CTG GAG CTG AGG AGG AAG GGC CGC GAG GAG AAA CAG CAG CAA AGG<br>Leu Leu Glu Leu Arg Arg Lys Gly Arg Glu Glu Lys Gln Gln Gln Arg<br>170                            175                          180 | 3063 |
| CGA GAG CGC CAA GAC AGA GTG TTC CAG GAG GAA GAA GAG AAA GAG TGG<br>Arg Glu Arg Gln Asp Arg Val Phe Gln Glu Glu Glu Glu Lys Glu Trp<br>185                            190                          195                          200 | 3111 |
| AGG AAG CGC GAG ACA GTG CTC CGG AAG GAA GAA GAG AAG TTG CAG GAA<br>Arg Lys Arg Glu Thr Val Leu Arg Lys Glu Glu Glu Lys Leu Gln Glu<br>                              205                          210                          215 | 3159 |
| GAG GAG CCG CAG CGG CAA AGA GAG CTC CAG GAG GAA GAA GAG CAG CTA<br>Glu Glu Pro Gln Arg Gln Arg Glu Leu Gln Glu Glu Glu Glu Gln Leu<br>                              220                          225                          230 | 3207 |
| CGG AAG CTG GAG CGG CAA GAG CTG AGG AGG GAG CGC CAG GAG GAA GAG<br>Arg Lys Leu Glu Arg Gln Glu Leu Arg Arg Glu Arg Gln Glu Glu Glu<br>               235                          240                          245 | 3255 |
| CAG CAG CAG CAA AGG CTG AGG CGC GAG CAG CAA CTA AGG CGC AAG CAG<br>Gln Gln Gln Gln Arg Leu Arg Arg Glu Gln Gln Leu Arg Arg Lys Gln<br>               250                          255                          260 | 3303 |
| GAG GAG GAG AGG CGC GAG CAG CAG GAG GAG AGG CGC GAG CAG CAG GAG<br>Glu Glu Glu Arg Arg Glu Gln Gln Glu Glu Arg Arg Glu Gln Gln Glu<br>265                            270                          275                          280 | 3351 |
| AGG CGC GAG CAG CAG GAG GAG AGG CGC GAG CAG CAG CTG AGG CGC GAG<br>Arg Arg Glu Gln Gln Glu Glu Arg Arg Glu Gln Gln Leu Arg Arg Glu<br>                              285                          290                          295 | 3399 |
| CAG GAG GAG AGG CGC GAG CAG CAG CTG AGG CGC GAG CAG GAG GAG GAG<br>Gln Glu Glu Arg Arg Glu Gln Gln Leu Arg Arg Glu Gln Glu Glu Glu<br>                              300                          305                          310 | 3447 |
| AGG CGC GAG CAG CAG CTG AGG CGC GAG CAG GAG GAG GAG AGG CGC GAG<br>Arg Arg Glu Gln Gln Leu Arg Arg Glu Gln Glu Glu Glu Arg Arg Glu<br>               315                          320                          325 | 3495 |
| CAG CAG CTG AGG CGC GAG CAG GAG GAG GAG AGG CGC GAG CAG CAG CTG<br>Gln Gln Leu Arg Arg Glu Gln Glu Glu Glu Arg Arg Glu Gln Gln Leu | 3543 |

|  |  |  |  |  | 330 |  |  |  |  | 335 |  |  |  |  | 340 |  |  |  |
|---|---|---|---|---|---|---|---|---|---|---|---|---|---|---|---|---|---|---|

AGG CGC GAG CAG CAG CTG AGG CGC GAG CAG CAG CTG AGG CGC GAG CAG   3591
Arg Arg Glu Gln Gln Leu Arg Arg Glu Gln Gln Leu Arg Arg Glu Gln
345             350             355             360

CAG CTG AGG CGC GAG CAG CAG CTG AGG CGC GAG CAG CAG CTG AGG CGC   3639
Gln Leu Arg Arg Glu Gln Gln Leu Arg Arg Glu Gln Gln Leu Arg Arg
        365             370             375

GAG CAG CAG CTG AGG CGC GAG CAG CAG CTG AGG CGC GAG CAG CAG CTG   3687
Glu Gln Gln Leu Arg Arg Glu Gln Gln Leu Arg Arg Glu Gln Gln Leu
            380             385             390

AGG CGC GAG CAG CAG CTG AGG CGC GAG CAG GAG GAG GAG AGG CAC GAG   3735
Arg Arg Glu Gln Gln Leu Arg Arg Glu Gln Glu Glu Glu Arg His Glu
395             400             405

CAG AAG CAC GAG CAG GAG AGG CGC GAG CAG CGG CTG AAG CGC GAG CAG   3783
Gln Lys His Glu Gln Glu Arg Arg Glu Gln Arg Leu Lys Arg Glu Gln
410             415             420

GAG GAG AGG CGC GAT TGG CTG AAG CGC GAG GAG GAG ACG GAG AGG CAC   3831
Glu Glu Arg Arg Asp Trp Leu Lys Arg Glu Glu Glu Thr Glu Arg His
425             430             435             440

GAG CAG GAG AGG CGC AAG CAG CAG CTG AAG CGC GAC CAG GAG GAG GAG   3879
Glu Gln Glu Arg Arg Lys Gln Gln Leu Lys Arg Asp Gln Glu Glu Glu
            445             450             455

AGG CGC GAA CGT TGG CTG AAG CTC GAG GAG GAG GAG AGG CGC GAG CAG   3927
Arg Arg Glu Arg Trp Leu Lys Leu Glu Glu Glu Glu Arg Arg Glu Gln
            460             465             470

CAG GAG AGG CGC GAG CAG CAA CTA AGG CGG GAG CAA GAG GAG AGG CGC   3975
Gln Glu Arg Arg Glu Gln Gln Leu Arg Arg Glu Gln Glu Glu Arg Arg
        475             480             485

GAG CAG CGG CTG AAG CGC CAG GAG GAG GAA GAG AGG CTC CAG CAG CGG   4023
Glu Gln Arg Leu Lys Arg Gln Glu Glu Glu Glu Arg Leu Gln Gln Arg
        490             495             500

TTG AGG AGC GAG CAA CAA CTA AGA CGC GAG CAG GAG GAG AGG CTC GAG   4071
Leu Arg Ser Glu Gln Gln Leu Arg Arg Glu Gln Glu Glu Arg Leu Glu
505             510             515             520

CAG CTG CTG AAG CGC GAG GAG GAG AAG AGG CTC GAG CAG GAG AGG CGA   4119
Gln Leu Leu Lys Arg Glu Glu Glu Lys Arg Leu Glu Gln Glu Arg Arg
            525             530             535

GAG CAG CGG CTG AAG CGC GAG CAG GAG GAG AGG CGC GAT CAG CTG CTG   4167
Glu Gln Arg Leu Lys Arg Glu Gln Glu Glu Arg Arg Asp Gln Leu Leu
        540             545             550

AAG CGC GAG GAG GAG AGG CGC CAG CAG CGG CTG AAG CGC GAG CAG GAA   4215
Lys Arg Glu Glu Glu Arg Arg Gln Gln Arg Leu Lys Arg Glu Gln Glu
        555             560             565

GAG AGG CTC GAG CAG CGA CTG AAG CGC GAG GAG GTG GAG AGA CTC GAG   4263
Glu Arg Leu Glu Gln Arg Leu Lys Arg Glu Glu Val Glu Arg Leu Glu
570             575             580

CAG GAG GAG AGG CGC GAC GAG CGG CTG AAG CGC GAG GAG CCG GAG GAA   4311
Gln Glu Glu Arg Arg Asp Glu Arg Leu Lys Arg Glu Glu Pro Glu Glu
585             590             595             600

GAG AGG CGC CAC GAG CTG CTG AAG AGC GAG GAG CAG GAG GAG AGG CGC   4359
Glu Arg Arg His Glu Leu Leu Lys Ser Glu Glu Gln Glu Glu Arg Arg
            605             610             615

CAC GAG CAA CTG AGG CGC GAG CAG CAG GAA AGG CGC GAG CAG CGG CTG   4407
His Glu Gln Leu Arg Arg Glu Gln Gln Glu Arg Arg Glu Gln Arg Leu
        620             625             630

AAG CGC GAG GAG GAG GAA GAG AGG CTC GAG CAG CGG CTG AAG CGC GAG   4455
Lys Arg Glu Glu Glu Glu Glu Arg Leu Glu Gln Arg Leu Lys Arg Glu
        635             640             645

CAT GAG GAA GAG AGG CGC GAG CAG GAG CTA GCT GAG GAG GAG CAG GAA   4503
His Glu Glu Glu Arg Arg Glu Gln Glu Leu Ala Glu Glu Glu Gln Glu

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 650 |     |     |     |     | 655 |     |     |     |     |     | 660 |     |     |      |
| CAG | GCC | CGG | GAG | CGG | ATT | AAG | AGC | CGC | ATC | CCG | AAG | TGG | CAG | TGG | CAG | 4551 |
| Gln | Ala | Arg | Glu | Arg | Ile | Lys | Ser | Arg | Ile | Pro | Lys | Trp | Gln | Trp | Gln |      |
| 665 |     |     |     |     | 670 |     |     |     |     | 675 |     |     |     |     | 680 |      |
| CTA | GAA | AGC | GAG | GCC | GAC | GCA | CGG | CAA | AGC | AAA | GTC | TTA | CTC | GAG | GCC | 4599 |
| Leu | Glu | Ser | Glu | Ala | Asp | Ala | Arg | Gln | Ser | Lys | Val | Leu | Leu | Glu | Ala |      |
|     |     |     |     | 685 |     |     |     |     | 690 |     |     |     |     | 695 |     |      |
| CCG | CAA | GCA | GGA | AGG | GCA | GAG | GCG | CCG | CAA | GAG | CAG | GAG | GAA | AAG | AGG | 4647 |
| Pro | Gln | Ala | Gly | Arg | Ala | Glu | Ala | Pro | Gln | Glu | Gln | Glu | Glu | Lys | Arg |      |
|     |     |     | 700 |     |     |     |     | 705 |     |     |     |     | 710 |     |     |      |
| CGG | CGC | GAG | AGT | GAG | CTG | CAA | TGG | CAG | GAG | GAG | GAA | CGG | GCT | CAC | CGG | 4695 |
| Arg | Arg | Glu | Ser | Glu | Leu | Gln | Trp | Gln | Glu | Glu | Glu | Arg | Ala | His | Arg |      |
|     |     |     | 715 |     |     |     | 720 |     |     |     |     | 725 |     |     |     |      |
| CAG | CAG | CAG | GAA | GAG | GAG | CAG | CGC | CGG | GAC | TTC | ACA | TGG | CAG | TGG | CAG | 4743 |
| Gln | Gln | Gln | Glu | Glu | Glu | Gln | Arg | Arg | Asp | Phe | Thr | Trp | Gln | Trp | Gln |      |
|     |     | 730 |     |     |     |     | 735 |     |     |     | 740 |     |     |     |     |      |
| GCG | GAG | GAA | AAG | AGC | GAG | AGG | GGC | CGT | CAG | AGG | CTG | TCG | GCC | AGG | CCC | 4791 |
| Ala | Glu | Glu | Lys | Ser | Glu | Arg | Gly | Arg | Gln | Arg | Leu | Ser | Ala | Arg | Pro |      |
| 745 |     |     |     |     | 750 |     |     |     |     | 755 |     |     |     |     | 760 |      |
| CCA | TTG | CGG | GAG | CAG | CGG | GAG | AGG | CAG | CTG | AGG | GCC | GAG | GAG | CGC | CAG | 4839 |
| Pro | Leu | Arg | Glu | Gln | Arg | Glu | Arg | Gln | Leu | Arg | Ala | Glu | Glu | Arg | Gln |      |
|     |     |     |     | 765 |     |     |     |     | 770 |     |     |     |     | 775 |     |      |
| CAG | CGG | GAA | CAA | CGG | TTT | CTC | CCG | GAG | GAG | GAG | AAG | GAG | CAG | CGC | GGC | 4887 |
| Gln | Arg | Glu | Gln | Arg | Phe | Leu | Pro | Glu | Glu | Glu | Lys | Glu | Gln | Arg |     |      |
|     |     |     | 780 |     |     |     |     | 785 |     |     |     |     | 790 |     |     |      |
| GGC | CGC | CAG | CGA | CGC | GAG | AGG | GAG | AAA | GAG | CTG | CAG | TTC | CTG | GAG | GAA | 4935 |
| Gly | Arg | Gln | Arg | Arg | Glu | Arg | Glu | Lys | Glu | Leu | Gln | Phe | Leu | Glu | Glu |      |
|     |     | 795 |     |     |     |     | 800 |     |     |     |     | 805 |     |     |     |      |
| GAG | GAG | CAG | CTC | CAG | CGG | CGG | GAG | CGT | GCC | CAA | CAG | CTC | CAG | GAG | GAG | 4983 |
| Glu | Glu | Gln | Leu | Gln | Arg | Arg | Glu | Arg | Ala | Gln | Gln | Leu | Gln | Glu | Glu |      |
|     |     | 810 |     |     |     |     | 815 |     |     |     |     | 820 |     |     |     |      |
| GAG | GAC | GGC | CTC | CAG | GAG | GAT | CAG | GAG | AGG | AGG | CGA | CAG | GAG | CAG | CGC | 5031 |
| Glu | Asp | Gly | Leu | Gln | Glu | Asp | Gln | Glu | Arg | Arg | Arg | Gln | Glu | Gln | Arg |      |
| 825 |     |     |     |     | 830 |     |     |     |     | 835 |     |     |     |     | 840 |      |
| CGC | GAC | CAA | AAA | TGG | AGG | TGG | CAA | CTA | GAA | GAA | GAA | AGG | AAG | AGA | CGC | 5079 |
| Arg | Asp | Gln | Lys | Trp | Arg | Trp | Gln | Leu | Glu | Glu | Glu | Arg | Lys | Arg | Arg |      |
|     |     |     |     | 845 |     |     |     |     | 850 |     |     |     |     | 855 |     |      |
| CGC | CAC | ACG | CTG | TAC | GCC | AAG | CCA | GCC | CTA | CAA | GAG | CAG | CTG | AGG | AAG | 5127 |
| Arg | His | Thr | Leu | Tyr | Ala | Lys | Pro | Ala | Leu | Gln | Glu | Gln | Leu | Arg | Lys |      |
|     |     |     | 860 |     |     |     |     | 865 |     |     |     |     | 870 |     |     |      |
| GAA | CAG | CAG | CTG | CTG | CAG | GAG | GAG | GAG | GAG | GAG | CTA | CAG | AGA | GAG | GAG | 5175 |
| Glu | Gln | Gln | Leu | Leu | Gln | Glu | Glu | Glu | Glu | Glu | Leu | Gln | Arg | Glu | Glu |      |
|     |     | 875 |     |     |     |     | 880 |     |     |     |     | 885 |     |     |     |      |
| CGC | GAG | AAG | AGA | AGG | CGC | CAA | GAA | CAG | GAG | AGA | CAA | TAC | CGC | GAG | GAA | 5223 |
| Arg | Glu | Lys | Arg | Arg | Arg | Gln | Glu | Gln | Glu | Arg | Gln | Tyr | Arg | Glu | Glu |      |
|     |     | 890 |     |     |     |     | 895 |     |     |     |     | 900 |     |     |     |      |
| GAG | CAG | CTG | CAG | CAG | GAG | GAA | GAG | CAG | CTG | CTG | AGA | GAG | GAA | CGG | GAG | 5271 |
| Glu | Gln | Leu | Gln | Gln | Glu | Glu | Glu | Gln | Leu | Leu | Arg | Glu | Glu | Arg | Glu |      |
| 905 |     |     |     |     | 910 |     |     |     |     | 915 |     |     |     |     | 920 |      |
| AAA | AGA | AGA | CGC | CAG | GAG | CGG | GAA | AGG | CAA | TAT | CGG | AAG | GAT | AAG | AAG | 5319 |
| Lys | Arg | Arg | Arg | Gln | Glu | Arg | Glu | Arg | Gln | Tyr | Arg | Lys | Asp | Lys | Lys |      |
|     |     |     |     | 925 |     |     |     |     | 930 |     |     |     |     | 935 |     |      |
| CTG | CAG | CAG | AAG | GAA | GAG | CAG | CTG | CTG | GGA | GAG | GAA | CCG | GAG | AAG | AGA | 5367 |
| Leu | Gln | Gln | Lys | Glu | Glu | Gln | Leu | Leu | Gly | Glu | Glu | Pro | Glu | Lys | Arg |      |
|     |     |     | 940 |     |     |     |     | 945 |     |     |     |     | 950 |     |     |      |
| AGG | CGC | CAG | GAG | CGG | GAG | AAA | AAA | TAC | CGC | GAG | GAA | GAG | GAG | TTG | CAG | 5415 |
| Arg | Arg | Gln | Glu | Arg | Glu | Lys | Lys | Tyr | Arg | Glu | Glu | Glu | Glu | Leu | Gln |      |
|     |     | 955 |     |     |     |     | 960 |     |     |     |     | 965 |     |     |     |      |
| CAG | GAG | GAA | GAG | CAG | CTG | CTG | AGA | GAG | GAA | CGG | GAG | AAG | AGA | AGG | CGC | 5463 |
| Gln | Glu | Glu | Glu | Gln | Leu | Leu | Arg | Glu | Glu | Arg | Glu | Lys | Arg | Arg | Arg |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 970 |     |     |     |     | 975 |     |     |     |     | 980 |     |     |     |      |
| CAG | GAG | TGG | GAG | AGG | CAG | TAC | CGC | AAA | AAA | GAC | GAG | CTG | CAG | CAG | GAA | 5511 |
| Gln | Glu | Trp | Glu | Arg | Gln | Tyr | Arg | Lys | Lys | Asp | Glu | Leu | Gln | Gln | Glu |      |
| 985 |     |     |     | 990 |     |     |     |     | 995 |     |     |     |     | 1000|     |      |
| GAA | GAG | CAG | CTG | CTG | AGA | GAG | GAA | CGG | GAG | AAA | AGA | AGA | CTC | CAG | GAG | 5559 |
| Glu | Glu | Gln | Leu | Leu | Arg | Glu | Glu | Arg | Glu | Lys | Arg | Arg | Leu | Gln | Glu |      |
|     |     |     |     | 1005|     |     |     |     | 1010|     |     |     |     | 1015|     |      |
| CGG | GAG | AGG | CAA | TAT | CGG | GAG | GAA | GAG | GAG | CTG | CAG | CAG | GAG | GAA | GAG | 5607 |
| Arg | Glu | Arg | Gln | Tyr | Arg | Glu | Glu | Glu | Glu | Leu | Gln | Gln | Glu | Glu | Glu |      |
|     |     |     | 1020|     |     |     |     | 1025|     |     |     |     | 1030|     |     |      |
| CAG | CTG | CTG | GGA | GAG | GAA | CGG | GAG | ACG | AGA | AGG | CGC | CAG | GAG | CTG | GAG | 5655 |
| Gln | Leu | Leu | Gly | Glu | Glu | Arg | Glu | Thr | Arg | Arg | Arg | Gln | Glu | Leu | Glu |      |
|     |     |     | 1035|     |     |     |     | 1040|     |     |     |     | 1045|     |     |      |
| AGG | CAA | TAT | CGG | AAG | GAA | GAG | GAG | CTG | CAG | CAG | GAG | GAA | GAG | CAG | CTG | 5703 |
| Arg | Gln | Tyr | Arg | Lys | Glu | Glu | Glu | Leu | Gln | Gln | Glu | Glu | Glu | Gln | Leu |      |
|     |     |     | 1050|     |     |     |     | 1055|     |     |     |     | 1060|     |     |      |
| CTG | AGA | GAG | GAA | CCG | GAG | AAG | AGA | AGG | CGC | CAG | GAG | CGG | GAG | AGG | CAA | 5751 |
| Leu | Arg | Glu | Glu | Pro | Glu | Lys | Arg | Arg | Arg | Gln | Glu | Arg | Glu | Arg | Gln |      |
| 1065|     |     |     | 1070|     |     |     |     | 1075|     |     |     |     | 1080|     |      |
| TGT | CGG | GAG | GAA | GAG | GAG | CTG | CAG | CAG | GAG | GAA | GAG | CAG | CTG | CTG | AGA | 5799 |
| Cys | Arg | Glu | Glu | Glu | Glu | Leu | Gln | Gln | Glu | Glu | Glu | Gln | Leu | Leu | Arg |      |
|     |     |     |     | 1085|     |     |     |     | 1090|     |     |     |     | 1095|     |      |
| GAG | GAA | CGG | GAG | AAG | AGA | AGG | CGC | CAG | GAG | CTG | GAG | AGG | CAA | TAT | CGG | 5847 |
| Glu | Glu | Arg | Glu | Lys | Arg | Arg | Arg | Gln | Glu | Leu | Glu | Arg | Gln | Tyr | Arg |      |
|     |     |     |     | 1100|     |     |     |     | 1105|     |     |     |     | 1110|     |      |
| GAG | GAG | GAA | GAG | CTT | CAG | CGC | CAG | AAA | AGG | AAA | CAG | CGA | TAC | CGG | GAT | 5895 |
| Glu | Glu | Glu | Glu | Leu | Gln | Arg | Gln | Lys | Arg | Lys | Gln | Arg | Tyr | Arg | Asp |      |
|     |     |     |     | 1115|     |     |     |     | 1120|     |     |     |     | 1125|     |      |
| GAG | GAT | CAG | CGC | AGT | GAT | CTG | AAA | TGG | CAG | TGG | GAA | CCA | GAA | AAA | GAA | 5943 |
| Glu | Asp | Gln | Arg | Ser | Asp | Leu | Lys | Trp | Gln | Trp | Glu | Pro | Glu | Lys | Glu |      |
|     |     |     | 1130|     |     |     |     | 1135|     |     |     |     | 1140|     |     |      |
| AAT | GCA | GTT | CGT | GAT | AAC | AAG | GTT | TAC | TGC | AAA | GGC | AGA | GAG | AAT | GAA | 5991 |
| Asn | Ala | Val | Arg | Asp | Asn | Lys | Val | Tyr | Cys | Lys | Gly | Arg | Glu | Asn | Glu |      |
| 1145|     |     |     | 1150|     |     |     |     | 1155|     |     |     |     | 1160|     |      |
| CAG | TTC | CGG | CAG | TTG | GAA | GAT | TCC | CAG | GTG | CGC | GAC | AGA | CAA | TCC | CAG | 6039 |
| Gln | Phe | Arg | Gln | Leu | Glu | Asp | Ser | Gln | Val | Arg | Asp | Arg | Gln | Ser | Gln |      |
|     |     |     |     | 1165|     |     |     |     | 1170|     |     |     |     | 1175|     |      |
| CAA | GAT | CTG | CAG | CAC | CTG | CTG | GGT | GAA | CAG | CAA | GAG | AGA | GAT | CGT | GAG | 6087 |
| Gln | Asp | Leu | Gln | His | Leu | Leu | Gly | Glu | Gln | Gln | Glu | Arg | Asp | Arg | Glu |      |
|     |     |     |     | 1180|     |     |     |     | 1185|     |     |     |     | 1190|     |      |
| CAA | GAG | AGG | AGG | CGC | TGG | CAG | CAG | GCC | AAC | AGG | CAT | TTC | CCA | GAG | GAA | 6135 |
| Gln | Glu | Arg | Arg | Arg | Trp | Gln | Gln | Ala | Asn | Arg | His | Phe | Pro | Glu | Glu |      |
|     |     |     |     | 1195|     |     |     |     | 1200|     |     |     |     | 1205|     |      |
| GAA | CAG | CTG | GAG | CGA | GAA | GAG | CAA | AAG | GAA | GCC | AAA | AGG | CGC | GAC | AGG | 6183 |
| Glu | Gln | Leu | Glu | Arg | Glu | Glu | Gln | Lys | Glu | Ala | Lys | Arg | Arg | Asp | Arg |      |
|     |     |     | 1210|     |     |     |     | 1215|     |     |     |     | 1220|     |     |      |
| AAG | TCC | CAA | GAG | GAA | AAG | CAG | TTG | CTG | AGA | GAG | GAA | AGA | GAA | GAG | AAG | 6231 |
| Lys | Ser | Gln | Glu | Glu | Lys | Gln | Leu | Leu | Arg | Glu | Glu | Arg | Glu | Glu | Lys |      |
| 1225|     |     |     | 1230|     |     |     |     | 1235|     |     |     |     | 1240|     |      |
| AGA | CGC | CGT | CAA | GAG | ACA | GAC | AGA | AAA | TTC | CGC | GAG | GAG | GAA | CAG | CTG | 6279 |
| Arg | Arg | Arg | Gln | Glu | Thr | Asp | Arg | Lys | Phe | Arg | Glu | Glu | Glu | Gln | Leu |      |
|     |     |     |     | 1245|     |     |     |     | 1250|     |     |     |     | 1255|     |      |
| CTC | CAG | GAA | AGG | GAG | GAA | CAG | CCG | CTG | CTC | CGC | CAA | GAG | CGT | GAC | AGA | 6327 |
| Leu | Gln | Glu | Arg | Glu | Glu | Gln | Pro | Leu | Leu | Arg | Gln | Glu | Arg | Asp | Arg |      |
|     |     |     | 1260|     |     |     |     | 1265|     |     |     |     | 1270|     |     |      |
| AAA | TTC | CGC | GAA | GAG | GAA | CTG | CTC | CAT | CAG | GAA | CAA | GGG | AGA | AAA | TTC | 6375 |
| Lys | Phe | Arg | Glu | Glu | Glu | Leu | Leu | His | Gln | Glu | Gln | Gly | Arg | Lys | Phe |      |
|     |     |     | 1275|     |     |     |     | 1280|     |     |     |     | 1285|     |     |      |
| CTC | GAG | GAG | GAA | CAG | CGG | CTG | CGC | GAG | GAA | CGG | GAG | AGA | AAA | TTC | CTT | 6423 |
| Leu | Glu | Glu | Glu | Gln | Arg | Leu | Arg | Glu | Glu | Arg | Glu | Arg | Lys | Phe | Leu |      |

|  |  |  |  |  |  |  |  |  |  |  |  |  |  |  |  |
|---|---|---|---|---|---|---|---|---|---|---|---|---|---|---|---|
| 1290 | | | | | 1295 | | | | | 1300 | | | | | |

| AAG | GAG | GAA | CAG | CAG | CTG | CGC | CTC | GAG | GAG | CGC | GAG | CAA | CTG | CGT | CAG | 6471 |
|---|---|---|---|---|---|---|---|---|---|---|---|---|---|---|---|---|
| Lys | Glu | Glu | Gln | Gln | Leu | Arg | Leu | Glu | Glu | Arg | Glu | Gln | Leu | Arg | Gln | |
| 1305 | | | | 1310 | | | | | 1315 | | | | | 1320 | | |

| GAC | CGC | GAC | AGA | AAA | TTC | CGC | GAG | GAG | GAA | CAG | CAG | CTG | AGC | CGC | CAA | 6519 |
|---|---|---|---|---|---|---|---|---|---|---|---|---|---|---|---|---|
| Asp | Arg | Asp | Arg | Lys | Phe | Arg | Glu | Glu | Glu | Gln | Gln | Leu | Ser | Arg | Gln | |
| | | | | 1325 | | | | | 1330 | | | | | 1335 | | |

| GAG | CGT | GAC | AGA | AAA | TTC | CGT | GAA | GAG | GAA | CAG | CAG | GTG | CGC | CGC | CAG | 6567 |
|---|---|---|---|---|---|---|---|---|---|---|---|---|---|---|---|---|
| Glu | Arg | Asp | Arg | Lys | Phe | Arg | Glu | Glu | Glu | Gln | Gln | Val | Arg | Arg | Gln | |
| | | | | 1340 | | | | | 1345 | | | | | 1350 | | |

| GAA | CGA | GAG | AGA | AAA | TTC | CTG | GAG | GAG | GAA | CAG | CAG | CTG | CGC | CAG | GAG | 6615 |
|---|---|---|---|---|---|---|---|---|---|---|---|---|---|---|---|---|
| Glu | Arg | Glu | Arg | Lys | Phe | Leu | Glu | Glu | Glu | Gln | Gln | Leu | Arg | Gln | Glu | |
| | | | | 1355 | | | | | 1360 | | | | | 1365 | | |

| CGT | CAC | AGA | AAA | TTC | CGC | GAA | GAG | GAA | CAG | CTG | CTC | CAG | GAA | AGG | GAA | 6663 |
|---|---|---|---|---|---|---|---|---|---|---|---|---|---|---|---|---|
| Arg | His | Arg | Lys | Phe | Arg | Glu | Glu | Glu | Gln | Leu | Leu | Gln | Glu | Arg | Glu | |
| 1370 | | | | | 1375 | | | | | 1380 | | | | | | |

| GAA | CAG | CAG | CTG | CAC | CGC | CAA | GAG | CGT | GAC | AGA | AAA | TTC | CTG | GAG | GAG | 6711 |
|---|---|---|---|---|---|---|---|---|---|---|---|---|---|---|---|---|
| Glu | Gln | Gln | Leu | His | Arg | Gln | Glu | Arg | Asp | Arg | Lys | Phe | Leu | Glu | Glu | |
| 1385 | | | | | 1390 | | | | | 1395 | | | | | 1400 | |

| GAA | CAA | CAG | CTG | CGC | CGC | CAA | GAG | CGT | GAC | AGA | AAA | TTC | CGC | GAA | CAG | 6759 |
|---|---|---|---|---|---|---|---|---|---|---|---|---|---|---|---|---|
| Glu | Gln | Gln | Leu | Arg | Arg | Gln | Glu | Arg | Asp | Arg | Lys | Phe | Arg | Glu | Gln | |
| | | | | 1405 | | | | | 1410 | | | | | 1415 | | |

| GAA | CTG | CGC | AGT | CAG | GAA | CCA | GAG | AGA | AAA | TTC | CTC | GAG | GAG | GAA | CAG | 6807 |
|---|---|---|---|---|---|---|---|---|---|---|---|---|---|---|---|---|
| Glu | Leu | Arg | Ser | Gln | Glu | Pro | Glu | Arg | Lys | Phe | Leu | Glu | Glu | Glu | Gln | |
| | | | | 1420 | | | | | 1425 | | | | | 1430 | | |

| CAG | CTG | CAC | CGC | CAG | CAA | CGG | CAG | AGA | AAA | TTC | CTC | CAG | GAG | GAA | CAG | 6855 |
|---|---|---|---|---|---|---|---|---|---|---|---|---|---|---|---|---|
| Gln | Leu | His | Arg | Gln | Gln | Arg | Gln | Arg | Lys | Phe | Leu | Gln | Glu | Glu | Gln | |
| | | | | 1435 | | | | | 1440 | | | | | 1445 | | |

| CAG | CTG | CGC | CGC | CAG | GAG | CGC | GGG | CAA | CAG | CGG | CGT | CAG | GAC | CGT | GAC | 6903 |
|---|---|---|---|---|---|---|---|---|---|---|---|---|---|---|---|---|
| Gln | Leu | Arg | Arg | Gln | Glu | Arg | Gly | Gln | Gln | Arg | Arg | Gln | Asp | Arg | Asp | |
| | | | | 1450 | | | | | 1455 | | | | | 1460 | | |

| AGA | AAA | TTC | CGC | GAG | GAG | GAA | CAG | CTG | CGC | CAG | GAG | AGG | GAG | GAA | CAG | 6951 |
|---|---|---|---|---|---|---|---|---|---|---|---|---|---|---|---|---|
| Arg | Lys | Phe | Arg | Glu | Glu | Glu | Gln | Leu | Arg | Gln | Glu | Arg | Glu | Glu | Gln | |
| 1465 | | | | | 1470 | | | | | 1475 | | | | | 1480 | |

| CAG | CTG | AGC | CGC | CAA | GAG | CGT | GAC | AGA | AAA | TTC | CGT | TTA | GAG | GAA | CAG | 6999 |
|---|---|---|---|---|---|---|---|---|---|---|---|---|---|---|---|---|
| Gln | Leu | Ser | Arg | Gln | Glu | Arg | Asp | Arg | Lys | Phe | Arg | Leu | Glu | Glu | Gln | |
| | | | | 1485 | | | | | 1490 | | | | | 1495 | | |

| AAA | GTG | CGC | CGC | CAG | GAA | CAA | GAG | AGA | AAA | TTC | ATG | GAG | GAC | GAA | CAG | 7047 |
|---|---|---|---|---|---|---|---|---|---|---|---|---|---|---|---|---|
| Lys | Val | Arg | Arg | Gln | Glu | Gln | Glu | Arg | Lys | Phe | Met | Glu | Asp | Glu | Gln | |
| | | | | 1500 | | | | | 1505 | | | | | 1510 | | |

| CAG | CTG | CGC | CGC | CAG | GAG | GGC | CAA | CAA | CAG | CTG | CGC | CAG | GAG | GAC | AGA | 7095 |
|---|---|---|---|---|---|---|---|---|---|---|---|---|---|---|---|---|
| Gln | Leu | Arg | Arg | Gln | Glu | Gly | Gln | Gln | Gln | Leu | Arg | Gln | Glu | Asp | Arg | |
| | | | | 1515 | | | | | 1520 | | | | | 1525 | | |

| AAA | TTC | CGC | GAA | GAC | GAA | CAG | CTG | CTC | CAG | GAA | AGG | GAA | GAA | CAG | CAG | 7143 |
|---|---|---|---|---|---|---|---|---|---|---|---|---|---|---|---|---|
| Lys | Phe | Arg | Glu | Asp | Glu | Gln | Leu | Leu | Gln | Glu | Arg | Glu | Glu | Gln | Gln | |
| | | | | 1530 | | | | | 1535 | | | | | 1540 | | |

| CTG | CAC | CGC | CAA | GAG | CGT | GAC | AGA | AAA | TTC | CTC | GAG | GAG | GAA | CCG | CAG | 7191 |
|---|---|---|---|---|---|---|---|---|---|---|---|---|---|---|---|---|
| Leu | His | Arg | Gln | Glu | Arg | Asp | Arg | Lys | Phe | Leu | Glu | Glu | Glu | Pro | Gln | |
| 1545 | | | | | 1550 | | | | | 1555 | | | | | 1560 | |

| CTG | CGC | CGC | CAG | GAG | CGC | GAA | CAA | CAG | CTG | CGT | CAC | GAC | CGC | GAC | AGA | 7239 |
|---|---|---|---|---|---|---|---|---|---|---|---|---|---|---|---|---|
| Leu | Arg | Arg | Gln | Glu | Arg | Glu | Gln | Gln | Leu | Arg | His | Asp | Arg | Asp | Arg | |
| | | | | 1565 | | | | | 1570 | | | | | 1575 | | |

| AAA | TTC | CGT | GAA | GAG | GAA | CAG | CTG | CTC | CAG | GAA | GGG | GAG | GAA | CAG | CAG | 7287 |
|---|---|---|---|---|---|---|---|---|---|---|---|---|---|---|---|---|
| Lys | Phe | Arg | Glu | Glu | Glu | Gln | Leu | Leu | Gln | Glu | Gly | Glu | Glu | Gln | Gln | |
| | | | | 1580 | | | | | 1585 | | | | | 1590 | | |

| CTG | CGC | CGC | CAA | GAG | CGT | GAC | AGA | AAA | TTC | CGC | GAA | GAG | GAA | CAG | CAG | 7335 |
|---|---|---|---|---|---|---|---|---|---|---|---|---|---|---|---|---|
| Leu | Arg | Arg | Gln | Glu | Arg | Asp | Arg | Lys | Phe | Arg | Glu | Glu | Glu | Gln | Gln | |
| | | | | 1595 | | | | | 1600 | | | | | 1605 | | |

| CTC | CGC | CGT | CAG | GAA | CGA | GAG | AGA | AAA | TTC | CTC | CAG | GAG | GAA | CAG | CAG | 7383 |
|---|---|---|---|---|---|---|---|---|---|---|---|---|---|---|---|---|
| Leu | Arg | Arg | Gln | Glu | Arg | Glu | Arg | Lys | Phe | Leu | Gln | Glu | Glu | Gln | Gln | |

| | | | | | | | | | | | | | | | | |
|---|---|---|---|---|---|---|---|---|---|---|---|---|---|---|---|---|
| | | | | 1610 | | | | | 1615 | | | | | 1620 | | |
| CTG | CGC | CGC | CAG | GAA | CTG | GAG | AGA | AAA | TTC | CGT | GAG | GAG | GAA | CAG | CTG | 7431 |
| Leu | Arg | Arg | Gln | Glu | Leu | Glu | Arg | Lys | Phe | Arg | Glu | Glu | Glu | Gln | Leu | |
| 1625 | | | | | 1630 | | | | | 1635 | | | | | 1640 | |
| CGC | CAA | GAA | ACG | GAG | CAA | GAG | CAG | CTG | CGC | CGC | CAA | GAA | CGC | TAC | AGA | 7479 |
| Arg | Gln | Glu | Thr | Glu | Gln | Glu | Gln | Leu | Arg | Arg | Gln | Glu | Arg | Tyr | Arg | |
| | | | | 1645 | | | | | 1650 | | | | | 1655 | | |
| AAA | ATC | CTA | GAG | GAA | GAG | CAG | CTC | CGT | CCG | GAA | AGG | GAA | GAA | CAG | CAG | 7527 |
| Lys | Ile | Leu | Glu | Glu | Glu | Gln | Leu | Arg | Pro | Glu | Arg | Glu | Glu | Gln | Gln | |
| | | | 1660 | | | | | 1665 | | | | | 1670 | | | |
| CTG | CGC | CGC | CAG | GAG | CGC | GAC | AGA | AAA | TTC | CGC | GAG | GAG | GAA | CAG | CTC | 7575 |
| Leu | Arg | Arg | Gln | Glu | Arg | Asp | Arg | Lys | Phe | Arg | Glu | Glu | Glu | Gln | Leu | |
| 1675 | | | | | 1680 | | | | | 1685 | | | | | | |
| CGC | CAG | GGA | AGG | GAG | GAA | CAG | CAG | CTG | CGC | AGC | CAA | GAG | TCT | GAC | AGA | 7623 |
| Arg | Gln | Gly | Arg | Glu | Glu | Gln | Gln | Leu | Arg | Ser | Gln | Glu | Ser | Asp | Arg | |
| | | 1690 | | | | | 1695 | | | | | 1700 | | | | |
| AAA | TTC | CGC | GAG | GAG | GAA | CAG | CTA | CGC | CAG | GAG | AGG | GAA | GAA | CAG | CAG | 7671 |
| Lys | Phe | Arg | Glu | Glu | Glu | Gln | Leu | Arg | Gln | Glu | Arg | Glu | Glu | Gln | Gln | |
| 1705 | | | | | 1710 | | | | | 1715 | | | | | 1720 | |
| CTG | CGC | CCC | CAA | CAG | CGT | GAC | GGA | AAG | TAT | CGC | TGG | GAA | GAA | GAG | CAG | 7719 |
| Leu | Arg | Pro | Gln | Gln | Arg | Asp | Gly | Lys | Tyr | Arg | Trp | Glu | Glu | Glu | Gln | |
| | | | | 1725 | | | | | 1730 | | | | | 1735 | | |
| CTC | CAA | CTT | GAG | GAA | CAA | GAG | CAG | AGG | CTG | CGG | CAG | GAG | CGA | GAC | CGG | 7767 |
| Leu | Gln | Leu | Glu | Glu | Gln | Glu | Gln | Arg | Leu | Arg | Gln | Glu | Arg | Asp | Arg | |
| | | | 1740 | | | | | 1745 | | | | | 1750 | | | |
| CAG | TAC | CGG | GCG | GAG | GAG | CAG | TTT | GCC | ACG | CAG | GAG | AAG | AGT | CGT | CGT | 7815 |
| Gln | Tyr | Arg | Ala | Glu | Glu | Gln | Phe | Ala | Thr | Gln | Glu | Lys | Ser | Arg | Arg | |
| | | 1755 | | | | | 1760 | | | | | 1765 | | | | |
| GAG | GAA | CAA | GAA | CTA | TGG | CAA | GAA | GAG | GAG | CAG | AAA | CGT | CGC | CAG | GAA | 7863 |
| Glu | Glu | Gln | Glu | Leu | Trp | Gln | Glu | Glu | Glu | Gln | Lys | Arg | Arg | Gln | Glu | |
| 1770 | | | | | 1775 | | | | | 1780 | | | | | | |
| CGG | GAA | AGG | AAA | TTA | CGG | GAA | GAA | CAC | ATC | CGC | CGC | CAG | CAG | AAG | GAG | 7911 |
| Arg | Glu | Arg | Lys | Leu | Arg | Glu | Glu | His | Ile | Arg | Arg | Gln | Gln | Lys | Glu | |
| 1785 | | | | | 1790 | | | | | 1795 | | | | | 1800 | |
| GAA | CAG | AGG | CAC | CGC | CAA | GTC | GGG | GAG | ATA | CAA | TCC | CAA | GAA | GGG | AAG | 7959 |
| Glu | Gln | Arg | His | Arg | Gln | Val | Gly | Glu | Ile | Gln | Ser | Gln | Glu | Gly | Lys | |
| | | | | 1805 | | | | | 1810 | | | | | 1815 | | |
| GGC | CAT | GGG | CGG | CTT | CTG | GAG | CCC | GGC | ACT | CAT | CAG | TTT | GCC | AGT | GTC | 8007 |
| Gly | His | Gly | Arg | Leu | Leu | Glu | Pro | Gly | Thr | His | Gln | Phe | Ala | Ser | Val | |
| | | | 1820 | | | | | 1825 | | | | | 1830 | | | |
| CCA | GTG | CGC | TCC | AGC | CCT | CTC | TAT | GAG | TAC | ATC | CAA | GAG | CAG | AGA | TCT | 8055 |
| Pro | Val | Arg | Ser | Ser | Pro | Leu | Tyr | Glu | Tyr | Ile | Gln | Glu | Gln | Arg | Ser | |
| | | 1835 | | | | | 1840 | | | | | 1845 | | | | |
| CAA | TAC | CGC | CCT | TAAGTGATGT | | TGCCAATATC | | TTGACACCTG | | CCAAAGCTTC | | | | | | 8107 |
| Gln | Tyr | Arg | Pro | | | | | | | | | | | | | |
| | | | 1850 | | | | | | | | | | | | | |

| | | | | |
|---|---|---|---|---|
| CAGCACGGGA | AAATGAGAAA | CACTGGGTAC | CAAGTGATAA | CTCAGATGTT | TCTGGTTGTG | 8167 |
| GGAAAACTCT | CTGATATTAG | AATGTCTTTT | CTTCCAAAAT | CTTAAACTAC | GCTCATTTTA | 8227 |
| CGCACTTTGT | ACTTCTGCTT | TTTATTCTTC | CTCAAGTAGT | TCTTTACTGC | AAGATGTCTT | 8287 |
| TCTTTTGCTC | TTTGATGCAG | ATGTGGTGTG | CATTTAAAAA | AAATATAAAT | CATTTAATTT | 8347 |
| GTTAAGAAA | TTTTGTTTGA | GGAACATGTT | CATTTATTGC | TTTCAGAAGT | AACAAGAGTA | 8407 |
| ATAGGATGAT | TTGAGATTCT | AAACAATGGG | TCGGTTTGTT | TAATGACTGA | CCCATCTTGT | 8467 |
| GGAAAGTGCA | GATACTTTA | ATGTTCAAGT | TGCTATTTCT | TCTTGAACCT | AAATTGATCA | 8527 |
| TTGCCTCCAA | ACAGCATTTC | ATCCTTTTGT | GGCATAGTTA | GCACAAATTC | CAGGTAACTA | 8587 |
| AATTTTTATA | ACCCTTGAAT | AGTGCAGGGG | GAGTGACCTC | TGCATAAAAA | CTTCCTGTAA | 8647 |

| | | | | | |
|---|---|---|---|---|---|
| AATCAGCCCA | TTACTGGAAG | AAATATCTGT | TAAGAATAGG | TTTAGCTTTG | AAGATTTAGA | 8707 |
| ATTTAAATTA | GATTTTTTTT | AAACTCAACT | CCACTTAAAC | ACATAATCTC | ATGAAGAAAT | 8767 |
| AATGAGGTAT | TTAGAATTTA | AATGAGTTCA | AATTTTAAAA | CTGTGTCTGT | TGTAGTCTAT | 8827 |
| AGTGTTCATT | CTACTTCCCC | AAGTTTTGAT | GAGTTTCAGA | ATATTATGAA | CCTTTGTTAA | 8887 |
| TTTTAGCTTG | TTAGAAGGAA | GCTGCTCAGA | ATCCCATAAA | CATCTGTCTT | ACTCTAGGGC | 8947 |
| CAATAAGAGA | TCACATAGAG | CATGTTGGGG | GTGTAAAAGG | GAAAAATGTG | TGAACATAGG | 9007 |
| GGCAAATTTC | TAGAGGCCCT | TTGACAAGAC | CCATTTGCCC | ACAATCATTT | GAGGCCTATT | 9067 |
| GATAATACCT | TAGATATATT | CTTGTTGAAA | TAATTGGACT | GTGAAAAATT | AATAATAAAT | 9127 |
| GTTTGGCAAG | TAACTACTTT | TGTCTGTTTT | AACTCTGCGT | CAATCATAAC | AAGATCTCAT | 9187 |
| TGTCTGGAAA | CTAACACAAG | TTCCCAATCA | CATAAGGGCA | TTTTGTTACT | TATCTATGTC | 9247 |
| CAAATACGAA | AAAAGAGGGG | AGAGAATTCT | TTGTTTTTCC | CCAACCTTTT | TTTTTTTTT | 9307 |
| TTTTTTTTTT | TTTTGCAGTT | AGGCTGAACT | CTATTTCCAT | CCCCACACTG | AGATTGCCTT | 9367 |
| CCAGAGTGTT | TTTGTTCTTG | ACCCACAGCT | TTCTATGCCA | TTCTTGCAGC | GACTCACTGG | 9427 |
| TCATGACAAA | TACTGGTGCT | CCCAATATTT | GTTAATATTT | CCTTTAGAGA | ATGCAGCAGC | 9487 |
| TTCTTCGTCT | CTGATGTCTG | ATGAGCCAAT | GATAGAAAAT | GGCCTGAAAC | TTCAGATCCT | 9547 |
| CGAG | | | | | | 9551 |

( 2 ) INFORMATION FOR SEQ ID NO:94:

( i ) SEQUENCE CHARACTERISTICS:
        ( A ) LENGTH: 1898 amino acids
        ( B ) TYPE: amino acid
        ( D ) TOPOLOGY: linear ( i i ) MOLECULE TYPE: protein ( x i ) SEQUENCE DESCRIPTION: SEQ ID NO:94:

```
Met Ser Pro Leu Leu Arg Ser Ile Cys Asp Ile Thr Glu Ile Phe Asn
 1               5                  10                  15

Gln Tyr Val Ser His Asp Cys Asp Gly Ala Ala Leu Thr Lys Lys Asp
             20                  25                  30

Leu Lys Asn Leu Leu Glu Arg Glu Phe Gly Ala Val Leu Arg Arg Pro
         35                  40                  45

His Asp Pro Lys Thr Val Asp Leu Ile Leu Glu Leu Asp Arg Asp
     50                  55                  60

Ser Asn Gly Arg Val Asp Phe Asn Glu Phe Leu Leu Phe Ile Phe Lys
65                   70                  75                  80

Val Ala Gln Ala Cys Tyr Tyr Ala Leu Gly Gln Ala Thr Gly Leu Asp
                 85                  90                  95

Glu Glu Lys Arg Ala Arg Cys Asp Gly Lys Glu Ser Leu Leu Gln Asp
                100                 105                 110

Arg Arg Thr Glu Glu Asp Gln Arg Arg Phe Glu Pro Arg Asp Arg Gln
            115                 120                 125

Leu Glu Glu Glu Pro Gly Gln Arg Arg Arg Gln Lys Arg Gln Glu Gln
        130                 135                 140

Glu Arg Glu Leu Ala Glu Gly Glu Glu Gln Ser Glu Lys Gln Glu Arg
145                 150                 155                 160

Leu Glu Gln Arg Asp Arg Gln Arg Arg Asp Glu Glu Leu Trp Arg Gln
                165                 170                 175

Arg Gln Glu Trp Gln Glu Arg Glu Glu Arg Arg Ala Glu Glu Glu Gln
            180                 185                 190
```

| | | | | | | | | | | | | | | |
|---|---|---|---|---|---|---|---|---|---|---|---|---|---|---|
| Leu | Gln | Ser<br>195 | Cys | Lys | Gly | His | Glu<br>200 | Thr | Glu | Glu | Phe<br>205 | Pro | Asp | Glu | Glu |
| Gln | Leu<br>210 | Arg | Arg | Arg | Glu | Leu<br>215 | Leu | Glu | Leu | Arg | Arg<br>220 | Lys | Gly | Arg | Glu |
| Glu<br>225 | Lys | Gln | Gln | Gln | Arg<br>230 | Arg | Glu | Arg | Gln | Asp<br>235 | Arg | Val | Phe | Gln | Glu<br>240 |
| Glu | Glu | Glu | Lys | Glu<br>245 | Trp | Arg | Lys | Arg | Glu<br>250 | Thr | Val | Leu | Arg | Lys<br>255 | Glu |
| Glu | Glu | Lys | Leu<br>260 | Gln | Glu | Glu | Glu | Pro<br>265 | Gln | Arg | Gln | Arg | Glu<br>270 | Leu | Gln |
| Glu | Glu | Glu<br>275 | Glu | Gln | Leu | Arg | Lys<br>280 | Leu | Glu | Arg | Gln | Glu<br>285 | Leu | Arg | Arg |
| Glu | Arg<br>290 | Gln | Glu | Glu | Glu | Gln<br>295 | Gln | Gln | Gln | Arg | Leu<br>300 | Arg | Arg | Glu | Gln |
| Gln<br>305 | Leu | Arg | Arg | Lys | Gln<br>310 | Glu | Glu | Glu | Arg | Arg<br>315 | Glu | Gln | Gln | Glu | Glu<br>320 |
| Arg | Arg | Glu | Gln | Gln<br>325 | Glu | Arg | Arg | Glu | Gln<br>330 | Gln | Glu | Glu | Arg | Arg<br>335 | Glu |
| Gln | Gln | Leu | Arg<br>340 | Arg | Glu | Gln | Glu | Glu<br>345 | Arg | Arg | Glu | Gln | Gln<br>350 | Leu | Arg |
| Arg | Glu | Gln<br>355 | Glu | Glu | Glu | Arg | Arg<br>360 | Glu | Gln | Gln | Leu | Arg<br>365 | Arg | Glu | Gln |
| Glu | Glu | Glu<br>370 | Arg | Arg | Glu | Gln<br>375 | Leu | Arg | Arg | Glu | Gln<br>380 | Gln | Glu | Glu | Glu |
| Arg<br>385 | Arg | Glu | Gln | Gln | Leu<br>390 | Arg | Arg | Glu | Gln | Gln<br>395 | Leu | Arg | Arg | Glu | Gln<br>400 |
| Gln | Leu | Arg | Arg | Glu<br>405 | Gln | Gln | Leu | Arg | Arg<br>410 | Glu | Gln | Gln | Leu | Arg<br>415 | Arg |
| Glu | Gln | Gln | Leu<br>420 | Arg | Arg | Glu | Gln | Gln<br>425 | Leu | Arg | Arg | Glu | Gln<br>430 | Gln | Leu |
| Arg | Arg | Glu<br>435 | Gln | Gln | Leu | Arg | Arg<br>440 | Glu | Gln | Gln | Leu | Arg<br>445 | Arg | Glu | Gln |
| Glu | Glu | Glu<br>450 | Arg | His | Glu | Gln<br>455 | Lys | His | Glu | Gln | Glu<br>460 | Arg | Arg | Glu | Gln |
| Arg<br>465 | Leu | Lys | Arg | Glu | Gln<br>470 | Glu | Glu | Arg | Arg | Asp<br>475 | Trp | Leu | Lys | Arg | Glu<br>480 |
| Glu | Glu | Thr | Glu | Arg<br>485 | His | Glu | Gln | Glu | Arg<br>490 | Arg | Lys | Gln | Gln | Leu<br>495 | Lys |
| Arg | Asp | Gln | Glu<br>500 | Glu | Glu | Arg | Arg | Glu<br>505 | Arg | Trp | Leu | Lys | Leu<br>510 | Glu | Glu |
| Glu | Glu | Arg<br>515 | Arg | Glu | Gln | Gln | Glu<br>520 | Arg | Arg | Glu | Gln | Gln<br>525 | Leu | Arg | Arg |
| Glu | Gln<br>530 | Glu | Glu | Arg | Arg | Glu<br>535 | Gln | Arg | Leu | Lys | Arg<br>540 | Gln | Glu | Glu | Glu |
| Glu<br>545 | Arg | Leu | Gln | Gln | Arg<br>550 | Leu | Arg | Ser | Glu | Gln<br>555 | Gln | Leu | Arg | Arg | Glu<br>560 |
| Gln | Glu | Glu | Arg | Leu<br>565 | Glu | Gln | Leu | Leu | Lys<br>570 | Arg | Glu | Glu | Glu | Lys<br>575 | Arg |
| Leu | Glu | Gln | Glu<br>580 | Arg | Arg | Glu | Gln | Arg<br>585 | Leu | Lys | Arg | Glu | Gln<br>590 | Glu | Glu |
| Arg | Arg | Asp<br>595 | Gln | Leu | Leu | Lys | Arg<br>600 | Glu | Glu | Glu | Arg | Arg<br>605 | Gln | Gln | Arg |
| Leu | Lys<br>610 | Arg | Glu | Gln | Glu | Glu<br>615 | Arg | Leu | Glu | Gln | Arg<br>620 | Leu | Lys | Arg | Glu |

```
Glu  Val  Glu  Arg  Leu  Gln  Glu  Glu  Arg  Arg  Asp  Glu  Arg  Leu  Lys
625            630                 635                      640

Arg  Glu  Glu  Pro  Glu  Glu  Arg  Arg  His  Glu  Leu  Leu  Lys  Ser  Glu
               645                 650                 655

Glu  Gln  Glu  Glu  Arg  Arg  His  Glu  Gln  Leu  Arg  Arg  Glu  Gln  Glu
               660                 665                      670

Arg  Arg  Glu  Gln  Arg  Leu  Lys  Arg  Glu  Glu  Glu  Glu  Arg  Leu  Glu
          675                 680                      685

Gln  Arg  Leu  Lys  Arg  Glu  His  Glu  Glu  Glu  Arg  Arg  Glu  Gln  Glu  Leu
     690                 695                      700

Ala  Glu  Glu  Glu  Gln  Glu  Gln  Ala  Arg  Glu  Arg  Ile  Lys  Ser  Arg  Ile
705                 710                 715                           720

Pro  Lys  Trp  Gln  Trp  Gln  Leu  Glu  Ser  Glu  Ala  Asp  Ala  Arg  Gln  Ser
                    725                 730                           735

Lys  Val  Leu  Leu  Glu  Ala  Pro  Gln  Ala  Gly  Arg  Ala  Glu  Ala  Pro  Gln
               740                 745                      750

Glu  Gln  Glu  Glu  Lys  Arg  Arg  Arg  Glu  Ser  Glu  Leu  Gln  Trp  Gln  Glu
               755                 760                      765

Glu  Glu  Arg  Ala  His  Arg  Gln  Gln  Gln  Glu  Glu  Gln  Arg  Arg  Asp
770                 775                      780

Phe  Thr  Trp  Gln  Trp  Gln  Ala  Glu  Glu  Lys  Ser  Glu  Arg  Gly  Arg  Gln
785                 790                 795                           800

Arg  Leu  Ser  Ala  Arg  Pro  Pro  Leu  Arg  Glu  Gln  Arg  Glu  Arg  Gln  Leu
               805                 810                      815

Arg  Ala  Glu  Glu  Arg  Gln  Gln  Arg  Glu  Gln  Arg  Phe  Leu  Pro  Glu  Glu
               820                 825                      830

Glu  Glu  Lys  Glu  Gln  Arg  Gly  Arg  Gln  Arg  Arg  Glu  Arg  Glu  Lys  Glu
          835                 840                      845

Leu  Gln  Phe  Leu  Glu  Glu  Glu  Gln  Leu  Gln  Arg  Arg  Glu  Arg  Ala
          850                 855                      860

Gln  Gln  Leu  Gln  Glu  Glu  Glu  Asp  Gly  Leu  Gln  Glu  Asp  Gln  Glu  Arg
865                 870                      875                      880

Arg  Arg  Gln  Glu  Gln  Arg  Arg  Asp  Gln  Lys  Trp  Arg  Trp  Gln  Leu  Glu
               885                      890                      895

Glu  Glu  Arg  Lys  Arg  Arg  Arg  His  Thr  Leu  Tyr  Ala  Lys  Pro  Ala  Leu
               900                 905                      910

Gln  Glu  Gln  Leu  Arg  Lys  Glu  Gln  Gln  Leu  Leu  Gln  Glu  Glu  Glu
               915                 920                      925

Glu  Leu  Gln  Arg  Glu  Glu  Arg  Glu  Lys  Arg  Arg  Arg  Gln  Glu  Gln  Glu
     930                 935                      940

Arg  Gln  Tyr  Arg  Glu  Glu  Glu  Gln  Leu  Gln  Gln  Glu  Glu  Glu  Gln  Leu
945                 950                      955                      960

Leu  Arg  Glu  Glu  Arg  Glu  Lys  Arg  Arg  Arg  Gln  Glu  Arg  Glu  Arg  Gln
               965                 970                      975

Tyr  Arg  Lys  Asp  Lys  Lys  Leu  Gln  Gln  Lys  Glu  Glu  Gln  Leu  Leu  Gly
               980                 985                      990

Glu  Glu  Pro  Glu  Lys  Arg  Arg  Arg  Gln  Glu  Arg  Glu  Lys  Lys  Tyr  Arg
          995                 1000                     1005

Glu  Glu  Glu  Glu  Leu  Gln  Gln  Glu  Glu  Glu  Gln  Leu  Leu  Arg  Glu  Glu
          1010                1015                     1020

Arg  Glu  Lys  Arg  Arg  Arg  Gln  Glu  Trp  Glu  Arg  Gln  Tyr  Arg  Lys  Lys
1025                1030                     1035                     1040

Asp  Glu  Leu  Gln  Gln  Glu  Glu  Glu  Gln  Leu  Leu  Arg  Glu  Glu  Arg  Glu
```

|  |  |  |
|---|---|---|
| 1045 | 1050 | 1055 |

Lys Arg Arg Leu Gln Glu Arg Glu Arg Gln Tyr Arg Glu Glu Glu
              1060                1065              1070

Leu Gln Gln Glu Glu Glu Gln Leu Leu Gly Glu Glu Arg Glu Thr Arg
              1075                1080              1085

Arg Arg Gln Glu Leu Glu Arg Gln Tyr Arg Lys Glu Glu Glu Leu Gln
              1090                1095              1100

Gln Glu Glu Glu Gln Leu Leu Arg Glu Glu Pro Glu Lys Arg Arg Arg
1105              1110                1115              1120

Gln Glu Arg Glu Arg Gln Cys Arg Glu Glu Glu Leu Gln Gln Glu
              1125                1130              1135

Glu Glu Gln Leu Leu Arg Glu Glu Arg Glu Lys Arg Arg Arg Gln Glu
              1140                1145              1150

Leu Glu Arg Gln Tyr Arg Glu Glu Glu Leu Gln Arg Gln Lys Arg
              1155                1160              1165

Lys Gln Arg Tyr Arg Asp Glu Asp Gln Arg Ser Asp Leu Lys Trp Gln
              1170                1175              1180

Trp Glu Pro Glu Lys Glu Asn Ala Val Arg Asp Asn Lys Val Tyr Cys
1185              1190                1195              1200

Lys Gly Arg Glu Asn Glu Gln Phe Arg Gln Leu Glu Asp Ser Gln Val
              1205                1210              1215

Arg Asp Arg Gln Ser Gln Gln Asp Leu Gln His Leu Leu Gly Glu Gln
              1220                1225              1230

Gln Glu Arg Asp Arg Glu Gln Glu Arg Arg Arg Trp Gln Gln Ala Asn
              1235                1240              1245

Arg His Phe Pro Glu Glu Glu Gln Leu Glu Arg Glu Glu Gln Lys Glu
              1250                1255              1260

Ala Lys Arg Arg Asp Arg Lys Ser Gln Glu Glu Lys Gln Leu Leu Arg
1265              1270                1275              1280

Glu Glu Arg Glu Glu Lys Arg Arg Arg Gln Glu Thr Asp Arg Lys Phe
              1285                1290              1295

Arg Glu Glu Glu Gln Leu Leu Gln Glu Arg Glu Glu Gln Pro Leu Leu
              1300                1305              1310

Arg Gln Glu Arg Asp Arg Lys Phe Arg Glu Glu Glu Leu Leu His Gln
              1315                1320              1325

Glu Gln Gly Arg Lys Phe Leu Glu Glu Glu Gln Arg Leu Arg Glu Glu
              1330                1335              1340

Arg Glu Arg Lys Phe Leu Lys Glu Glu Gln Leu Arg Leu Glu Glu
1345              1350                1355              1360

Arg Glu Gln Leu Arg Gln Asp Arg Asp Arg Lys Phe Arg Glu Glu Glu
              1365                1370              1375

Gln Gln Leu Ser Arg Gln Glu Arg Asp Arg Lys Phe Arg Glu Glu Glu
              1380                1385              1390

Gln Gln Val Arg Arg Gln Glu Arg Glu Arg Lys Phe Leu Glu Glu Glu
              1395                1400              1405

Gln Gln Leu Arg Gln Glu Arg His Arg Lys Phe Arg Glu Glu Glu Gln
              1410                1415              1420

Leu Leu Gln Glu Arg Glu Glu Gln Gln Leu His Arg Gln Glu Arg Asp
1425              1430                1435              1440

Arg Lys Phe Leu Glu Glu Glu Gln Gln Leu Arg Arg Gln Glu Arg Asp
              1445                1450              1455

Arg Lys Phe Arg Glu Glu Glu Leu Arg Ser Gln Glu Pro Glu Arg Lys
              1460                1465              1470

```
Phe  Leu  Glu  Glu  Glu  Gln  Gln  Leu  His  Arg  Gln  Gln  Arg  Gln  Arg  Lys
          1475                     1480                    1485

Phe  Leu  Gln  Glu  Glu  Gln  Gln  Leu  Arg  Arg  Gln  Glu  Arg  Gly  Gln  Gln
          1490                     1495                    1500

Arg  Arg  Gln  Asp  Arg  Asp  Arg  Lys  Phe  Arg  Glu  Glu  Gln  Leu  Arg
1505                1510                    1515                         1520

Gln  Glu  Arg  Glu  Glu  Gln  Gln  Leu  Ser  Arg  Gln  Glu  Arg  Asp  Arg  Lys
          1525                     1530                    1535

Phe  Arg  Leu  Glu  Glu  Gln  Lys  Val  Arg  Arg  Gln  Glu  Gln  Glu  Arg  Lys
          1540                     1545                    1550

Phe  Met  Glu  Asp  Glu  Gln  Gln  Leu  Arg  Arg  Gln  Glu  Gly  Gln  Gln  Gln
          1555                     1560                    1565

Leu  Arg  Gln  Glu  Asp  Arg  Lys  Phe  Arg  Glu  Asp  Glu  Gln  Leu  Leu  Gln
          1570                     1575                    1580

Glu  Arg  Glu  Glu  Gln  Gln  Leu  His  Arg  Gln  Glu  Arg  Asp  Arg  Lys  Phe
1585                1590                    1595                         1600

Leu  Glu  Glu  Glu  Pro  Gln  Leu  Arg  Arg  Gln  Glu  Arg  Glu  Gln  Gln  Leu
                    1605                    1610                    1615

Arg  His  Asp  Arg  Asp  Arg  Lys  Phe  Arg  Glu  Glu  Glu  Gln  Leu  Leu  Gln
          1620                     1625                    1630

Glu  Gly  Glu  Glu  Gln  Gln  Leu  Arg  Arg  Gln  Glu  Arg  Asp  Arg  Lys  Phe
          1635                     1640                    1645

Arg  Glu  Glu  Glu  Gln  Gln  Leu  Arg  Arg  Gln  Glu  Arg  Glu  Arg  Lys  Phe
          1650                     1655                    1660

Leu  Gln  Glu  Glu  Gln  Gln  Leu  Arg  Arg  Gln  Glu  Leu  Glu  Arg  Lys  Phe
1665                1670                    1675                         1680

Arg  Glu  Glu  Glu  Gln  Leu  Arg  Gln  Glu  Thr  Glu  Gln  Glu  Gln  Leu  Arg
          1685                     1690                    1695

Arg  Gln  Glu  Arg  Tyr  Arg  Lys  Ile  Leu  Glu  Glu  Glu  Gln  Leu  Arg  Pro
          1700                     1705                    1710

Glu  Arg  Glu  Glu  Gln  Gln  Leu  Arg  Arg  Gln  Glu  Arg  Asp  Arg  Lys  Phe
          1715                     1720                    1725

Arg  Glu  Glu  Glu  Gln  Leu  Arg  Gln  Gly  Arg  Glu  Glu  Gln  Gln  Leu  Arg
          1730                     1735                    1740

Ser  Gln  Glu  Ser  Asp  Arg  Lys  Phe  Arg  Glu  Glu  Glu  Gln  Leu  Arg  Gln
1745                1750                    1755                         1760

Glu  Arg  Glu  Glu  Gln  Gln  Leu  Arg  Pro  Gln  Gln  Arg  Asp  Gly  Lys  Tyr
                    1765                    1770                    1775

Arg  Trp  Glu  Glu  Glu  Gln  Leu  Gln  Leu  Glu  Glu  Gln  Glu  Gln  Arg  Leu
               1780                    1785                    1790

Arg  Gln  Glu  Arg  Asp  Arg  Gln  Tyr  Arg  Ala  Glu  Glu  Gln  Phe  Ala  Thr
          1795                     1800                    1805

Gln  Glu  Lys  Ser  Arg  Arg  Glu  Glu  Gln  Glu  Leu  Trp  Gln  Glu  Glu  Glu
          1810                     1815                    1820

Gln  Lys  Arg  Arg  Gln  Glu  Arg  Glu  Arg  Lys  Leu  Arg  Glu  Glu  His  Ile
1825                1830                    1835                         1840

Arg  Arg  Gln  Gln  Lys  Glu  Glu  Gln  Arg  His  Arg  Gln  Val  Gly  Glu  Ile
                    1845                    1850                    1855

Gln  Ser  Gln  Glu  Gly  Lys  Gly  His  Gly  Arg  Leu  Leu  Glu  Pro  Gly  Thr
                    1860                    1865                    1870

His  Gln  Phe  Ala  Ser  Val  Pro  Val  Arg  Ser  Ser  Pro  Leu  Tyr  Glu  Tyr
          1875                     1880                    1885

Ile  Gln  Glu  Gln  Arg  Ser  Gln  Tyr  Arg  Pro
          1890                     1895
```

( 2 ) INFORMATION FOR SEQ ID NO:95:

( i ) SEQUENCE CHARACTERISTICS:
        ( A ) LENGTH: 45 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:95:

```
Ser Pro Leu Leu Arg Ser Ile Cys Asp Ile Thr Glu Ile Phe Asn Gln
 1               5                  10                  15

Tyr Val Ser His Asp Cys Asp Gly Ala Ala Leu Thr Lys Lys Asp Leu
                20                  25                  30

Lys Asn Leu Leu Glu Arg Glu Phe Gly Ala Val Leu Arg
                35                  40                  45
```

( 2 ) INFORMATION FOR SEQ ID NO:96:

( i ) SEQUENCE CHARACTERISTICS:
        ( A ) LENGTH: 45 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:96:

```
Ser Thr Leu Leu Val Phe Ile Phe Ala Ile Ile Asn Leu Phe Asn Glu
 1               5                  10                  15

Tyr Ser Lys Lys Asp Lys Asn Thr Asp Thr Leu Ser Lys Lys Glu Leu
                20                  25                  30

Lys Glu Leu Leu Glu Lys Glu Phe Arg Gln Ile Leu Lys
                35                  40                  45
```

( 2 ) INFORMATION FOR SEQ ID NO:97:

( i ) SEQUENCE CHARACTERISTICS:
        ( A ) LENGTH: 45 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:97:

```
Ser Glu Leu Glu Lys Ala Met Val Ala Leu Ile Asp Val Phe His Gln
 1               5                  10                  15

Tyr Ser Gly Arg Glu Gly Asp Lys His Lys Leu Lys Lys Ser Glu Leu
```

```
               20                    25                         30

Lys  Glu  Leu  Ile  Asn  Asn  Glu  Leu  Ser  His  Phe  Leu  Glu
                  35                  40                       45
```

(2) INFORMATION FOR SEQ ID NO:98:

(i) SEQUENCE CHARACTERISTICS:
        (A) LENGTH: 45 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:98:

```
   Thr  Glu  Leu  Glu  Thr  Ala  Met  Gly  Met  Ile  Ile  Asp  Val  Phe  Ser  Arg
   1                   5                        10                       15

Tyr  Ser  Gly  Ser  Glu  Gly  Ser  Thr  Gln  Thr  Leu  Thr  Lys  Gly  Glu  Leu
                  20                  25                       30

Lys  Val  Leu  Met  Glu  Lys  Glu  Leu  Pro  Gly  Phe  Leu  Gln
                  35                  40                       45
```

(2) INFORMATION FOR SEQ ID NO:99:

(i) SEQUENCE CHARACTERISTICS:
        (A) LENGTH: 42 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:99:

```
   Ser  Gln  Met  Glu  His  Ala  Met  Glu  Thr  Met  Met  Phe  Thr  Phe  His  Lys
   1                   5                        10                       15

Phe  Ala  Gly  Asp  Lys  Gly  Tyr  Leu  Thr  Lys  Arg  Asp  Leu  Arg  Val  Leu
                  20                  25                       30

Met  Glu  Lys  Glu  Phe  Pro  Gly  Phe  Leu  Glu
                  35                  40
```

(2) INFORMATION FOR SEQ ID NO:100:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:100:

```
    Cys Pro Leu Asp Gln Ala Ile Gly Leu Leu Val Ala Ile Phe His Lys
    1               5               10                  15

Tyr Ser Gly Arg Glu Gly Asp Lys His Thr Leu Ser Lys Lys Glu Leu
                20              25                  30

Lys Glu Leu Ile Gln Lys Glu Leu Thr Ser Ile Gly
                35              40
```

( 2 ) INFORMATION FOR SEQ ID NO:101:

( i ) SEQUENCE CHARACTERISTICS:
      ( A ) LENGTH: 45 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:101:

```
    Thr Glu Leu Glu Lys Ala Leu Asn Ser Ile Ile Asp Val Tyr His Lys
    1               5               10                  15

Tyr Ser Leu Ile Lys Gly Asn Phe His Ala Val Tyr Arg Asp Asp Leu
                20              25                  30

Lys Lys Leu Leu Glu Thr Glu Cys Pro Gln Tyr Ile Arg
                35              40                  45
```

( 2 ) INFORMATION FOR SEQ ID NO:102:

( i ) SEQUENCE CHARACTERISTICS:
      ( A ) LENGTH: 45 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:102:

```
    Arg Pro His Asp Pro Lys Thr Val Asp Leu Ile Leu Glu Leu Leu Asp
    1               5               10                  15

Arg Asp Ser Asn Gly Arg Val Asp Phe Asn Glu Phe Leu Leu Phe Ile
                20              25                  30

Phe Phe Val Ala Gln Ala Cys Tyr Tyr Ala Leu Gly Gln
                35              40                  45
```

( 2 ) INFORMATION FOR SEQ ID NO:103:

( i ) SEQUENCE CHARACTERISTICS:
      ( A ) LENGTH: 45 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO (v) FRAGMENT TYPE: internal (xi) SEQUENCE DESCRIPTION: SEQ ID NO:103:

```
Asn Pro Asp Asp Pro Asp Met Val Asp Val Phe Met Asp His Leu Asp
 1               5                  10                 15

Ile Asp His Asn Lys Lys Ile Asp Phe Thr Glu Phe Leu Leu Met Val
                 20                  25                 30

Phe Lys Leu Ala Gln Ala Tyr Tyr Glu Ser Thr Arg Lys
             35              40              45
```

(2) INFORMATION FOR SEQ ID NO:104:

(i) SEQUENCE CHARACTERISTICS:
　　　　(A) LENGTH: 45 amino acids
　　　　(B) TYPE: amino acid
　　　　(C) STRANDEDNESS: single
　　　　(D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:104:

```
Glu Ile Lys Glu Gln Glu Val Val Asp Lys Val Met Glu Thr Leu Asp
 1               5                  10                 15

Asn Asp Gly Asp Gly Glu Cys Asp Phe Gln Glu Phe Met Ala Phe Val
                 20                  25                 30

Ala Met Val Thr Thr Ala Cys His Glu Phe Phe Glu His
             35              40              45
```

(2) INFORMATION FOR SEQ ID NO:105:

(i) SEQUENCE CHARACTERISTICS:
　　　　(A) LENGTH: 45 amino acids
　　　　(B) TYPE: amino acid
　　　　(C) STRANDEDNESS: single
　　　　(D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:105:

```
Ser Gly Lys Asp Lys Asp Ala Val Asp Lys Leu Leu Lys Asp Leu Asp
 1               5                  10                 15

Ala Asn Gly Asp Ala Gln Val Asp Phe Ser Glu Phe Ile Val Phe Val
                 20                  25                 30

Ala Ala Ile Thr Ser Ala Cys His Lys Tyr Phe Glu Lys
             35              40              45
```

(2) INFORMATION FOR SEQ ID NO:106:

(i) SEQUENCE CHARACTERISTICS:
　　　　(A) LENGTH: 45 amino acids
　　　　(B) TYPE: amino acid
　　　　(C) STRANDEDNESS: single
　　　　(D) TOPOLOGY: linear (ii) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:106:

| Asn | Gln | Lys | Asp | Pro | Leu | Ala | Val | Asp | Lys | Ile | Met | Lys | Asp | Leu | Asp |
|---|---|---|---|---|---|---|---|---|---|---|---|---|---|---|---|
| 1 | | | | 5 | | | | | 10 | | | | | 15 | |
| Gln | Cys | Arg | Asp | Gly | Lys | Val | Gly | Phe | Gln | Ser | Phe | Phe | Ser | Leu | Ile |
| | | | 20 | | | | | 25 | | | | | 30 | | |
| Ala | Gly | Leu | Thr | Ile | Ala | Cys | Asn | Asp | Tyr | Phe | Val | Val | | | |
| | | 35 | | | | | 40 | | | | | 45 | | | |

( 2 ) INFORMATION FOR SEQ ID NO:107:

( i ) SEQUENCE CHARACTERISTICS:
        ( A ) LENGTH: 45 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:107:

| Lys | Leu | Gln | Asp | Ala | Glu | Ile | Ala | Arg | Leu | Met | Ile | Phe | Asp | Leu | Asp |
|---|---|---|---|---|---|---|---|---|---|---|---|---|---|---|---|
| 1 | | | | 5 | | | | | 10 | | | | | 15 | |
| Arg | Asn | Lys | Asp | Gly | Glu | Val | Asn | Phe | Gln | Glu | Tyr | Val | Thr | Phe | Leu |
| | | | 20 | | | | | 25 | | | | | 30 | | |
| Gly | Ala | Leu | Ala | Leu | Ile | Tyr | Asn | Glu | Ala | Leu | Lys | Gly | | | |
| | | 35 | | | | | 40 | | | | | 45 | | | |

( 2 ) INFORMATION FOR SEQ ID NO:108:

( i ) SEQUENCE CHARACTERISTICS:
        ( A ) LENGTH: 41 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:108:

| Lys | Lys | Gly | Ala | Asp | Val | Trp | Phe | Lys | Glu | Leu | Asp | Ile | Asn | Thr | Asp |
|---|---|---|---|---|---|---|---|---|---|---|---|---|---|---|---|
| 1 | | | | 5 | | | | | 10 | | | | | 15 | |
| Gly | Ala | Val | Asn | Phe | Gln | Glu | Phe | Leu | Ile | Leu | Val | Ile | Lys | Met | Gly |
| | | | 20 | | | | | 25 | | | | | 30 | | |
| Val | Ala | Ala | His | Lys | Lys | Ser | His | Glu | | | | | | | |
| | | 35 | | | | | 40 | | | | | | | | |

( 2 ) INFORMATION FOR SEQ ID NO:109:

( i ) SEQUENCE CHARACTERISTICS:
        ( A ) LENGTH: 2620 base pairs
        ( B ) TYPE: nucleic acid
        ( C ) STRANDEDNESS: single ( D ) TOPOLOGY: linear ( i i ) MOLECULE TYPE: cDNA ( i i i ) HYPOTHETICAL: NO ( i v ) ANTI-SENSE: NO ( i x ) FEATURE:
    ( A ) NAME/KEY: CDS
    ( B ) LOCATION: 42..2120

( x i ) SEQUENCE DESCRIPTION: SEQ ID NO:109:

```
CCTTTAGAGG AGCCTGAGAA GAGGCAGAGG AAGGGCGAAA C ATG GCT GCT CTA                53
                                              Met Ala Ala Leu
                                                1

GGA GTC CAG AGT ATC AAC TGG CAG AAG GCC TTC AAC CGA CAA GCG CAT            101
Gly Val Gln Ser Ile Asn Trp Gln Lys Ala Phe Asn Arg Gln Ala His
  5              10              15                  20

CAC ACA GAC AAG TTC TCC AGC CAG GAG CTC ATC TTG CGG AGA GGC CAA            149
His Thr Asp Lys Phe Ser Ser Gln Glu Leu Ile Leu Arg Arg Gly Gln
                 25              30                  35

AAC TTC CAG GTC TTA ATG ATC ATG AAC AAA GGC CTT GGC TCT AAC GAA            197
Asn Phe Gln Val Leu Met Ile Met Asn Lys Gly Leu Gly Ser Asn Glu
             40              45                  50

AGA CTG GAG TTC ATT GAC ACC ACA GGG CCT TAC CCC TCA GAG TCG GCC            245
Arg Leu Glu Phe Ile Asp Thr Thr Gly Pro Tyr Pro Ser Glu Ser Ala
         55              60                  65

ATG ACG AAG GCT GTG TTT CCA CTC TCC AAT GGC AGT AGT GGT GGC TGG            293
Met Thr Lys Ala Val Phe Pro Leu Ser Asn Gly Ser Ser Gly Gly Trp
     70              75                  80

AGT GCG GTG CTT CAG GCC AGC AAT GGC AAT ACT CTG ACT ATC AGC ATC            341
Ser Ala Val Leu Gln Ala Ser Asn Gly Asn Thr Leu Thr Ile Ser Ile
 85              90                  95                     100

TCC AGT CCT GCC AGC GCA CCC ATA GGA CGG TAC ACA ATG GCC CTC CAG            389
Ser Ser Pro Ala Ser Ala Pro Ile Gly Arg Tyr Thr Met Ala Leu Gln
             105                 110                 115

ATC TTC TCC CAG GGC GGC ATC TCC TCT GTG AAA CTT GGG ACG TTC ATA            437
Ile Phe Ser Gln Gly Gly Ile Ser Ser Val Lys Leu Gly Thr Phe Ile
             120                 125                 130

CTG CTT TTT AAC CCC TGG CTG AAT GTG GAT AGC GTC TTT ATG GGT AAC            485
Leu Leu Phe Asn Pro Trp Leu Asn Val Asp Ser Val Phe Met Gly Asn
             135                 140                 145

CAT GCT GAG AGA GAA GAG TAT GTT CAG GAA GAT GCC GGC ATC ATC TTT            533
His Ala Glu Arg Glu Glu Tyr Val Gln Glu Asp Ala Gly Ile Ile Phe
     150                 155                 160

GTG GGA AGC ACA AAC CGA ATT GGC ATG ATT GGC TGG AAC TTT GGA CAG            581
Val Gly Ser Thr Asn Arg Ile Gly Met Ile Gly Trp Asn Phe Gly Gln
 165                 170                 175                 180

TTT GAA GAA GAC ATT CTC AGC ATC TGC CTC TCA ATC TTG GAT AGG AGT            629
Phe Glu Glu Asp Ile Leu Ser Ile Cys Leu Ser Ile Leu Asp Arg Ser
             185                 190                 195

CTG AAT TTC CGC CGT GAC GCT GCT ACT GAT GTG GCC AGC AGA AAT GAC            677
Leu Asn Phe Arg Arg Asp Ala Ala Thr Asp Val Ala Ser Arg Asn Asp
             200                 205                 210

CCC AAA TAC GTT GGC CGG GTG CTG AGT GCC ATG ATC AAT AGC AAT GAT            725
Pro Lys Tyr Val Gly Arg Val Leu Ser Ala Met Ile Asn Ser Asn Asp
             215                 220                 225

GAC AAT GGT GTG CTT GCT GGG AAT TGG AGC GGC ACT TAC ACC GGT GGC            773
Asp Asn Gly Val Leu Ala Gly Asn Trp Ser Gly Thr Tyr Thr Gly Gly
             230                 235                 240

CGG GAC CCA AGG AGC TGG GAC GGC AGC GTG GAG ATC CTC AAA AAT TGG            821
Arg Asp Pro Arg Ser Trp Asp Gly Ser Val Glu Ile Leu Lys Asn Trp
```

| | | | | | | | | | | | | | | | | |
|---|---|---|---|---|---|---|---|---|---|---|---|---|---|---|---|---|
| 245 | | | | | 250 | | | | | 255 | | | | | 260 | |
| AAA<br>Lys | AAA<br>Lys | TCT<br>Ser | GGC<br>Gly | TTC<br>Phe<br>265 | AGC<br>Ser | CCA<br>Pro | GTC<br>Val | CGA<br>Arg | TAT<br>Tyr<br>270 | GGC<br>Gly | CAG<br>Gln | TGC<br>Cys | TGG<br>Trp | GTC<br>Val<br>275 | TTT<br>Phe | 869 |
| GCT<br>Ala | GGG<br>Gly | ACC<br>Thr | CTC<br>Leu<br>280 | AAC<br>Asn | ACA<br>Thr | GCG<br>Ala | CTG<br>Leu | CGG<br>Arg<br>285 | TCT<br>Ser | TTG<br>Leu | GGG<br>Gly | ATT<br>Ile | CCT<br>Pro<br>290 | TCC<br>Ser | CGG<br>Arg | 917 |
| GTG<br>Val | ATC<br>Ile | ACC<br>Thr<br>295 | AAC<br>Asn | TTC<br>Phe | AAC<br>Asn | TCA<br>Ser | GCT<br>Ala | CAT<br>His<br>300 | GAC<br>Asp | ACA<br>Thr | GAC<br>Asp | CGA<br>Arg<br>305 | AAT<br>Asn | CTC<br>Leu | AGT<br>Ser | 965 |
| GTG<br>Val | GAT<br>Asp<br>310 | GTG<br>Val | TAC<br>Tyr | TAC<br>Tyr | GAC<br>Asp | CCC<br>Pro<br>315 | ATG<br>Met | GGA<br>Gly | AAC<br>Asn | CCC<br>Pro | CTG<br>Leu<br>320 | GAC<br>Asp | AAG<br>Lys | GGT<br>Gly | AGT<br>Ser | 1013 |
| GAT<br>Asp<br>325 | AGC<br>Ser | GTA<br>Val | TGG<br>Trp | AAT<br>Asn | TTC<br>Phe<br>330 | CAT<br>His | GTC<br>Val | TGG<br>Trp | AAT<br>Asn | GAA<br>Glu<br>335 | GGC<br>Gly | TGG<br>Trp | TTT<br>Phe | GTG<br>Val | AGG<br>Arg<br>340 | 1061 |
| TCT<br>Ser | GAC<br>Asp | CTG<br>Leu | GGC<br>Gly | CCC<br>Pro<br>345 | CCG<br>Pro | TAC<br>Tyr | GGT<br>Gly | GGA<br>Gly | TGG<br>Trp<br>350 | CAG<br>Gln | GTG<br>Val | TTG<br>Leu | GAT<br>Asp | GCT<br>Ala<br>355 | ACC<br>Thr | 1109 |
| CCG<br>Pro | CAG<br>Gln | GAA<br>Glu | AGA<br>Arg<br>360 | AGC<br>Ser | CAA<br>Gln | GGG<br>Gly | GTG<br>Val | TTC<br>Phe<br>365 | CAG<br>Gln | TGC<br>Cys | GGC<br>Gly | CCC<br>Pro | GCT<br>Ala<br>370 | TCG<br>Ser | GTC<br>Val | 1157 |
| ATT<br>Ile | GGT<br>Gly | GTT<br>Val<br>375 | CGA<br>Arg | GAG<br>Glu | GGT<br>Gly | GAT<br>Asp | GTG<br>Val<br>380 | CAG<br>Gln | CTG<br>Leu | AAC<br>Asn | TTC<br>Phe | GAC<br>Asp<br>385 | ATG<br>Met | CCC<br>Pro | TTT<br>Phe | 1205 |
| ATC<br>Ile | TTC<br>Phe<br>390 | GCG<br>Ala | GAG<br>Glu | GTT<br>Val | AAT<br>Asn | GCC<br>Ala<br>395 | GAC<br>Asp | CGC<br>Arg | ATC<br>Ile | ACC<br>Thr | TGG<br>Trp<br>400 | CTG<br>Leu | TAC<br>Tyr | GAC<br>Asp | AAC<br>Asn | 1253 |
| ACC<br>Thr<br>405 | ACT<br>Thr | GGC<br>Gly | AAA<br>Lys | CAG<br>Gln | TGG<br>Trp<br>410 | AAG<br>Lys | AAT<br>Asn | TCC<br>Ser | GTG<br>Val | AAC<br>Asn<br>415 | AGT<br>Ser | CAC<br>His | ACC<br>Thr | ATT<br>Ile | GGC<br>Gly<br>420 | 1301 |
| AGG<br>Arg | TAC<br>Tyr | ATC<br>Ile | AGC<br>Ser | ACC<br>Thr<br>425 | AAG<br>Lys | GCG<br>Ala | GTG<br>Val | GGC<br>Gly | AGC<br>Ser<br>430 | AAT<br>Asn | GCT<br>Ala | CGC<br>Arg | ATG<br>Met | GAC<br>Asp<br>435 | GTC<br>Val | 1349 |
| ACG<br>Thr | GAC<br>Asp | AAG<br>Lys | TAC<br>Tyr<br>440 | AAG<br>Lys | TAC<br>Tyr | CCA<br>Pro | GAA<br>Glu | GGC<br>Gly<br>445 | TCT<br>Ser | GAC<br>Asp | CAG<br>Gln | GAA<br>Glu | AGA<br>Arg<br>450 | CAA<br>Gln | GTG<br>Val | 1397 |
| TTC<br>Phe | CAA<br>Gln | AAG<br>Lys<br>455 | GCT<br>Ala | TTG<br>Leu | GGG<br>Gly | AAA<br>Lys | CTT<br>Leu<br>460 | AAA<br>Lys | CCC<br>Pro | AAC<br>Asn | ACG<br>Thr | CCA<br>Pro<br>465 | TTT<br>Phe | GCC<br>Ala | GCG<br>Ala | 1445 |
| ACG<br>Thr | TCT<br>Ser<br>470 | TCG<br>Ser | ATG<br>Met | GGT<br>Gly | TTG<br>Leu | GAA<br>Glu<br>475 | ACA<br>Thr | GAG<br>Glu | GAA<br>Glu | CAG<br>Gln | GAG<br>Glu<br>480 | CCC<br>Pro | AGC<br>Ser | ATC<br>Ile | ATC<br>Ile | 1493 |
| GGG<br>Gly<br>485 | AAG<br>Lys | CTG<br>Leu | AAG<br>Lys | GTC<br>Val | GCT<br>Ala<br>490 | GGC<br>Gly | ATG<br>Met | CTG<br>Leu | GCA<br>Ala | GTA<br>Val<br>495 | GGC<br>Gly | AAA<br>Lys | GAA<br>Glu | GTC<br>Val | AAC<br>Asn<br>500 | 1541 |
| CTG<br>Leu | GTC<br>Val | CTA<br>Leu | CTG<br>Leu | CTC<br>Leu<br>505 | AAA<br>Lys | AAC<br>Asn | CTG<br>Leu | AGC<br>Ser | AGG<br>Arg<br>510 | GAT<br>Asp | ACG<br>Thr | AAG<br>Lys | ACA<br>Thr | GTG<br>Val<br>515 | ACA<br>Thr | 1589 |
| GTG<br>Val | AAC<br>Asn | ATG<br>Met | ACA<br>Thr<br>520 | GCC<br>Ala | TGG<br>Trp | ACC<br>Thr | ATC<br>Ile | ATC<br>Ile<br>525 | TAC<br>Tyr | AAC<br>Asn | GGC<br>Gly | ACG<br>Thr | CTT<br>Leu<br>530 | GTA<br>Val | CAT<br>His | 1637 |
| GAA<br>Glu | GTG<br>Val | TGG<br>Trp<br>535 | AAG<br>Lys | GAC<br>Asp | TCT<br>Ser | GCC<br>Ala | ACA<br>Thr<br>540 | ATG<br>Met | TCC<br>Ser | CTG<br>Leu | GAC<br>Asp | CCT<br>Pro<br>545 | GAG<br>Glu | GAA<br>Glu | GAG<br>Glu | 1685 |
| GCA<br>Ala | GAA<br>Glu | CAT<br>His<br>550 | CCC<br>Pro | ATA<br>Ile | AAG<br>Lys | ATC<br>Ile | TCG<br>Ser<br>555 | TAC<br>Tyr | GCT<br>Ala | CAG<br>Gln | TAT<br>Tyr | GAG<br>Glu<br>560 | AGG<br>Arg | TAC<br>Tyr | CTG<br>Leu | 1733 |
| AAG<br>Lys | TCA<br>Ser | GAC<br>Asp | AAC<br>Asn | ATG<br>Met | ATC<br>Ile | CGG<br>Arg | ATC<br>Ile | ACA<br>Thr | GCG<br>Ala | GTG<br>Val | TGC<br>Cys | AAG<br>Lys | GTC<br>Val | CCA<br>Pro | GAT<br>Asp | 1781 |

```
                        565                              570                                575                              580
GAG   TCT   GAG   GTG   GTG   GTG   GAG   CGG   GAC   ATC   ATC   CTG   GAC   AAC   CCC   ACC                         1829
Glu   Ser   Glu   Val   Val   Val   Glu   Arg   Asp   Ile   Ile   Leu   Asp   Asn   Pro   Thr
                        585                              590                                595

TTG   ACC   CTG   GAG   GTG   CTG   AAC   GAG   GCT   CGT   GTG   CGG   AAG   CCT   GTG   AAC                         1877
Leu   Thr   Leu   Glu   Val   Leu   Asn   Glu   Ala   Arg   Val   Arg   Lys   Pro   Val   Asn
                        600                              605                                610

GTG   CAG   ATG   CTC   TTC   TCC   AAT   CCA   CTG   GAT   GAG   CCG   GTG   AGG   GAC   TGC                         1925
Val   Gln   Met   Leu   Phe   Ser   Asn   Pro   Leu   Asp   Glu   Pro   Val   Arg   Asp   Cys
                  615                              620                                625

GTG   CTG   ATG   GTG   GAG   GGA   AGC   GGC   CTG   CTG   TTG   GGT   AAC   CTG   AAG   ATC                         1973
Val   Leu   Met   Val   Glu   Gly   Ser   Gly   Leu   Leu   Leu   Gly   Asn   Leu   Lys   Ile
            630                              635                                640

GAC   GTG   CCG   ACC   CTA   GGG   CCC   AAG   GAG   CGG   TCC   CGG   GTC   CGT   TTT   GAT                         2021
Asp   Val   Pro   Thr   Leu   Gly   Pro   Lys   Glu   Arg   Ser   Arg   Val   Arg   Phe   Asp
645                              650                              655                              660

ATC   CTG   CCC   TCC   CGG   AGT   GGC   ACC   AAG   CAA   CTG   CTC   GCC   GAC   TTC   TCC                         2069
Ile   Leu   Pro   Ser   Arg   Ser   Gly   Thr   Lys   Gln   Leu   Leu   Ala   Asp   Phe   Ser
                        665                              670                                675

TGC   AAC   AAG   TTC   CCT   GCA   ATC   AAG   GCC   ATG   TTG   TCC   ATC   GAC   GTA   GCC                         2117
Cys   Asn   Lys   Phe   Pro   Ala   Ile   Lys   Ala   Met   Leu   Ser   Ile   Asp   Val   Ala
                  680                              685                                690

GAA   TGAAGGGCGC   TGGTGGCCTC   CCGTACAAAC   TTGGACAACA   CGGAGCAGGG                                                    2170
Glu

AGAGCTCACC   ATGGAATGAA   CCCCCCGCCC   ATGCTGTCCG   GCCTGGGAAA   CCCTCTCCAT                                             2230

CTCCCAAGGC   TGCCAGACAT   GGACTCCGGG   CTCCAGCACA   TCCCCCTCTC   CTCTCCCCCA                                             2290

GGTTGGGGCT   GGGTCCACCC   TGTCCTATGA   CTTGATCACT   TTTGCACATT   CCCTGGCCGT                                             2350

TTCTCCCCAG   AGCTGCCTGC   TCTGTGAGCC   CCACAGCCCT   GCTCATTCCT   CACGCCCTTC                                             2410

AATGCTGCAG   GATGGACTGG   CCCCTGACCC   AGGGACTCTC   CAAACGGGAT   ACAGGAGAGA                                             2470

AGCTGGTCTA   GACTGTTTGC   TGATCCCCAA   CCTGCACGGG   GCATTCCTGC   TTCTCTCTCA                                             2530

GGCCACCACA   GAGGGCAGGG   GATGGTTAGT   CACCTGCCCC   AGCACTCACA   CCCTAACTCA                                             2590

AAATAAATGT   TAAATAAGTG   CGATCACACA                                                                                   2620
```

( 2 ) INFORMATION FOR SEQ ID NO:110:

( i ) SEQUENCE CHARACTERISTICS:
        ( A ) LENGTH: 2297 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 55..2133

( x i ) SEQUENCE DESCRIPTION: SEQ ID NO:110:

```
ACACCATCTC   TGTCATTCCC   AGAGGAGCCC   CAGGAAAGGC   AGAAGAAGCT   GACC   ATG                                            57
                                                                        Met
                                                                        1

AGT   GCT   TTA   CAG   ATC   CAA   AAC   GTC   AAC   TGG   CAG   GTG   CCT   ATG   AAT   CGA                         105
Ser   Ala   Leu   Gln   Ile   Gln   Asn   Val   Asn   Trp   Gln   Val   Pro   Met   Asn   Arg
                  5                                10                                 15

AGG   GCG   CAT   CAC   ACA   GAC   AAG   TTC   TCC   AGC   CAG   GAT   TCT   ATT   GTG   CGG                         153
Arg   Ala   His   His   Thr   Asp   Lys   Phe   Ser   Ser   Gln   Asp   Ser   Ile   Val   Arg
```

|  |  |  |  |  |  |  |  |  |  |  |  |  |  |  |  |  |
|---|---|---|---|---|---|---|---|---|---|---|---|---|---|---|---|---|
|  | 20 |  |  |  |  | 25 |  |  |  |  | 30 |  |  |  |  |  |
| AGA | GGA | CAG | CCC | TGG | GAG | ATA | ATA | TTA | GTC | TGC | AAC | CGA | AGT | CTT | GAG | 201 |
| Arg | Gly | Gln | Pro | Trp | Glu | Ile | Ile | Leu | Val | Cys | Asn | Arg | Ser | Leu | Glu |  |
|  | 35 |  |  |  | 40 |  |  |  |  | 45 |  |  |  |  |  |  |
| TCT | GGA | GAA | GAT | CTG | AAT | TTC | ATT | GTT | TCC | ACA | GGT | CCC | CAA | CCC | TCT | 249 |
| Ser | Gly | Glu | Asp | Leu | Asn | Phe | Ile | Val | Ser | Thr | Gly | Pro | Gln | Pro | Ser |  |
| 50 |  |  |  |  | 55 |  |  |  |  | 60 |  |  |  |  | 65 |  |
| GAG | TCA | GCC | AGG | ACA | AAG | GCT | GTG | TTT | TCC | ATC | TCT | GGG | AGA | AGC | ACG | 297 |
| Glu | Ser | Ala | Arg | Thr | Lys | Ala | Val | Phe | Ser | Ile | Ser | Gly | Arg | Ser | Thr |  |
|  |  |  | 70 |  |  |  |  | 75 |  |  |  |  | 80 |  |  |  |
| GGT | GGC | TGG | AAT | GCA | GCG | CTC | AAA | GCC | AAC | AGT | GGC | AAT | AAT | CTG | GCC | 345 |
| Gly | Gly | Trp | Asn | Ala | Ala | Leu | Lys | Ala | Asn | Ser | Gly | Asn | Asn | Leu | Ala |  |
|  |  |  | 85 |  |  |  |  | 90 |  |  |  |  | 95 |  |  |  |
| ATT | GCT | ATT | GCC | AGT | CCT | GTC | AGT | GCT | CCC | ATC | GGA | TTG | TAC | ACA | CTG | 393 |
| Ile | Ala | Ile | Ala | Ser | Pro | Val | Ser | Ala | Pro | Ile | Gly | Leu | Tyr | Thr | Leu |  |
|  |  | 100 |  |  |  |  | 105 |  |  |  |  | 110 |  |  |  |  |
| AGT | GTT | GAG | ATC | TCC | TCC | AGG | GGC | AGG | GCC | TCC | TCT | CTG | AAA | CTT | GGC | 441 |
| Ser | Val | Glu | Ile | Ser | Ser | Arg | Gly | Arg | Ala | Ser | Ser | Leu | Lys | Leu | Gly |  |
|  | 115 |  |  |  |  | 120 |  |  |  |  | 125 |  |  |  |  |  |
| ACG | TTT | ATA | ATG | CTC | TTC | AAC | CCG | TGG | TTG | CAA | GCG | GAT | GAT | GTC | TTT | 489 |
| Thr | Phe | Ile | Met | Leu | Phe | Asn | Pro | Trp | Leu | Gln | Ala | Asp | Asp | Val | Phe |  |
| 130 |  |  |  |  | 135 |  |  |  |  | 140 |  |  |  |  | 145 |  |
| ATG | AGT | AAC | CAC | GCC | GAA | AGA | CAA | GAG | TAT | GTT | GAA | GAA | GAT | TCT | GGC | 537 |
| Met | Ser | Asn | His | Ala | Glu | Arg | Gln | Glu | Tyr | Val | Glu | Glu | Asp | Ser | Gly |  |
|  |  |  | 150 |  |  |  |  | 155 |  |  |  |  | 160 |  |  |  |
| ATC | ATC | TAT | GTG | GGC | AGC | ACA | AAT | CGA | ATT | GGC | ATG | GTT | GGC | TGG | AAC | 585 |
| Ile | Ile | Tyr | Val | Gly | Ser | Thr | Asn | Arg | Ile | Gly | Met | Val | Gly | Trp | Asn |  |
|  |  |  | 165 |  |  |  |  | 170 |  |  |  |  | 175 |  |  |  |
| TTT | GGA | CAG | TTT | GAA | GAA | GAC | ATT | CTG | AAC | ATC | AGC | CTC | TCC | ATT | TTG | 633 |
| Phe | Gly | Gln | Phe | Glu | Glu | Asp | Ile | Leu | Asn | Ile | Ser | Leu | Ser | Ile | Leu |  |
|  |  | 180 |  |  |  |  | 185 |  |  |  |  | 190 |  |  |  |  |
| GAT | AGG | AGT | CTG | AAT | TTC | CGT | CGT | GAC | CCT | GTG | ACT | GAT | GTG | GCT | CGC | 681 |
| Asp | Arg | Ser | Leu | Asn | Phe | Arg | Arg | Asp | Pro | Val | Thr | Asp | Val | Ala | Arg |  |
|  | 195 |  |  |  |  | 200 |  |  |  |  | 205 |  |  |  |  |  |
| AGA | AAT | GAC | CCC | AAA | TAT | GTG | TGC | CGG | GTG | CTG | AGT | GCC | ATG | ATT | AAT | 729 |
| Arg | Asn | Asp | Pro | Lys | Tyr | Val | Cys | Arg | Val | Leu | Ser | Ala | Met | Ile | Asn |  |
| 210 |  |  |  |  | 215 |  |  |  |  | 220 |  |  |  |  | 225 |  |
| GGC | AAT | GAT | GAC | AAC | GGT | GTG | ATT | TCT | GGG | AAC | TGG | AGT | GGT | AAT | TAC | 777 |
| Gly | Asn | Asp | Asp | Asn | Gly | Val | Ile | Ser | Gly | Asn | Trp | Ser | Gly | Asn | Tyr |  |
|  |  |  |  | 230 |  |  |  |  | 235 |  |  |  |  | 240 |  |  |
| ACC | GGT | GGT | GTG | GAC | CCA | AGG | ACC | TGG | AAT | GGT | AGT | GTG | GAG | ATC | CTC | 825 |
| Thr | Gly | Gly | Val | Asp | Pro | Arg | Thr | Trp | Asn | Gly | Ser | Val | Glu | Ile | Leu |  |
|  |  |  | 245 |  |  |  |  | 250 |  |  |  |  | 255 |  |  |  |
| AAG | AAC | TGG | AAA | AAA | TCT | GGC | TTC | AGG | CCA | GTC | CAA | TTT | GGC | CAG | TGC | 873 |
| Lys | Asn | Trp | Lys | Lys | Ser | Gly | Phe | Arg | Pro | Val | Gln | Phe | Gly | Gln | Cys |  |
|  |  | 260 |  |  |  |  | 265 |  |  |  |  | 270 |  |  |  |  |
| TGG | GTC | TTT | GCT | GGA | ACC | CTC | AAC | ACA | GTG | CTG | CGG | TGC | TTG | GGG | GTT | 921 |
| Trp | Val | Phe | Ala | Gly | Thr | Leu | Asn | Thr | Val | Leu | Arg | Cys | Leu | Gly | Val |  |
|  | 275 |  |  |  |  | 280 |  |  |  |  | 285 |  |  |  |  |  |
| CGC | TCT | CGG | GTG | ATC | ACC | AAC | TTC | AAC | TCG | GCT | CAC | GAC | ACA | GAT | CGA | 969 |
| Arg | Ser | Arg | Val | Ile | Thr | Asn | Phe | Asn | Ser | Ala | His | Asp | Thr | Asp | Arg |  |
| 290 |  |  |  |  | 295 |  |  |  |  | 300 |  |  |  |  | 305 |  |
| AAC | CTC | AGT | GTG | GAT | GTG | TAC | TAC | GAT | GCC | ATG | GGA | AAT | CCC | CTG | GAG | 1017 |
| Asn | Leu | Ser | Val | Asp | Val | Tyr | Tyr | Asp | Ala | Met | Gly | Asn | Pro | Leu | Glu |  |
|  |  |  |  | 310 |  |  |  |  | 315 |  |  |  |  | 320 |  |  |
| AAA | GGA | AGT | GAT | AGC | GTG | TGG | AAT | TTT | CAC | GTC | TGG | AAT | GAA | GGC | TGG | 1065 |
| Lys | Gly | Ser | Asp | Ser | Val | Trp | Asn | Phe | His | Val | Trp | Asn | Glu | Gly | Trp |  |
|  |  |  | 325 |  |  |  |  | 330 |  |  |  |  | 335 |  |  |  |
| TTC | GTG | CGG | ACT | GAC | CTA | GGC | CCC | ACA | TAC | AAT | GGA | TGG | CAG | GTG | CTG | 1113 |
| Phe | Val | Arg | Thr | Asp | Leu | Gly | Pro | Thr | Tyr | Asn | Gly | Trp | Gln | Val | Leu |  |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 340 |     |     |     |     | 345 |     |     |     |     |     | 350 |     |     |      |
| GAT | GCC | ACC | CCC | CAG | GAG | AGA | AGC | CAA | GGC | GTA | TTC | CAG | TGC | GGT | CCA | 1161 |
| Asp | Ala | Thr | Pro | Gln | Glu | Arg | Ser | Gln | Gly | Val | Phe | Gln | Cys | Gly | Pro |      |
|     | 355 |     |     |     | 360 |     |     |     |     | 365 |     |     |     |     |     |      |
| GCT | TCC | GTT | AAT | GCA | ATC | AAA | GCC | GGT | GAT | GTG | GAC | CGG | AAT | TTT | GAC | 1209 |
| Ala | Ser | Val | Asn | Ala | Ile | Lys | Ala | Gly | Asp | Val | Asp | Arg | Asn | Phe | Asp |      |
| 370 |     |     |     | 375 |     |     |     |     | 380 |     |     |     |     | 385 |     |      |
| ATG | ATC | TTC | ATC | TTC | GCG | GAG | GTT | AAT | GCA | GAT | CGC | ATC | ACT | TGG | ATC | 1257 |
| Met | Ile | Phe | Ile | Phe | Ala | Glu | Val | Asn | Ala | Asp | Arg | Ile | Thr | Trp | Ile |      |
|     |     |     |     | 390 |     |     |     |     | 395 |     |     |     |     | 400 |     |      |
| TAT | AAT | AAT | AGA | AAT | AAC | ACC | CAG | AAG | CAG | AAT | TCT | GTG | GAC | ACT | CAC | 1305 |
| Tyr | Asn | Asn | Arg | Asn | Asn | Thr | Gln | Lys | Gln | Asn | Ser | Val | Asp | Thr | His |      |
|     |     |     | 405 |     |     |     |     | 410 |     |     |     |     | 415 |     |     |      |
| TCC | ATT | GGC | AAA | TAC | ATC | AGC | ACC | AAG | GCA | GTA | GGC | AGC | AAC | TCT | CGC | 1353 |
| Ser | Ile | Gly | Lys | Tyr | Ile | Ser | Thr | Lys | Ala | Val | Gly | Ser | Asn | Ser | Arg |      |
|     |     | 420 |     |     |     |     | 425 |     |     |     |     | 430 |     |     |     |      |
| ATG | GAT | GTC | ACA | GAC | AAG | TAC | AAG | TAT | CCA | GAA | GGT | TCC | AGT | GAG | GAA | 1401 |
| Met | Asp | Val | Thr | Asp | Lys | Tyr | Lys | Tyr | Pro | Glu | Gly | Ser | Ser | Glu | Glu |      |
|     | 435 |     |     |     |     | 440 |     |     |     |     | 445 |     |     |     |     |      |
| AGA | CAA | GTG | CAC | CAA | AAG | GCT | TTG | GAC | AAA | CTC | AAA | CCT | AAC | GCA | TCT | 1449 |
| Arg | Gln | Val | His | Gln | Lys | Ala | Leu | Asp | Lys | Leu | Lys | Pro | Asn | Ala | Ser |      |
| 450 |     |     |     |     | 455 |     |     |     |     | 460 |     |     |     |     | 465 |      |
| TTT | GGC | GCA | ACA | TCT | TCG | AGG | AAT | CCA | GAA | GGG | GAA | GAC | AAG | GAG | CCC | 1497 |
| Phe | Gly | Ala | Thr | Ser | Ser | Arg | Asn | Pro | Glu | Gly | Glu | Asp | Lys | Glu | Pro |      |
|     |     |     |     | 470 |     |     |     |     | 475 |     |     |     |     | 480 |     |      |
| AGC | ATT | TCT | GGG | AAG | TTC | AAG | GTC | ACG | GGC | ATA | CTG | GCA | GTA | GGC | AAA | 1545 |
| Ser | Ile | Ser | Gly | Lys | Phe | Lys | Val | Thr | Gly | Ile | Leu | Ala | Val | Gly | Lys |      |
|     |     |     | 485 |     |     |     |     | 490 |     |     |     |     | 495 |     |     |      |
| GAA | GTC | AGT | CTG | TCC | CTG | ATG | CTC | AAA | AAC | ATG | ACT | AAT | GAC | AGG | AAG | 1593 |
| Glu | Val | Ser | Leu | Ser | Leu | Met | Leu | Lys | Asn | Met | Thr | Asn | Asp | Arg | Lys |      |
|     |     | 500 |     |     |     |     | 505 |     |     |     |     | 510 |     |     |     |      |
| ACA | GTG | ACG | ATG | AAC | ATG | ACA | GCC | TGG | ACC | ATC | GTC | TAC | AAT | GGT | ACC | 1641 |
| Thr | Val | Thr | Met | Asn | Met | Thr | Ala | Trp | Thr | Ile | Val | Tyr | Asn | Gly | Thr |      |
|     | 515 |     |     |     |     | 520 |     |     |     |     | 525 |     |     |     |     |      |
| CTT | GTC | CAC | GAA | GTG | TGG | AAG | GAC | TCA | GCC | ACA | ATA | TCC | TTG | GAT | CCT | 1689 |
| Leu | Val | His | Glu | Val | Trp | Lys | Asp | Ser | Ala | Thr | Ile | Ser | Leu | Asp | Pro |      |
| 530 |     |     |     |     | 535 |     |     |     |     | 540 |     |     |     |     | 545 |      |
| GAA | GAA | GAA | ATA | CAG | TAT | CCT | GTG | AAG | ATC | GCA | TAC | TCT | CAG | TAT | GAG | 1737 |
| Glu | Glu | Glu | Ile | Gln | Tyr | Pro | Val | Lys | Ile | Ala | Tyr | Ser | Gln | Tyr | Glu |      |
|     |     |     |     | 550 |     |     |     |     | 555 |     |     |     |     | 560 |     |      |
| AGA | TAC | CTG | AAG | GCA | GAC | AAC | ATG | ATC | CGG | ATC | TCA | GCC | GTT | TGC | AAG | 1785 |
| Arg | Tyr | Leu | Lys | Ala | Asp | Asn | Met | Ile | Arg | Ile | Ser | Ala | Val | Cys | Lys |      |
|     |     |     | 565 |     |     |     |     | 570 |     |     |     |     | 575 |     |     |      |
| GTG | CCC | GAT | GAG | GCT | GAG | GTG | GTG | GTG | GAA | TGG | GAT | GTC | ATC | CTG | GAT | 1833 |
| Val | Pro | Asp | Glu | Ala | Glu | Val | Val | Val | Glu | Trp | Asp | Val | Ile | Leu | Asp |      |
|     |     | 580 |     |     |     |     | 585 |     |     |     |     | 590 |     |     |     |      |
| AAT | CCT | GCT | TTG | ACC | CTG | GAG | GTG | CTG | GAA | CAG | GCT | CAT | GTG | CGG | AAG | 1881 |
| Asn | Pro | Ala | Leu | Thr | Leu | Glu | Val | Leu | Glu | Gln | Ala | His | Val | Arg | Lys |      |
|     | 595 |     |     |     |     | 600 |     |     |     |     | 605 |     |     |     |     |      |
| CCC | GTG | AAC | GTG | CAG | ATG | ATT | TTC | TCC | AAC | CCC | CTG | GAC | CAG | CCG | GTG | 1929 |
| Pro | Val | Asn | Val | Gln | Met | Ile | Phe | Ser | Asn | Pro | Leu | Asp | Gln | Pro | Val |      |
| 610 |     |     |     |     | 615 |     |     |     |     | 620 |     |     |     |     | 625 |      |
| AGG | AAC | TGC | GTG | CTG | CTG | GTG | GAG | GGC | AGC | GGC | TGC | TCG | GTG | GCA | GCC | 1977 |
| Arg | Asn | Cys | Val | Leu | Leu | Val | Glu | Gly | Ser | Gly | Cys | Ser | Val | Ala | Ala |      |
|     |     |     |     | 630 |     |     |     |     | 635 |     |     |     |     | 640 |     |      |
| TCA | AGA | TTG | ATG | TGC | CAT | CCC | TGC | GTC | CCC | AAG | GAG | AAG | TCC | CGC | ATC | 2025 |
| Ser | Arg | Leu | Met | Cys | His | Pro | Cys | Val | Pro | Lys | Glu | Lys | Ser | Arg | Ile |      |
|     |     |     | 645 |     |     |     |     | 650 |     |     |     |     | 655 |     |     |      |
| CGA | TTT | GAG | ATT | TTC | CCC | ACT | CGG | AGT | GGC | ACC | AAG | CAA | CTG | CTC | GCT | 2073 |
| Arg | Phe | Glu | Ile | Phe | Pro | Thr | Arg | Ser | Gly | Thr | Lys | Gln | Leu | Leu | Ala |      |

```
                        660                     665                     670
GAC  TTT  TCC  TGC  AAT  AAA  TTC  CCT  ACT  ATC  AAG  GCC  ATG  CTG  CCC  ATT      2121
Asp  Phe  Ser  Cys  Asn  Lys  Phe  Pro  Thr  Ile  Lys  Ala  Met  Leu  Pro  Ile
675                      680                          685

GAT  GTC  TCT  GAG  TGACCGACCC  AGCAGCACTC  CCACAGACGT  CGGTGACACA               2173
Asp  Val  Ser  Glu
690

GACCAGACAG  CGCTCTCCTG  TGGAGTGAAA  CTGTTGCCTA  TGTTGTCCAG  CCTGAGAAGC           2233

CCTCCATGTC  CCCAAGGCTG  CCAGACATGG  ACTTCTAGCA  AGTCCCCCAA  CCCCCCATTC           2293

AACC                                                                             2297
```

( 2 ) INFORMATION FOR SEQ ID NO:111:

( i ) SEQUENCE CHARACTERISTICS:
        ( A ) LENGTH: 693 amino acids
        ( B ) TYPE: amino acid
        ( D ) TOPOLOGY: linear ( i i ) MOLECULE TYPE: protein ( x i ) SEQUENCE DESCRIPTION: SEQ ID NO:111:

```
Met  Ser  Ala  Leu  Gln  Ile  Gln  Asn  Val  Asn  Trp  Gln  Val  Pro  Met  Asn
1                   5                        10                      15

Arg  Arg  Ala  His  His  Thr  Asp  Lys  Phe  Ser  Ser  Gln  Asp  Ser  Ile  Val
                20                      25                     30

Arg  Arg  Gly  Gln  Pro  Trp  Glu  Ile  Ile  Leu  Val  Cys  Asn  Arg  Ser  Leu
              35                      40                      45

Glu  Ser  Gly  Glu  Asp  Leu  Asn  Phe  Ile  Val  Ser  Thr  Gly  Pro  Gln  Pro
     50                      55                      60

Ser  Glu  Ser  Ala  Arg  Thr  Lys  Ala  Val  Phe  Ser  Ile  Ser  Gly  Arg  Ser
65                       70                      75                           80

Thr  Gly  Gly  Trp  Asn  Ala  Ala  Leu  Lys  Ala  Asn  Ser  Gly  Asn  Asn  Leu
                    85                      90                      95

Ala  Ile  Ala  Ile  Ala  Ser  Pro  Val  Ser  Ala  Pro  Ile  Gly  Leu  Tyr  Thr
               100                     105                     110

Leu  Ser  Val  Glu  Ile  Ser  Ser  Arg  Gly  Arg  Ala  Ser  Ser  Leu  Lys  Leu
          115                     120                     125

Gly  Thr  Phe  Ile  Met  Leu  Phe  Asn  Pro  Trp  Leu  Gln  Ala  Asp  Asp  Val
     130                     135                     140

Phe  Met  Ser  Asn  His  Ala  Glu  Arg  Gln  Glu  Tyr  Val  Glu  Glu  Asp  Ser
145                      150                     155                          160

Gly  Ile  Ile  Tyr  Val  Gly  Ser  Thr  Asn  Arg  Ile  Gly  Met  Val  Gly  Trp
               165                     170                     175

Asn  Phe  Gly  Gln  Phe  Glu  Glu  Asp  Ile  Leu  Asn  Ile  Ser  Leu  Ser  Ile
               180                     185                     190

Leu  Asp  Arg  Ser  Leu  Asn  Phe  Arg  Arg  Asp  Pro  Val  Thr  Asp  Val  Ala
          195                     200                     205

Arg  Arg  Asn  Asp  Pro  Lys  Tyr  Val  Cys  Arg  Val  Leu  Ser  Ala  Met  Ile
     210                     215                     220

Asn  Gly  Asn  Asp  Asp  Asn  Gly  Val  Ile  Ser  Gly  Asn  Trp  Ser  Gly  Asn
225                      230                     235                          240

Tyr  Thr  Gly  Gly  Val  Asp  Pro  Arg  Thr  Trp  Asn  Gly  Ser  Val  Glu  Ile
               245                     250                     255

Leu  Lys  Asn  Trp  Lys  Lys  Ser  Gly  Phe  Arg  Pro  Val  Gln  Phe  Gly  Gln
               260                     265                     270

Cys  Trp  Val  Phe  Ala  Gly  Thr  Leu  Asn  Thr  Val  Leu  Arg  Cys  Leu  Gly
```

|     |     |     | 275 |     |     |     | 280 |     |     |     | 285 |     |     |     |
| --- | --- | --- | --- | --- | --- | --- | --- | --- | --- | --- | --- | --- | --- | --- |

Val Arg Ser Arg Val Ile Thr Asn Phe Asn Ser Ala His Asp Thr Asp
290                     295                     300

Arg Asn Leu Ser Val Asp Val Tyr Tyr Asp Ala Met Gly Asn Pro Leu
305                     310                     315                     320

Glu Lys Gly Ser Asp Ser Val Trp Asn Phe His Val Trp Asn Glu Gly
                        325                     330                     335

Trp Phe Val Arg Thr Asp Leu Gly Pro Thr Tyr Asn Gly Trp Gln Val
            340                     345                     350

Leu Asp Ala Thr Pro Gln Glu Arg Ser Gln Gly Val Phe Gln Cys Gly
            355                     360                     365

Pro Ala Ser Val Asn Ala Ile Lys Ala Gly Asp Val Asp Arg Asn Phe
370                     375                     380

Asp Met Ile Phe Ile Phe Ala Glu Val Asn Ala Asp Arg Ile Thr Trp
385                     390                     395                     400

Ile Tyr Asn Asn Arg Asn Asn Thr Gln Lys Gln Asn Ser Val Asp Thr
                405                     410                     415

His Ser Ile Gly Lys Tyr Ile Ser Thr Lys Ala Val Gly Ser Asn Ser
            420                     425                     430

Arg Met Asp Val Thr Asp Lys Tyr Lys Tyr Pro Glu Gly Ser Ser Glu
            435                     440                     445

Glu Arg Gln Val His Gln Lys Ala Leu Asp Lys Leu Lys Pro Asn Ala
    450                     455                     460

Ser Phe Gly Ala Thr Ser Ser Arg Asn Pro Glu Gly Glu Asp Lys Glu
465                     470                     475                     480

Pro Ser Ile Ser Gly Lys Phe Lys Val Thr Gly Ile Leu Ala Val Gly
            485                     490                     495

Lys Glu Val Ser Leu Ser Leu Met Leu Lys Asn Met Thr Asn Asp Arg
            500                     505                     510

Lys Thr Val Thr Met Asn Met Thr Ala Trp Thr Ile Val Tyr Asn Gly
        515                     520                     525

Thr Leu Val His Glu Val Trp Lys Asp Ser Ala Thr Ile Ser Leu Asp
530                     535                     540

Pro Glu Glu Glu Ile Gln Tyr Pro Val Lys Ile Ala Tyr Ser Gln Tyr
545                     550                     555                     560

Glu Arg Tyr Leu Lys Ala Asp Asn Met Ile Arg Ile Ser Ala Val Cys
                565                     570                     575

Lys Val Pro Asp Glu Ala Glu Val Val Glu Trp Asp Val Ile Leu
            580                     585                     590

Asp Asn Pro Ala Leu Thr Leu Glu Val Leu Glu Gln Ala His Val Arg
        595                     600                     605

Lys Pro Val Asn Val Gln Met Ile Phe Ser Asn Pro Leu Asp Gln Pro
    610                     615                     620

Val Arg Asn Cys Val Leu Leu Val Glu Gly Ser Gly Cys Ser Val Ala
625                     630                     635                     640

Ala Ser Arg Leu Met Cys His Pro Cys Val Pro Lys Glu Lys Ser Arg
            645                     650                     655

Ile Arg Phe Glu Ile Phe Pro Thr Arg Ser Gly Thr Lys Gln Leu Leu
            660                     665                     670

Ala Asp Phe Ser Cys Asn Lys Phe Pro Thr Ile Lys Ala Met Leu Pro
        675                     680                     685

Ile Asp Val Ser Glu
690

5,616,500

-continued ( 2 ) INFORMATION FOR SEQ ID NO:112:

( i ) SEQUENCE CHARACTERISTICS:
        ( A ) LENGTH: 693 amino acids
        ( B ) TYPE: amino acid
        ( D ) TOPOLOGY: linear ( i i ) MOLECULE TYPE: protein ( x i ) SEQUENCE DESCRIPTION: SEQ ID NO:112:

| Met | Ala | Ala | Leu | Gly | Val | Gln | Ser | Ile | Asn | Trp | Gln | Lys | Ala | Phe | Asn |
|---|---|---|---|---|---|---|---|---|---|---|---|---|---|---|---|
| 1 | | | | 5 | | | | | 10 | | | | | 15 | |
| Arg | Gln | Ala | His | His | Thr | Asp | Lys | Phe | Ser | Ser | Gln | Glu | Leu | Ile | Leu |
| | | | 20 | | | | 25 | | | | | 30 | | | |
| Arg | Arg | Gly | Gln | Asn | Phe | Gln | Val | Leu | Met | Ile | Met | Asn | Lys | Gly | Leu |
| | | 35 | | | | 40 | | | | | 45 | | | | |
| Gly | Ser | Asn | Glu | Arg | Leu | Glu | Phe | Ile | Asp | Thr | Thr | Gly | Pro | Tyr | Pro |
| | 50 | | | | | 55 | | | | | 60 | | | | |
| Ser | Glu | Ser | Ala | Met | Thr | Lys | Ala | Val | Phe | Pro | Leu | Ser | Asn | Gly | Ser |
| 65 | | | | | 70 | | | | | 75 | | | | | 80 |
| Ser | Gly | Gly | Trp | Ser | Ala | Val | Leu | Gln | Ala | Ser | Asn | Gly | Asn | Thr | Leu |
| | | | | 85 | | | | | 90 | | | | | 95 | |
| Thr | Ile | Ser | Ile | Ser | Ser | Pro | Ala | Ser | Ala | Pro | Ile | Gly | Arg | Tyr | Thr |
| | | | 100 | | | | | 105 | | | | | 110 | | |
| Met | Ala | Leu | Gln | Ile | Phe | Ser | Gln | Gly | Gly | Ile | Ser | Ser | Val | Lys | Leu |
| | | | 115 | | | | 120 | | | | | 125 | | | |
| Gly | Thr | Phe | Ile | Leu | Leu | Phe | Asn | Pro | Trp | Leu | Asn | Val | Asp | Ser | Val |
| | | 130 | | | | 135 | | | | | 140 | | | | |
| Phe | Met | Gly | Asn | His | Ala | Glu | Arg | Glu | Glu | Tyr | Val | Gln | Glu | Asp | Ala |
| 145 | | | | | 150 | | | | | 155 | | | | | 160 |
| Gly | Ile | Ile | Phe | Val | Gly | Ser | Thr | Asn | Arg | Ile | Gly | Met | Ile | Gly | Trp |
| | | | | 165 | | | | | 170 | | | | | 175 | |
| Asn | Phe | Gly | Gln | Phe | Glu | Glu | Asp | Ile | Leu | Ser | Ile | Cys | Leu | Ser | Ile |
| | | | 180 | | | | | 185 | | | | | 190 | | |
| Leu | Asp | Arg | Ser | Leu | Asn | Phe | Arg | Arg | Asp | Ala | Ala | Thr | Asp | Val | Ala |
| | | 195 | | | | | 200 | | | | | 205 | | | |
| Ser | Arg | Asn | Asp | Pro | Lys | Tyr | Val | Gly | Arg | Val | Leu | Ser | Ala | Met | Ile |
| | 210 | | | | | 215 | | | | | 220 | | | | |
| Asn | Ser | Asn | Asp | Asp | Asn | Gly | Val | Leu | Ala | Gly | Asn | Trp | Ser | Gly | Thr |
| 225 | | | | | 230 | | | | | 235 | | | | | 240 |
| Tyr | Thr | Gly | Gly | Arg | Asp | Pro | Arg | Ser | Trp | Asp | Gly | Ser | Val | Glu | Ile |
| | | | | 245 | | | | | 250 | | | | | 255 | |
| Leu | Lys | Asn | Trp | Lys | Lys | Ser | Gly | Phe | Ser | Pro | Val | Arg | Tyr | Gly | Gln |
| | | | 260 | | | | | 265 | | | | | 270 | | |
| Cys | Trp | Val | Phe | Ala | Gly | Thr | Leu | Asn | Thr | Ala | Leu | Arg | Ser | Leu | Gly |
| | | 275 | | | | | 280 | | | | | 285 | | | |
| Ile | Pro | Ser | Arg | Val | Ile | Thr | Asn | Phe | Asn | Ser | Ala | His | Asp | Thr | Asp |
| | 290 | | | | | 295 | | | | | 300 | | | | |
| Arg | Asn | Leu | Ser | Val | Asp | Val | Tyr | Tyr | Asp | Pro | Met | Gly | Asn | Pro | Leu |
| 305 | | | | | 310 | | | | | 315 | | | | | 320 |
| Asp | Lys | Gly | Ser | Asp | Ser | Val | Trp | Asn | Phe | His | Val | Trp | Asn | Glu | Gly |
| | | | | 325 | | | | | 330 | | | | | 335 | |
| Trp | Phe | Val | Arg | Ser | Asp | Leu | Gly | Pro | Pro | Tyr | Gly | Gly | Trp | Gln | Val |
| | | | 340 | | | | | 345 | | | | | 350 | | |
| Leu | Asp | Ala | Thr | Pro | Gln | Glu | Arg | Ser | Gln | Gly | Val | Phe | Gln | Cys | Gly |
| | | 355 | | | | | 360 | | | | | 365 | | | |

```
Pro  Ala  Ser  Val  Ile  Gly  Val  Arg  Glu  Gly  Asp  Val  Gln  Leu  Asn  Phe
     370            375                      380

Asp  Met  Pro  Phe  Ile  Phe  Ala  Glu  Val  Asn  Ala  Asp  Arg  Ile  Thr  Trp
385                      390                      395                      400

Leu  Tyr  Asp  Asn  Thr  Thr  Gly  Lys  Gln  Trp  Lys  Asn  Ser  Val  Asn  Ser
               405                      410                      415

His  Thr  Ile  Gly  Arg  Tyr  Ile  Ser  Thr  Lys  Ala  Val  Gly  Ser  Asn  Ala
               420                      425                      430

Arg  Met  Asp  Val  Thr  Asp  Lys  Tyr  Lys  Tyr  Pro  Glu  Gly  Ser  Asp  Gln
          435                      440                      445

Glu  Arg  Gln  Val  Phe  Gln  Lys  Ala  Leu  Gly  Lys  Leu  Lys  Pro  Asn  Thr
     450                      455                      460

Pro  Phe  Ala  Ala  Thr  Ser  Ser  Met  Gly  Leu  Glu  Thr  Glu  Glu  Gln  Glu
465                      470                      475                      480

Pro  Ser  Ile  Ile  Gly  Lys  Leu  Lys  Val  Ala  Gly  Met  Leu  Ala  Val  Gly
               485                      490                      495

Lys  Glu  Val  Asn  Leu  Val  Leu  Leu  Leu  Lys  Asn  Leu  Ser  Arg  Asp  Thr
                500                      505                      510

Lys  Thr  Val  Thr  Val  Asn  Met  Thr  Ala  Trp  Thr  Ile  Ile  Tyr  Asn  Gly
          515                      520                      525

Thr  Leu  Val  His  Glu  Val  Trp  Lys  Asp  Ser  Ala  Thr  Met  Ser  Leu  Asp
     530                      535                      540

Pro  Glu  Glu  Glu  Ala  Glu  His  Pro  Ile  Lys  Ile  Ser  Tyr  Ala  Gln  Tyr
545                      550                      555                      560

Glu  Arg  Tyr  Leu  Lys  Ser  Asp  Asn  Met  Ile  Arg  Ile  Thr  Ala  Val  Cys
               565                      570                      575

Lys  Val  Pro  Asp  Glu  Ser  Glu  Val  Val  Val  Glu  Arg  Asp  Ile  Ile  Leu
          580                      585                      590

Asp  Asn  Pro  Thr  Leu  Thr  Leu  Glu  Val  Leu  Asn  Glu  Ala  Arg  Val  Arg
          595                      600                      605

Lys  Pro  Val  Asn  Val  Gln  Met  Leu  Phe  Ser  Asn  Pro  Leu  Asp  Glu  Pro
     610                      615                      620

Val  Arg  Asp  Cys  Val  Leu  Met  Val  Glu  Gly  Ser  Gly  Leu  Leu  Leu  Gly
625                      630                      635                      640

Asn  Leu  Lys  Ile  Asp  Val  Pro  Thr  Leu  Gly  Pro  Lys  Glu  Arg  Ser  Arg
               645                      650                      655

Val  Arg  Phe  Asp  Ile  Leu  Pro  Ser  Arg  Ser  Gly  Thr  Lys  Gln  Leu  Leu
               660                      665                      670

Ala  Asp  Phe  Ser  Cys  Asn  Lys  Phe  Pro  Ala  Ile  Lys  Ala  Met  Leu  Ser
          675                      680                      685

Ile  Asp  Val  Ala  Glu
     690
```

( 2 ) INFORMATION FOR SEQ ID NO:113:

( i ) SEQUENCE CHARACTERISTICS:
         ( A ) LENGTH: 51 amino acids
         ( B ) TYPE: amino acid
         ( C ) STRANDEDNESS: single
         ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:113:

```
Thr Ala Ala Ala His Gly Ser Lys Pro Asn Val Tyr Ala Asn Arg Gly
 1               5                  10                  15

Ser Ala Glu Asp Val Ala Met Gln Val Glu Ala Gln Asp Ala Val Met
            20                  25                  30

Gly Gln Asp Leu Met Val Ser Val Met Leu Ile Asn His Ser Ser Ser
            35                  40                  45

Arg Arg Thr
        50
```

( 2 ) INFORMATION FOR SEQ ID NO:114:

( i ) SEQUENCE CHARACTERISTICS:
        ( A ) LENGTH: 52 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:114:

```
Arg Ala Asn His Leu Asn Lys Leu Ala Glu Lys Glu Glu Thr Gln Glu
 1               5                  10                  15

Met Ala Thr Gly Val Ala Met Arg Ile Arg Val Gly Gln Ser Met Asn
            20                  25                  30

Met Gly Ser Asp Phe Asp Val Phe Ala His Ile Thr Asn Asn Thr Ala
            35                  40                  45

Glu Glu Tyr Val
        50
```

( 2 ) INFORMATION FOR SEQ ID NO:115:

( i ) SEQUENCE CHARACTERISTICS:
        ( A ) LENGTH: 69 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( x i ) SEQUENCE DESCRIPTION: SEQ ID NO:115:

```
Lys Ala Leu Gly Lys Leu Lys Pro Asn Thr Pro Phe Ala Ala Thr Ser
 1               5                  10                  15

Ser Met Gly Leu Glu Thr Glu Glu Gln Glu Pro Ser Ile Ser Gly Lys
            20                  25                  30

Leu Lys Val Ala Gly Met Leu Ala Val Gly Lys Glu Val Asn Leu Val
            35                  40                  45

Leu Leu Leu Lys Asn Leu Ser Arg Asp Thr Lys Thr Val Thr Val Asn
        50                  55                  60

Met Thr Ala Trp Thr
 65
```

(2) INFORMATION FOR SEQ ID NO:116:

(i) SEQUENCE CHARACTERISTICS:
        (A) LENGTH: 53 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:116:

```
Thr Ala Leu Met Tyr Gly Ala Lys Lys Pro Leu Asn Thr Glu Gly Val
 1               5                  10                      15

Met Lys Ser Arg Ser Asn Val Asp Met Asp Phe Glu Val Glu Asn Ala
            20                  25                  30

Val Leu Gly Lys Asp Phe Lys Leu Ser Ile Thr Glu Arg Asn Asn Ser
        35                  40                  45

His Asn Arg Tyr Thr
 50
```

(2) INFORMATION FOR SEQ ID NO:117:

(i) SEQUENCE CHARACTERISTICS:
        (A) LENGTH: 57 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:117:

```
Arg Val Glu Lys Glu Lys Met Glu Arg Glu Lys Asp Asn Gly Ile Arg
 1               5                  10                      15

Pro Pro Ser Leu Glu Thr Ala Ser Pro Leu Tyr Leu Leu Leu Lys Ala
            20                  25                  30

Pro Ser Ser Leu Pro Leu Arg Gly Asp Ala Gln Ile Ser Val Thr Leu
        35                  40                  45

Val Asn His Ser Glu Gln Glu Lys Ala
 50                  55
```